US011020261B2

(12) United States Patent
Lear et al.

(10) Patent No.: US 11,020,261 B2
(45) Date of Patent: Jun. 1, 2021

(54) PATCH SYSTEMS FOR USE WITH ASSISTIVE EXOSUIT

(71) Applicant: SEISMIC HOLDINGS, INC., Menlo Park, CA (US)

(72) Inventors: Melinda Cromie Lear, Menlo Park, CA (US); Katherine Goss Witherspoon, Redwood City, CA (US); Megan Grant, San Francisco, CA (US); Nicole Ida Kernbaum, Sunnyvale, CA (US); Richard Mahoney, Los Altos, CA (US); Mallory L. Tayson-Frederick, Oakland, CA (US); Louis Calvin Fielding, San Carlos, CA (US); Violet Riggs, San Francisco, CA (US); Erik Shahoian, Sonoma, CA (US); Mary Elizabeth Hogue, San Francisco, CA (US)

(73) Assignee: SEISMIC HOLDINGS, INC., Menlo Park, CA (US)

( * ) Notice: Subject to any disclaimer, the term of this patent is extended or adjusted under 35 U.S.C. 154(b) by 319 days.

(21) Appl. No.: 15/836,496

(22) Filed: Dec. 8, 2017

(65) Prior Publication Data
US 2018/0153722 A1 Jun. 7, 2018

Related U.S. Application Data

(63) Continuation-in-part of application No. 15/684,466, filed on Aug. 23, 2017.
(Continued)

(51) Int. Cl.
*A61F 5/01* (2006.01)
*A61B 5/00* (2006.01)
(Continued)

(52) U.S. Cl.
CPC .............. *A61F 5/0102* (2013.01); *A61B 5/11* (2013.01); *A61B 5/1126* (2013.01);
(Continued)

(58) Field of Classification Search
CPC .......... A61H 1/00; A61H 1/02; A61H 1/0237; A61H 1/024; A61H 1/0244;
(Continued)

(56) References Cited

U.S. PATENT DOCUMENTS 4,697,808 A * 10/1987 Larson .................. A61F 5/0102
   482/4
6,689,074 B2   2/2004 Seto et al.
(Continued)

FOREIGN PATENT DOCUMENTS

FR          3046100 A1    6/2017
WO     2014/194257 A1   12/2014
(Continued)

*Primary Examiner* — Samchuan C Yao
*Assistant Examiner* — Matthew Standard
(74) *Attorney, Agent, or Firm* — Van Court & Aldridge LLP

(57) ABSTRACT

Exosuit systems and methods according to various embodiments are described herein. The exosuit system can be a suit that is worn by a wearer on the outside of his or her body. It may be worn under the wearer's normal clothing, over their clothing, between layers of clothing, or may be the wearer's primary clothing itself. The exosuit may be assistive, as it physically assists the wearer in performing particular activities, or can provide other functionality such as communication to the wearer through physical expressions to the body, engagement of the environment, or capturing of information from the wearer. One or more patch assemblies may be removably coupled to the exosuit.

16 Claims, 65 Drawing Sheets

Related U.S. Application Data

(60) Provisional application No. 62/431,779, filed on Dec. 8, 2016, provisional application No. 62/378,471, filed on Aug. 23, 2016, provisional application No. 62/378,555, filed on Aug. 23, 2016.

(51) Int. Cl.
  *B25J 9/00* (2006.01)
  *A61B 5/11* (2006.01)
  *A61F 2/70* (2006.01)
  *A61B 5/369* (2021.01)

(52) U.S. Cl.
  CPC .......... *A61B 5/6811* (2013.01); *A61B 5/6812* (2013.01); *A61B 5/7267* (2013.01); *A61F 2/70* (2013.01); *B25J 9/0006* (2013.01); *A61B 5/369* (2021.01); *A61B 2562/0219* (2013.01)

(58) Field of Classification Search
  CPC .. A61H 2001/0211; A61H 3/00; A61H 3/008; A61H 2201/0107; A61H 2201/0157; A61H 2201/12; A61H 2201/1207; A61H 2201/123; A61H 2201/1481; A61H 2201/149; A61H 2201/16; A61H 2201/165; A61H 2201/1652; A61H 2201/1664; A61H 2201/5058; A61H 2201/5061; A61H 2201/5064; A61H 2201/5069; A61H 2201/5079; A61H 2201/5084; A61H 2203/04; A61H 2203/0406; A61H 2205/06; A61H 2205/10; A61H 2205/102; A61F 5/0102; A61F 5/0123; A61F 5/0125; A61F 2/60; A61F 2/604; A61F 2/605; A61F 2/608; A61F 2/607; A41D 13/00; A41D 13/02; A41D 13/1236; A41D 15/00; A41D 15/04; A41D 2400/32; A41D 2600/00; A41D 2600/10; A41D 2600/20; A41D 31/00; A41D 31/02; A41D 31/0005; A41D 31/0015; A41D 31/0016; B25J 9/0006

See application file for complete search history.

(56) References Cited

U.S. PATENT DOCUMENTS

| | | |
|---|---|---|
| 7,128,707 B2 | 10/2006 | Banik |
| 7,190,141 B1 | 3/2007 | Ashrafiuon et al. |
| 8,723,471 B2 | 5/2014 | Eerenbeemd et al. |
| 9,149,938 B1 | 10/2015 | Summer et al. |
| 9,266,233 B2 | 2/2016 | Kombluh et al. |
| 9,351,900 B2 | 5/2016 | Walsh et al. |
| 2003/0120183 A1 | 6/2003 | Simmons |
| 2006/0211956 A1 | 9/2006 | Sankai |
| 2006/0249315 A1 | 11/2006 | Herr et al. |
| 2007/0135279 A1* | 6/2007 | Purdy ................ A63B 21/0004 482/124 |
| 2007/0265140 A1 | 11/2007 | Kim et al. |
| 2008/0077057 A1 | 3/2008 | Peles |
| 2009/0306548 A1 | 12/2009 | Bhugra et al. |
| 2010/0144490 A1* | 6/2010 | Purdy .................. A63B 21/154 482/1 |
| 2012/0165158 A1 | 6/2012 | Ren et al. |
| 2013/0040783 A1 | 2/2013 | Duda et al. |
| 2013/0102935 A1 | 4/2013 | Kazerooni et al. |
| 2014/0277739 A1* | 9/2014 | Kornbluh ............ A41D 13/002 700/260 |
| 2015/0173993 A1 | 6/2015 | Walsh et al. |
| 2016/0016309 A1 | 1/2016 | Swift et al. |
| 2016/0023350 A1 | 1/2016 | Holgate et al. |
| 2016/0058644 A1 | 3/2016 | Cheatham, III et al. |
| 2016/0139666 A1 | 5/2016 | Rubin et al. |
| 2016/0331560 A1* | 11/2016 | Tong ........................ A61H 3/00 |
| 2016/0374887 A1* | 12/2016 | Wu ...................... A61F 5/0123 623/31 |
| 2017/0027735 A1 | 2/2017 | Walsh et al. |
| 2017/0202724 A1* | 7/2017 | De Rossi ................ A61H 3/00 |
| 2018/0008502 A1 | 1/2018 | Asbeck et al. |
| 2018/0049903 A1 | 2/2018 | Witherspoon et al. |

FOREIGN PATENT DOCUMENTS

| | | |
|---|---|---|
| WO | 2015/088863 A2 | 6/2015 |
| WO | 2015/153633 A2 | 10/2015 |
| WO | 2016/104330 A1 | 6/2016 |
| WO | 2016/138264 A1 | 9/2016 |

* cited by examiner

| Movement | Standing or Seated, Posture |
|---|---|
| Modes | Low/Med/High Speeds and/or Support |
| Hip Flexors | Extend and Contract with User Gait Cycle |
| Hip Extensors | Extend and Contract with User Gait Cycle |
| Sensor Input | IMUs, Flexdrive Force, Speed/Length |

PATCH SYSTEMS FOR USE WITH ASSISTIVE EXOSUIT

CROSS-REFERENCE TO RELATED APPLICATIONS

This application claims priority to U.S. Provisional Patent Application No. 62/431,779, filed Dec. 8, 2016, the disclosure of which is incorporated by reference in its entirety. This application is a continuation-in-part of U.S. patent application Ser. No. 15/684,466, filed Aug. 23, 2017, which claims priority to U.S. Provisional Patent Application No. 62/378,471, filed Aug. 23, 2016, U.S. Provisional Patent Application No. 62/378,555, filed Aug. 23, 2016, and U.S. Provisional Patent Application No. 62/431,779, filed Dec. 8, 2016, the disclosures of which are incorporated by reference in their entireties.

BACKGROUND

Wearable robotic systems have been developed for augmentation of humans' natural capabilities, or to replace functionality lost due to injury or illness. One example of these systems is the ReWalk exoskeleton system by ReWalk robotics. The ReWalk system comprises a rigid exoskeleton with powered actuators at the knee and hip joints, to enable assisted ambulation for paraplegic patients. However, the system comprises a large, rigid frame; requires assistance of a caregiver; and it is intended for patients with paraplegia due to spinal cord injury. The ReWalk device is not appropriate for people with less degrees of disability, nor is it appropriate for functional augmentation for able-bodied people.

Examples of exosuit systems are described in the U.S. Pat. No. 9,266,233, titled "Exosuit System," which includes several concepts for exosuits comprising flexible linear actuators and clutched compliance elements to apply and/or modulate forces and/or compliances between segments of the body of the wearer. While the disclosure in the U.S. Pat. No. 9,266,233 broadly describes technologies that may be utilized in an exosuit system, it does not teach the requirements, interactions, orientations and locations of the relevant subsystems required to provide an assistive exosuit system for certain applications.

SUMMARY

Exosuit systems and methods according to various embodiments are described herein. The exosuit system can be a suit that is worn by a wearer on the outside of his or her body. It may be worn under the wearer's normal clothing, over their clothing, between layers of clothing, or may be the wearer's primary clothing itself. The exosuit may be assistive, as it physically assists the wearer in performing particular activities, or can provide other functionality such as communication to the wearer through physical expressions to the body, engagement of the environment, or capturing of information from the wearer. One or more patch assemblies may be removably coupled to the exosuit.

In one embodiment, a patch assembly is provided that includes a housing detachably coupled to an exosuit. The housing can include mounting components for securing the housing to the exosuit, at least one flexible linear actuator (FLA), at least one battery, and control electronics coupled to the at least one FLA and the at least one battery and configured to selectively activate the at least one FLA to provide muscle movement assistance to a user of the exosuit.

In another embodiment, an exosuit is provided that can include a base layer having a plurality of load distribution members and a plurality of patch assemblies detachably coupled to the base layer via the plurality of load distribution members. Each one of the plurality of patch assemblies can include a housing that can include mounting components for securing the housing to the base layer, at least one flexible linear actuator (FLA), at least one battery, and control electronics coupled to the at least one FLA and the at least one battery and configured to selectively activate the at least one FLA to provide muscle movement assistance to a user of the exosuit.

In yet another embodiment, a multiple assistive movement patch assembly is provided that can include a flexible substrate constructed to be detachably coupled to a plurality of load bearing members existing on anterior and posterior sides of an exosuit, a plurality of sensors secured to the flexible substrate, a plurality of batteries secured to the flexible substrate, a plurality of flexible linear actuators (FLAs) secured to the flexible substrate, control electronics secured to the flexible substrate, and a power and communications network that is coupled to the plurality of sensors, the plurality of batteries, the plurality of FLAs, and the control electronics, wherein the control electronics are operative to selectively activate the plurality of FLAs to provide muscle movement assistance to a user of the exosuit.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

Figure 1A:
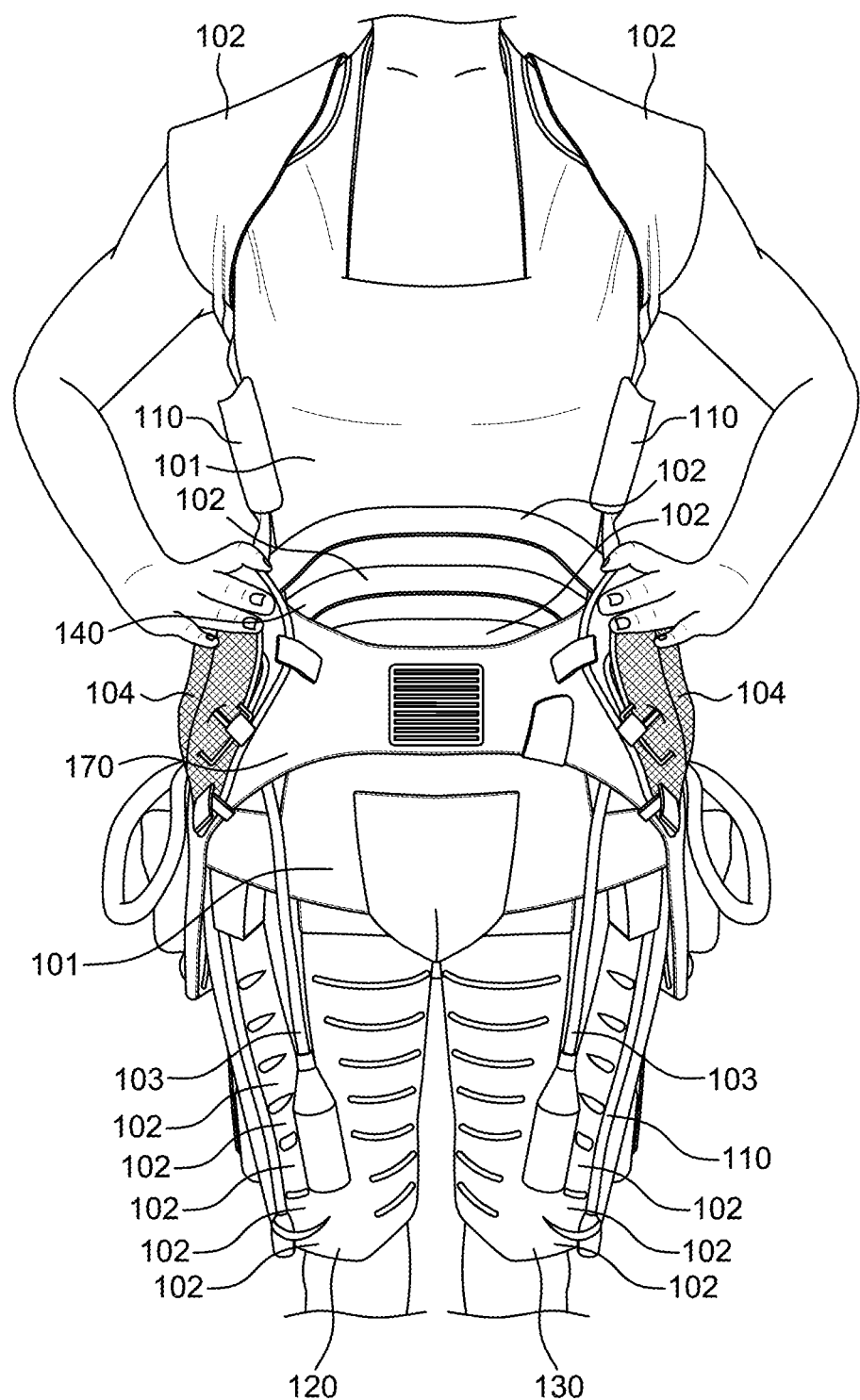
FIG. 1A shows a front view of an assistive exosuit undergarment with the stability layer continuously integrated with the base layer according to some embodiments of the present disclosure.

In the following description, numerous specific details are set forth regarding the systems, methods and media of the disclosed subject matter and the environment in which such systems, methods and media may operate, etc., in order to provide a thorough understanding of the disclosed subject matter. It can be apparent to one skilled in the art, however, that the disclosed subject matter may be practiced without such specific details, and that certain features, which are well known in the art, are not described in detail in order to avoid complication of the disclosed subject matter. In addition, it can be understood that the examples provided below are exemplary, and that it is contemplated that there are other systems, methods and media that are within the scope of the disclosed subject matter.

In the descriptions that follow, an exosuit or assistive exosuit is a suit that is worn by a wearer on the outside of his or her body. It may be worn under the wearer's normal clothing, over their clothing, between layers of clothing, or may be the wearer's primary clothing itself. The exosuit may be assistive, as it physically assists the wearer in performing particular activities, or can provide other functionality such as communication to the wearer through physical expressions to the body, engagement of the environment, or capturing of information from the wearer. In some embodiments, an powered exosuit system can include several subsystems, or layers. In some embodiments, the powered exosuit system can include more or less subsystems or layers. The subsystems or layers can include the base layer, stability layer, power layer, sensor and controls layer, a covering layer, and user interface/user experience (UI/UX) layer.

Base Layer

The base layer provides the interfaces between the exosuit system and the wearer's body. The base layer may be adapted to be worn directly against the wearer's skin, between undergarments and outer layers of clothing, over outer layers of clothing or a combination thereof, or the base layer may be designed to be worn as primary clothing itself. In some embodiments, the base layer can be adapted to be both comfortable and unobtrusive, as well as to comfortably and efficiently transmit loads from the stability layer and power layer to the wearer's body in order to provide the desired assistance. The base layer can typically comprise several different material types to achieve these purposes. Elastic materials may provide compliance to conform to the wearer's body and allow for ranges of movement. The innermost layer is typically adapted to grip the wearer's skin, undergarments or clothing so that the base layer does not slip as loads are applied. Substantially inextensible materials may be used to transfer loads from the stability layer and power layer to the wearer's body. These materials may be substantially inextensible in one axis, yet flexible or extensible in other axes such that the load transmission is along preferred paths. The load transmission paths may be optimized to distribute the loads across regions of the wearer's body to minimize the forces felt by the wearer, while providing efficient load transfer with minimal loss and not causing the base layer to slip. Collectively, this load transmission configuration within the base layer may be referred to as a load distribution member. Load distribution members refer to flexible elements that distribute loads across a region of the wearer's body. Examples of load distribution members can be found in International Application PCT/US16/19565, titled "Flexgrip," the contents of which are incorporated herein by reference.

The load distribution members may incorporate one or more catenary curves to distribute loads across the wearer's body. Multiple load distribution members or catenary curves may be joined with pivot points, such that as loads are applied to the structure, the arrangement of the load distribution members pivots tightens or constricts on the body to increase the gripping strength. Compressive elements such as battens, rods, or stays may be used to transfer loads to different areas of the base layer for comfort or structural purposes. For example, a power layer component may terminate in the middle back due to its size and orientation requirements, however the load distribution members that anchor the power layer component may reside on the lower back. In this case, one or more compressive elements may transfer the load from the power layer component at the middle back to the load distribution member at the lower back.

The load distribution members may be constructed using multiple fabrication and textile application techniques. For example, the load distribution member can be constructed from a layered woven 45°/90° with bonded edge, spandex tooth, organza (poly) woven 45°/90° with bonded edge, organza (cotton/silk) woven 45°/90°, and Tyvek (non-woven laser). The load distribution member may be constructed using knit and lacing or horse hair and spandex tooth. The load distribution member may be constructed using channels and/or laces.

The base layer may include a flexible underlayer that is constructed to compress against a portion of the wearer's body, either directly to the skin, or to a clothing layer, and also provides a relatively high grip surface for one or more load distribution members to attach thereto. The load distribution members can be coupled to the underlayer to facilitate transmission of shears or other forces from the members, via the flexible underlayer, to skin of a body segment or to clothing worn over the body segment, to maintain the trajectories of the members relative to such a body segment, or to provide some other functionality. Such a flexible underlayer could have a flexibility and/or compliance that differs from that of the member (e.g., that is less than that of the members, at least in a direction along the members), such that the member can transmit forces along their length and evenly distribute shear forces and/or pressures, via the flexible underlayer, to skin of a body segment to which a flexible body harness is mounted.

Further, such a flexible underlayer can be configured to provide additional functionality. The material of the flexible underlayer could include anti-bacterial, anti-fungal, or other agents (e.g., silver nanoparticles) to prevent the growth of microorganisms. The flexible underlayer can be configured to manage the transport of heat and/or moisture (e.g., sweat) from a wearer to improve the comfort and efficiency of activity of the wearer. The flexible underlayer can include straps, seams, hook-and-loop fasteners, clasps, zippers, or other elements configured to maintain a specified relationship between elements of the load distribution members and aspects of a wearer's anatomy. The underlayer can additionally increase the ease with which a wearer can don and/or doff the flexible body harness and/or a system (e.g., a flexible exosuit system) or garment that includes the flexible body harness. The underlayer can additionally be configured to protect the wearer from ballistic weapons, sharp edges, shrapnel, or other environmental hazards (by including, e.g., panels or flexible elements of para-aramid or other high-strength materials).

The base layer can additionally include features such as size adjustments, openings and electro-mechanical integration features to improve ease of use and comfort for the wearer.

Size Adjustment

Size adjustment features permit the exosuit to be adjusted to the wearer's body. The size adjustments may allow the suit to be tightened or loosened about the length or circumference of the torso or limbs. The adjustments may comprise lacing, the Boa system, webbing, elastic, hook-and-loop or other fasteners. Size adjustment may be accomplished by the load distribution members themselves, as they constrict onto the wearer when loaded. In one example, the torso circumference may be tightened with corset-style lacing, the legs tightened with hook-and-loop in a double-back configuration, and the length and shoulder height adjusted with webbing and tension-lock fasteners such as cam-locks, D-rings or the like. The size adjustment features in the base layer may be actuated by the power layer to dynamically adjust the base layer to the wearer's body in different positions, in order to maintain consistent pressure and comfort for the wearer. For example, the base layer may be required to tighten on the thighs when standing, and loosen when sitting such that the base layer does not excessively constrict the thighs when seated. The dynamic size adjustment may be controlled by the sensor and controls layer, for example by detecting pressures or forces in the base layer and actuating the power layer to consistently attain the desired force or pressure. This feature does not necessarily cause the suit to provide physical assistance, but can create a more comfortable experience for the wearer, or allow the physical assistance elements of the suit to perform better or differently depending on the purpose of the movement assistance.

Opening

Opening features in the base layer may be provided to facilitate donning (putting the exosuit on) and doffing (taking the exosuit off) for the wearer. Opening features may comprise zippers, hook-and-loop, snaps, buttons or other textile fasteners. In one example, a front, central zipper provides an opening feature for the torso, while hook-and-loop fasteners provide opening features for the legs and shoulders. In this case, the hook-and-loop fasteners provide both opening and adjustment features. In other examples, the exosuit may simply have large openings, for example around the arms or neck, and elastic panels that allow the suit to be dinned and doffed without specific closure mechanisms. A truncated load distribution member may be simply extended to tighten on the wearer's body. Openings may be provided to facilitate toileting so the user can keep the exosuit on, but only have to remove or open a relatively small portion to use the bathroom.

Electro-Mechanical Integration

Electro-mechanical integration features attach components of the stability layer, power layer and sensor and controls layer into the base layer for integration into the exosuit. The integration features may be for mechanical, structural, comfort, protective or cosmetic purposes. Structural integration features anchor components of the other layers to the base layer. For the stability and power layers, the structural integration features provide for load-transmission to the base layer and load distribution members, and may accommodate specific degrees of freedom at the attachment point. For example, a snap or rivet anchoring a stability or power layer element may provide both load transmission to the base layer, as well as a pivoting degree of freedom. Stitched, adhesive, or bonded anchors may provide load transmission with or without the pivoting degree of freedom. A sliding anchor, for example along a sleeve or rail, may provide a translational degree of freedom. Anchors may be separable, such as with snaps, buckles, clasps or hooks; or may be inseparable, such as with stitching, adhesives or other bonding. Size adjustment features as described above may allow adjustment and customization of the stability and power layers, for example to adjust the tension of spring or elastic elements in the passive layer, or to adjust the length of actuators in the power layer.

Other integration features such as loops, pockets, and mounting hardware may simply provide attachment to components that do not have significant load transmission requirements, such as batteries, circuit boards, sensors, or cables. In some cases, components may be directly integrated into textile components of the base layer. For example, cables or connectors may include conductive elements that are directly woven, bonded or otherwise integrated into the base layer.

Electro-mechanical integration features may also protect or cosmetically hide components of the stability, power or sensor and controls layers. Elements of the stability layer (e.g. elastic bands or springs), power layer (e.g. flexible linear actuators or twisted string actuators) or sensor and controls layer (e.g. cables) may travel through sleeves, tubes, or channels integrated into the base layer, which can both conceal and protect these components. The sleeves, tubes, or channels may also permit motion of the component, for example during actuation of a power layer element. The sleeves, channels, or tubes may comprise resistance to collapse, ensuring that the component remains free and uninhibited within.

Enclosures, padding, fabric coverings, or the like may be used to further integrate components of other layers into the base layer for cosmetic, comfort, or protective purposes. For example, components such as motors, batteries, cables, or circuit boards may be housed within an enclosure, fully or partially covered or surrounded in padded material such that the components do not cause discomfort to the wearer, are visually unobtrusive and integrated into the exosuit, and are protected from the environment. Opening and closing features may additionally provide access to these components for service, removal, or replacement.

In some cases—particularly for exosuits configurable for either provisional use or testing—a tether may allow for some electronic and mechanical components to be housed off the suit. In one example, electronics such as circuit boards and batteries may be over-sized, to allow for added configurability or data capture. If the large size of these components makes it undesirable to mount them on the exosuit, they could be located separately from the suit and connected via a physical or wireless tether. Larger, over-powered motors may be attached to the suit via flexible drive linkages that allow actuation of the power layer without requiring large motors to be attached to the suit. Such over-powered configurations allow optimization of exosuit parameters without constraints requiring all components to be attached or integrated into the exosuit.

Electro-mechanical integration features may also include wireless communication. For example, one or more power layer components may be placed at different locations on the exosuit. Rather than utilizing physical electrical connections to the sensors and controls layer, the sensor and controls layer may communicate with the one or more power layer components via wireless communication protocols such as Bluetooth, ZigBee, ultrawide band, or any other suitable communication protocol. This may reduce the electrical interconnections required within the suit. Each of the one or more power layer components may additionally incorporate a local battery such that each power layer component or group of power layer components are independently powered units that do not require direct electrical interconnections to other areas of the exosuit.

Stability Layer

The stability layer provides passive mechanical stability and assistance to the wearer. The stability layer comprises one or more passive (non-powered) spring or elastic elements that generate forces or store energy to provide stability or assistance to the wearer. An elastic element can have an un-deformed, least-energy state. Deformation, e.g. elongation, of the elastic element stores energy and generates a force oriented to return the elastic element toward its least-energy state. For example, elastic elements approximating hip flexors and hip extensors may provide stability to the wearer in a standing position. As the wearer deviates from the standing position, the elastic elements are deformed, generating forces that stabilize the wearer and assist maintaining the standing position. In another example, as a wearer moves from a standing to seated posture, energy is stored in one or more elastic elements, generating a restorative force to assist the wearer when moving from the seated to standing position. Similar passive, elastic elements may be adapted to the torso or other areas of the limbs to provide positional stability or assistance moving to a position where the elastic elements are in their least-energy state.

Elastic elements of the stability layer may be integrated to parts of the base layer or be an integral part of the base layer. For example elastic fabrics containing spandex or similar materials may serve as a combination base/stability layer. Elastic elements may also include discrete components such as springs or segments of elastic material such as silicone or elastic webbing, anchored to the base layer for load transmission at discrete points, as described above.

The stability layer may be adjusted as described above, both to adapt to the wearer's size and individual anatomy, as well as to achieve a desired amount of pre-tension or slack in components of the stability layer in specific positions. For example, some wearers may prefer more pre-tension to provide additional stability in the standing posture, while others may prefer more slack, so that the passive layer does not interfere with other activities such as ambulation.

The stability layer may interface with the power layer to engage, disengage, or adjust the tension or slack in one or more elastic elements. In one example, when the wearer is in a standing position, the power layer may pre-tension one or more elastic elements of the stability layer to a desired amount for maintaining stability in that position. The pre-tension may be further adjusted by the power layer for different positions or activities. In some embodiments, the elastic elements of the stability layer should be able to generate at least 5 lbs force; preferably at least 50 lbs force when elongated.

Power Layer

The power layer can provide active, powered assistance to the wearer, as well as electromechanical clutching to maintain components of the power or stability layers in a desired position or tension. The power layer can include one or more flexible linear actuators (FLA). An FLA is a powered actuator capable of generating a tensile force between two attachment points, over a give stroke length. An FLA is flexible, such that it can follow a contour, for example around a body surface, and therefore the forces at the attachment points are not necessarily aligned. In some embodiments, one or more FLAs can include one or more twisted string actuators. In the descriptions that follow, FLA refers to a flexible linear actuator that exerts a tensile force, contracts or shortens when actuated. The FLA may be used in conjunction with a mechanical clutch that lock the tension force generated by the FLA in place so that the FLA motor does not have to consume power to maintain the desired tension force. Examples of such mechanical clutches are discussed below. In some embodiments, FLAs can include one or more twisted string actuators or flexdrives, as described in further detail in U.S. Pat. No. 9,266,233, titled "Exosuit System," the contents of which are incorporated herein by reference. FLAs may also be used in connection with electrolaminate clutches, which are also described in the U.S. Pat. No. 9,266,233. The electrolaminate clutch (e.g., clutches configured to use electrostatic attraction to generate controllable forces between clutching elements) may provide power savings by locking a tension force without requiring the FLA to maintain the same force.

The powered actuators, or FLAs, are arranged on the base layer, connecting different points on the body, to generate forces for assistance with various activities. The arrangement can often approximate the wearer's muscles, in order to naturally mimic and assist the wearer's own capabilities. For example, one or more FLAs may connect the back of the torso to the back of the legs, thus approximating the wearer's hip extensor muscles. Actuators approximating the hip extensors may assist with activities such as standing from a seated position, sitting from a standing position, walking, or lifting. Similarly, one or more actuators may be arranged approximating other muscle groups, such as the hip flexors, spinal extensors, abdominal muscles or muscles of the arms or legs.

The one or more FLAs approximating a group of muscles are capable of generating at least 10 lb over at least a ½ inch stroke length within 4 seconds. In some embodiments, one or more FLAs approximating a group of muscles may be capable of generating at least 250 lb. over a 6-inch stroke within ½ second. Multiple FLAs, arranged in series or parallel, may be used to approximate a single group of muscles, with the size, length, power, and strength of the FLAs optimized for the group of muscles and activities for which they are utilized.

Sensor and Controls Layer

The sensor and controls layer captures data from the suit and wearer, utilizes the sensor data and other commands to control the power layer based on the activity being performed, and provides suit and wearer data to the UX/UI layer for control and informational purposes.

Sensors such as encoders or potentiometers may measure the length and rotation of the FLAs, while force sensors measure the forces applied by the FLAs. Inertial measurement units (IMUs) measure and enable computation of kinematic data (positions, velocities and accelerations) of points on the suit and wearer. These data enable inverse dynamics calculations of kinetic information (forces, torques) of the suit and wearer. Electromyographic (EMG) sensors may detect the wearer's muscle activity in specific muscle groups. Electronic control systems (ECSs) on the suit may use parameters measured by the sensor layer to control the power layer. Data from the IMUs may indicate both the activity being performed, as well as the speed and intensity. For example, a pattern of IMU or EMG data may enable the ECS to detect that the wearer is walking at a specific pace. This information then enables the ECS, utilizing the sensor data, to control the power layer in order to provide the appropriate assistance to the wearer.

Data from the sensor layer may be further provided to the UX/UI layer, for feedback and information to the wearer, caregivers or service providers.

UX/UI Layer

The UX/UI layer comprises the wearer's and others' interaction and experience with the exosuit system. This layer includes controls of the suit itself such as initiation of activities, as well as feedback to the wearer and caregivers. A retail or service experience may include steps of fitting, calibration, training and maintenance of the exosuit system. Other UX/UI features may include additional lifestyle features such as electronic security, identity protection and health status monitoring.

Wearer Commands/Controls

The assistive exosuit can have a user interface for the wearer to instruct the suit which activity is to be performed, as well as the timing of the activity. In one example, a user may manually instruct the exosuit to enter an activity mode via one or more buttons, a keypad, or a tethered device such as a mobile phone. In another example, the exosuit may detect initiation of an activity from the sensor and controls layer, as described previously. In yet another example, the user may speak a desired activity mode to the suit, which can interpret the spoken request to set the desired mode. The suit may be pre-programmed to perform the activity for a specific duration, until another command is received from the wearer, or until the suit detects that the wearer has ceased the activity. The suit may include fail safe features that, when activated, cause the suit to cease all activity.

The exosuit may have a UX/UI controller that is defined as a node on another user device, such as a computer or mobile smart phone. The exosuit may also be the base for other accessories. For example, the exosuit may include a cell phone chip so that the suit may be capable of receiving both data and voice commands directly similar to a cell phone, and can communicate information and voice signals through such a node. The exosuit control architecture can be configured to allow for other devices to be added as accessories to the exosuit. For example, a video screen may be connected to the exosuit to show images that are related to the use of the suit. The exosuit may be used to interact with smart household devices such as door locks or can be used to turn on smart televisions and adjust channels and other settings. In these modes, the physical assist of the suit can be used to augment or create physical or haptic experiences for the wearer that are related to communication with these devices. For instance, an email could have a pat on the back as a form of physical emoji that when inserted in the email causes the suit to physically tap the wearer or perform some other type of physical expression to the user that adds emphasis to the written email.

The exosuit may provide visual, audio, or haptic feedback or cues to inform the user of various exosuit operations. For example, the exosuit may include vibration motors to provide haptic feedback. As a specific example, two haptic motors may be positioned near the front hip bones to inform the user of suit activity when performing a sit-to-stand assistive movement. In addition, two haptic motors may be positioned near the back hip bones to inform the user of suit activity when performing a stand-to-sit assistive movement. The exosuit may include one or more light emitting diodes (LEDs) to provide visual feedback or cues. For example, LEDS may be placed near the left and/or right shoulders within the peripheral vision of the user. The exosuit may include a speaker or buzzer to provide audio feedback or cues.

In other instances, the interaction of the FLA's with the body through the body harness and otherwise can be used as a form of haptic feedback to the wearer, where changes in the timing of the contraction of the FLA's can indicate certain information to the wearer. For instance, the number or strength of tugs of the FLA on the waist could indicate the amount of battery life remaining or that the suit has entered a ready state for an impending motion.

Retail/Service/Studio Setting

A wearer's first interaction with the assistive exosuit may be within a setting such as a retail location, dealership, clinic, or specialty service provider where an exosuit system is specified or selected for an individual wearer. Alternatively, a sales representative or technician may make a home visit or meet the wearer in an appropriate setting such as a clinic, athletic facility, or in the community. Specification or selection of the exosuit for the individual may comprise selecting from one of a number of sizes of suits or components, or determining custom sizing or figment, as well as specific features, functionality or other requirements of the system for the specific wearer, based on their individual needs. For example, an elderly but otherwise able-bodied wearer may require a suit that provides assistance for activities such as standing from a seated position, maintaining posture while standing, and walking. While this wearer may be able to perform these activities unassisted, the assistive exosuit system can enable this wearer to perform these activities for longer durations with reduced fatigue. Other wearers may have different requirements for sizing of the suit or components, activities to be performed, amount of assistance required, controls needed by the wearer, or the type of data and information to be relayed to the wearer, caregivers, or others.

The studio may be equipped with features that make fitting and testing the exosuit easier for the prospective wearer and support staff. For instance, the studio can have a network that connects to the suit and shares information about the wearer in real time on screens and in other useful applications to customize or otherwise facilitate the experience of the suit for a customer. The studio can have screen displays or other physical displays like lights and sound that link to the movement of the suit to help the wearer acclimate to controlling it. The studio can also have a build in 'obstacle' course or demo setting for testing the use of the suit. The suit control can be linked to experiences in the studio.

Reflex Control

The control of the exosuit may also be linked to the sensors that are measuring the movement of the wearer, or other sensors, for instance on the suit of another person, or sensors in the environment. The motor commands described herein may all be activated or modified by this sensor information. In this example, the suit can exhibit its own reflexes such that the wearer, through intentional or unintentional motions, cues the motion profile of the suit. When sitting, for further example, the physical movement of leaning forward in the charge, as if to indicate an intention to stand up, can be sensed by the suit IMU's and be used to trigger the sit to stand motion profile. In one embodiment, the exosuit may include sensors (e.g., electroencephalograph (EEG) sensor) that are able to monitor brain activity may be used to detect a user's desire to perform a particular movement. For example, if the user is sitting down, the EEG sensor may sense the user's desire to stand up and cause the exosuit to prime itself to assist the user in a sit-to-stand assistive movement.

User Cues

The suit may make sounds or provide other feedback, for instance through quick movements of the motors, as information to the user that the suit has received a command or to describe to the user that a particular motion profile can be applied. In the above reflex control example, the suit may provide a high pitch sound and/or a vibration to the wearer to indicate that it is about to start the movement. This information can help the user to be ready for the suit movements, improving performance and safety. Many types of cues are possible for all movements of the suit.

Machine Learning/AI

Control of the suit includes the use of machine learning techniques to measure movement performance across many instances of one or of many wearers of suits connected via the internet, where the calculation of the best control motion for optimizing performance and improving safety for any one user is based on the aggregate information in all or a subset of the wearers of the suit. The machine learning techniques can be used to provide user specific customization for exosuit assistive movements. For example, a particular user may have an abnormal gait (e.g., due to an car accident) and thus is unable to take even strides. The machine learning may detect this abnormal gait and compensate accordingly for it.

Undergarment Assistive Exosuit System

FIGS. 1A-1F illustrate an undergarment assistive exosuit (UAE) system according to some embodiments of the present disclosure. In some embodiments, an UAE system is intended to be worn under the wearer's clothing, and to focus on physical assistance for core muscles of the body. This embodiment is also a base for extension to embodiments that provide physical assistance with other body sites, including joints of the shoulders, elbow, wrist, and hands, and the knee, ankles, and feet. The description below is only for the focus on the body core.

FIG. 1A shows a front view of a UAE according to some embodiments of the present disclosure. The Base Layer, extending from the shoulders to just above the knees, comprises compliant spandex panels (101) and flexible yet substantially inextensible load distribution members (102). The load distribution members (102) transfer loads from the stability and power layers to the wearer's shoulders, waist and thighs. In this embodiment, the load distribution members (102) comprise a substantially inextensible material arranged in a plurality of curves. The curves generally approximate catenary curves, in order to evenly distribute loads from the stability and power layers. The load distribution members comprise an inner surface that resists slipping along the wearer's body. The arrangement of the load distribution members causes them to constrict on the wearer's body when subjected to loading, further enhancing their grip and resistance to slipping along the wearer's body.

Flexible linear actuators (FLAs) (103) positioned on the fronts of the thighs approximate the hip flexors. An FLA is a powered actuator capable of generating a tensile force between two attachment points, over a give stroke length. An FLA is flexible, such that it can follow a contour, for example around a body surface, and therefore the forces at the attachment points are not necessarily aligned. Electronic components of the power layer and sensor and controls layer are housed in enclosures (104) on the hips. The enclosures (104) can be integrated with the base layer with padding, insulation and textile components for comfort, aesthetics and protection of the components or wearer. For example, fire- or heat-resistant materials may be used around electronics or batteries. Lacing (110) along the sides of the torso and thighs adjusts overall size of the base layer.

Figure 1B:
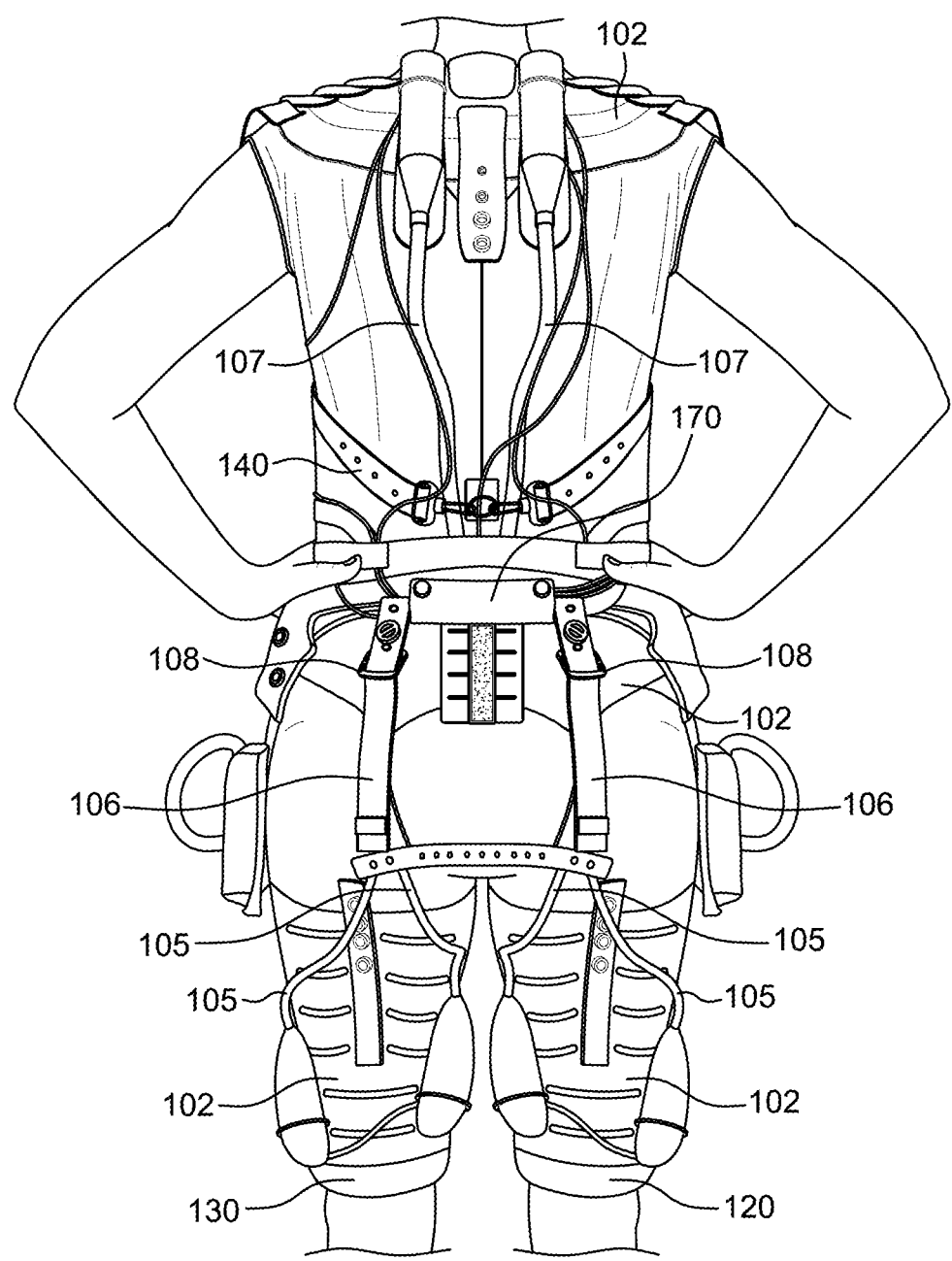
FIG. 1B shows a back view of an assistive exosuit undergarment with the stability layer continuously integrated with the base layer according to some embodiments of the present disclosure.

FIG. 1B shows a back view of the UAE according to some embodiments of the present disclosure. Again, load distribution members (102) at the shoulders, waist, and thigh transfer loads to the base layer and wearer's body. Four FLAs (105) approximate the hip extensor muscles, with two FLAs configured in parallel per hip. The pair of FLAs (105) at each hip are each connected to a tendon element (106) to attach the pair of FLAs to the Load distribution members (102) at the waist. Thus, the combination of the pairs of FLAs (105) and tendons (106) connect between the load distribution members (102) of the thighs and the waist such that when the FLAs are actuated (tightened), an extension moment is generated at the hip. The tendon elements (106) in this example can include webbing with adjustment elements (108) so that the length of the tendon elements can be adjusted to optimize the stroke of the FLAs (105) to the wearer's body. Two FLAs (107) attach in parallel to the load distribution members (102) at the shoulders and the waist thus approximating spinal extensor muscles (e.g. for postural support).

Figure 1C:
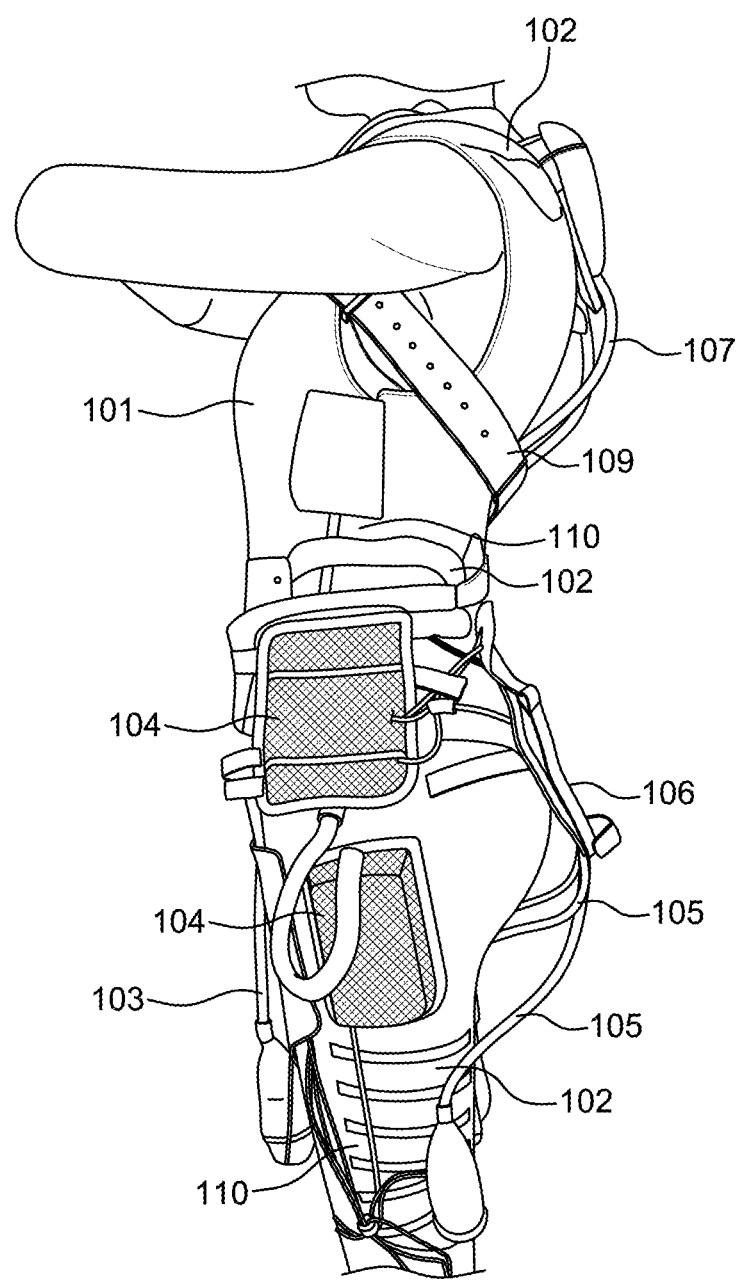
FIG. 1C shows a side view of an assistive exosuit undergarment with the stability layer continuously integrated with the base layer according to some embodiments of the present disclosure.

FIG. 1C shows a side view of the UAE according to some embodiments of the present disclosure. In the side view, the load distribution members approximating the hip flexors (103), hip extensors (105) and spinal extensors (107) are all shown, with the hip extensor FLAs (105) attached to the adjustable tendon elements (106). Electronic components of the power and sensor and controls layers are housed in enclosures (104) that are integrated into the textile base layer. An adjustable shoulder harness (109) attaches to the Load distribution members (102) at the shoulders and waist. Lacing (110) along the sides of the torso and thighs adjusts overall size of the base layer.

Figure 1D:
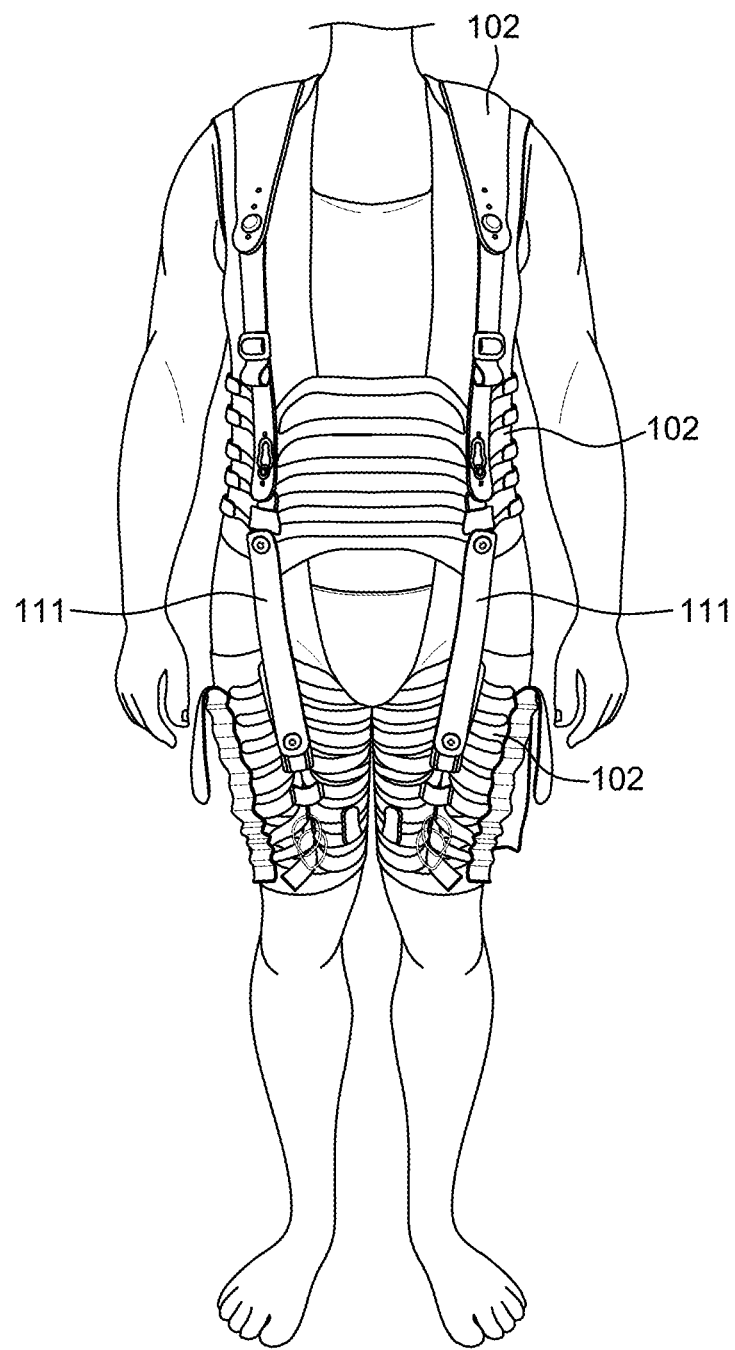
FIG. 1D shows a front view of an assistive exosuit undergarment with discrete stability layer components attached to the base layer (power layer not shown) according to some embodiments of the present disclosure.

FIG. 1D shows a front view of the UAE according to some embodiments of the present disclosure. In FIG. 1D, the power layer and sensor and controls layers are removed to show the stability layer. Two elastic elements (111) of the stability layer approximate hip flexors, attaching to the load distribution members (102) at the waist and thighs. In this example, the elastic elements (111) are strips of silicone covered with spandex fabric. In some embodiments, the elastic element (111) may be made of any other suitable material. In other examples, the elastic elements of the stability layer may be formed more integrally with the base layer.

Figure 1E:
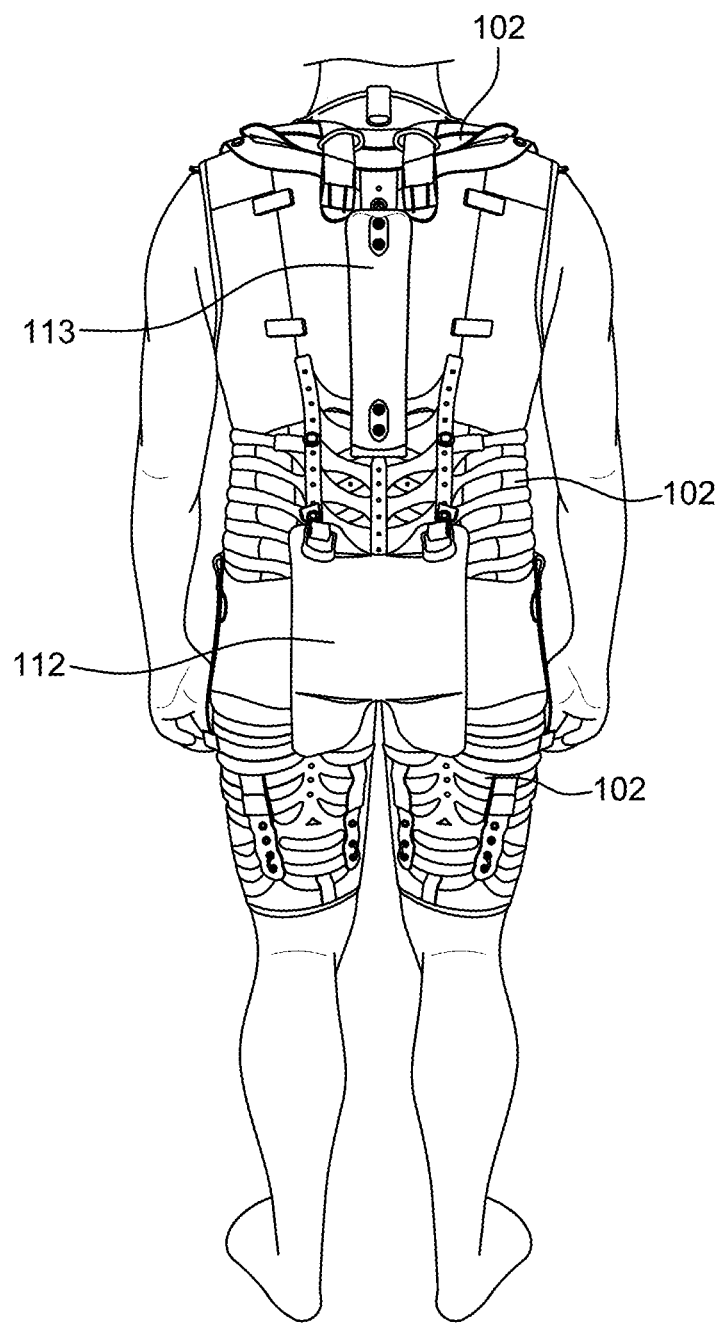
FIG. 1E shows a back view of an assistive exosuit undergarment with discrete stability layer components attached to the base layer (power layer not shown) according to some embodiments of the present disclosure.

FIG. 1E shows a back view of the UAE according to some embodiments of the present disclosure. In FIG. 1E the power layer and sensor and controls layer are removed to show the stability layer. An elastic element of the stability layer (112) approximating the hip extensors or gluteal muscles attaches to the load distribution members (102) at the waist and thighs. Another elastic element of the stability layer (113) approximating the spinal extensors attaches to the load distribution members (102) at the shoulders and waist. As in FIG. 1D, the elastic elements (112, 113) are made of silicone covered with fabric, however in other embodiments the elastic elements may be formed more integrally with the base layer. In some embodiments, the elastic elements (112, 113) may be made of any other suitable material. The elastic elements are typically configured such that moving from a first position to a second position stretches the elastic elements, generating forces biased to return the wearer to the first position. This may provide stability in the first position, or assist the wearer when moving from the second to the first position. In one example, the first position is a standing position and the second position is a seated position. The elastic elements of the stability layer approximating the hip flexors, hip extensors and spinal extensors (111, 112, 113) are configured with a small, nominal preload in the standing (first) position. Small movements from the standing posture can stretch one or more elastic elements of the stability layer, creating one or more forces biased to restore the first position. For example, leaning forward can stretch the hip extensor and spinal extensor elastic elements (112, 113), generating forces biased to restore the standing posture. Conversely, leaning backwards can stretch the hip flexor elastic elements (111), generating forces biased to move the torso forward and again restore the standing posture. Thus, in these scenarios the elastic elements of the stability layer provide stability in the first, standing position. Moving to a second, seated position can stretch the hip extensor and spinal extensor elastic elements (112, 113). These stretched elastic elements (112, 113) can generate forces biased to move the wearer back into the first standing position. While the wearer is seated, the elastic elements are maintained in their stretched state, such that the force is maintained and energy is stored in the elastic elements while the wearer is in the second, seated position. When the wearer desires to return to the standing position, the stored energy and force generated in the elastic elements can assist the wearer.

Figure 1F:
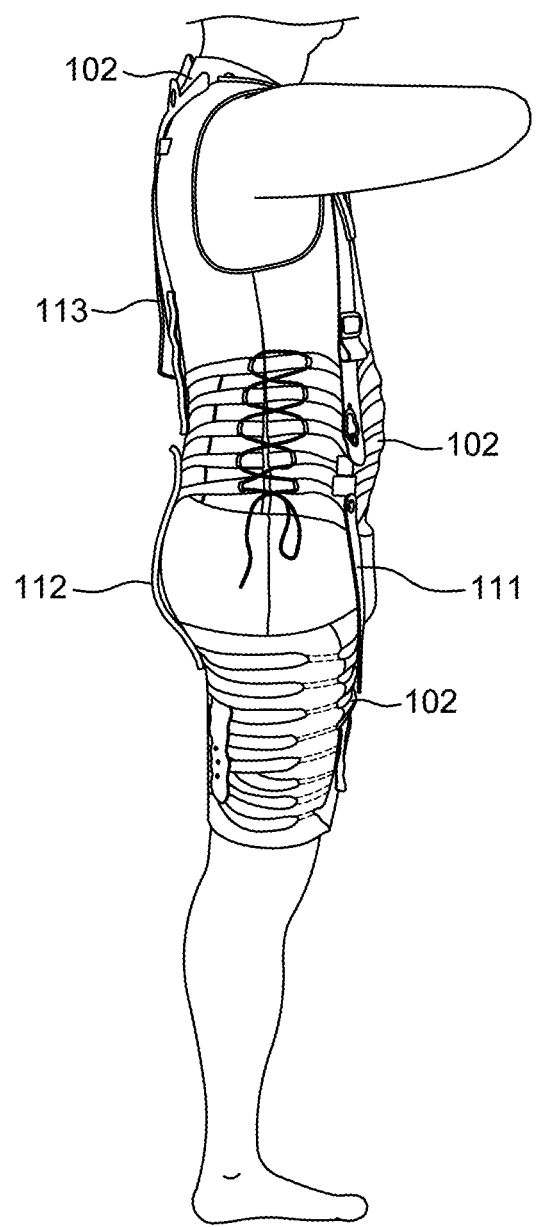
FIG. 1F shows a side view of an assistive exosuit undergarment with discrete stability layer components attached to the base layer (power layer not shown) according to some embodiments of the present disclosure.

FIG. 1F shows a side view of the UAE according to some embodiments of the present disclosure. In FIG. 1F, the power layer and sensor and controls layer are removed to show the stability layer. Elastic elements (111, 112, 113) of the stability layer approximating the hip flexors, hip extensors and spinal extensors are attached to the load distribution members (102) at the thighs, waist, and shoulders.

Figure 1G:
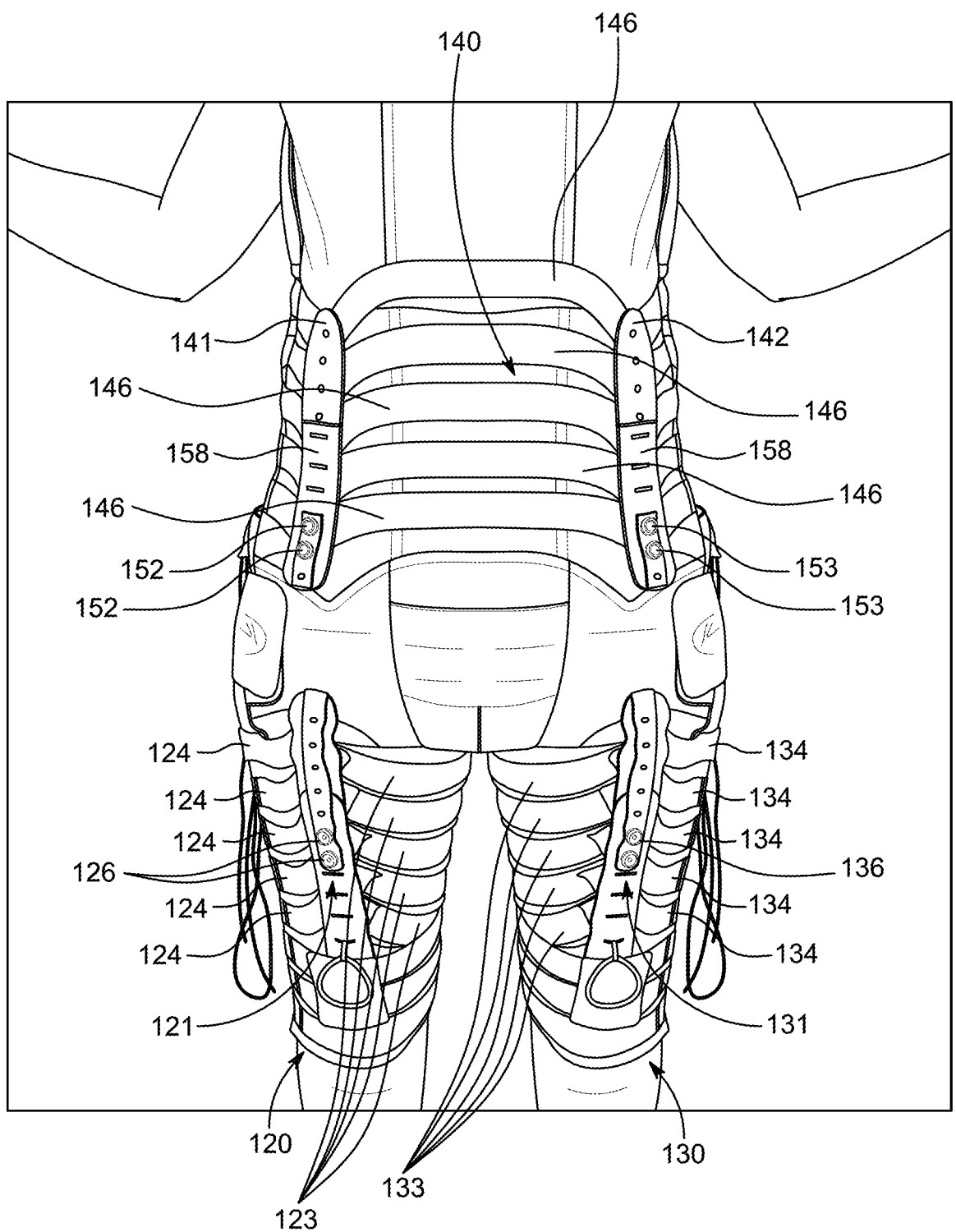
FIGS. 1G-1I show illustrative front, back, and side views, respectively, of the base layer without the presence of the stability or power layers according to some embodiments of the present disclosure.
Figure 1H:
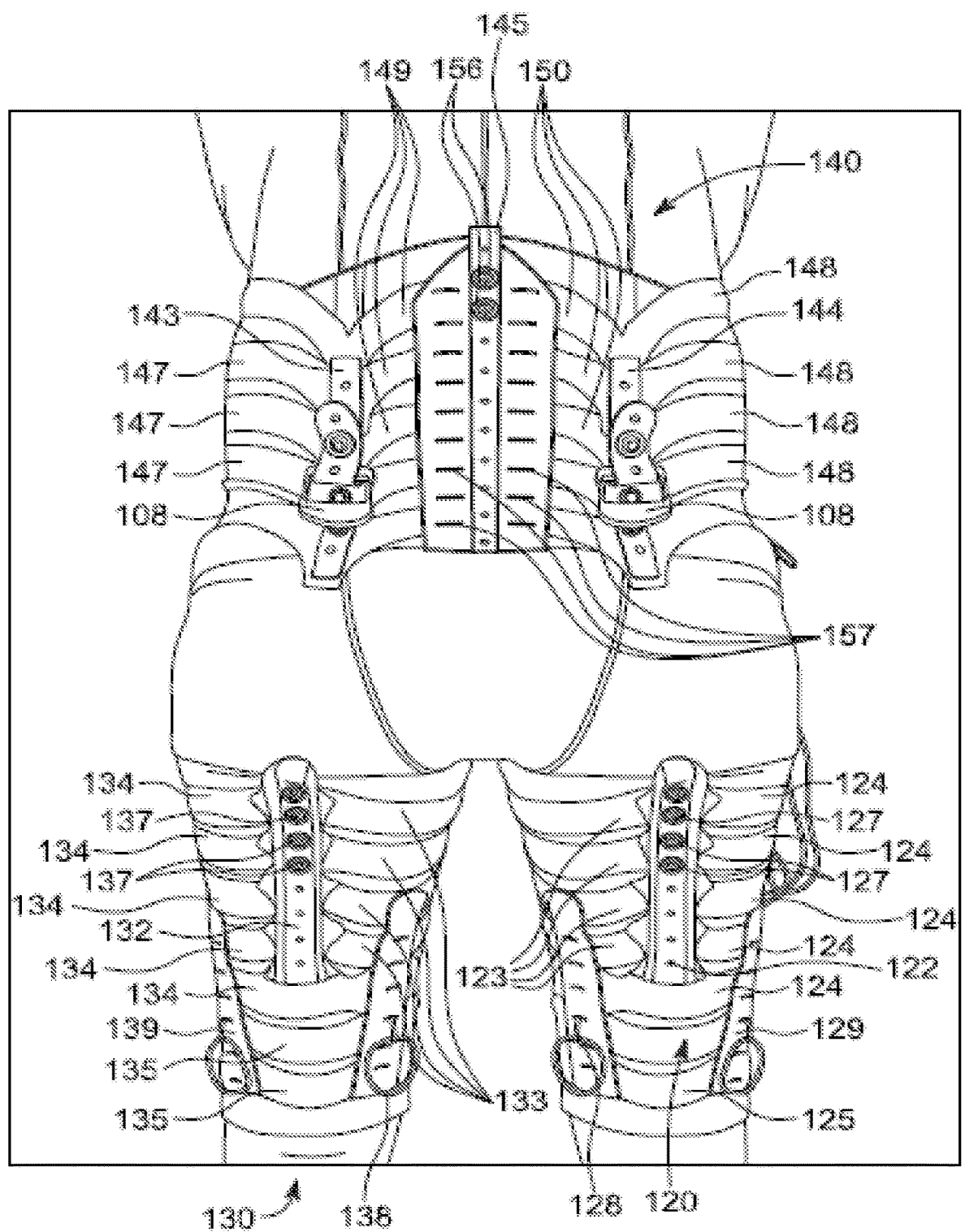
Figure 1I:
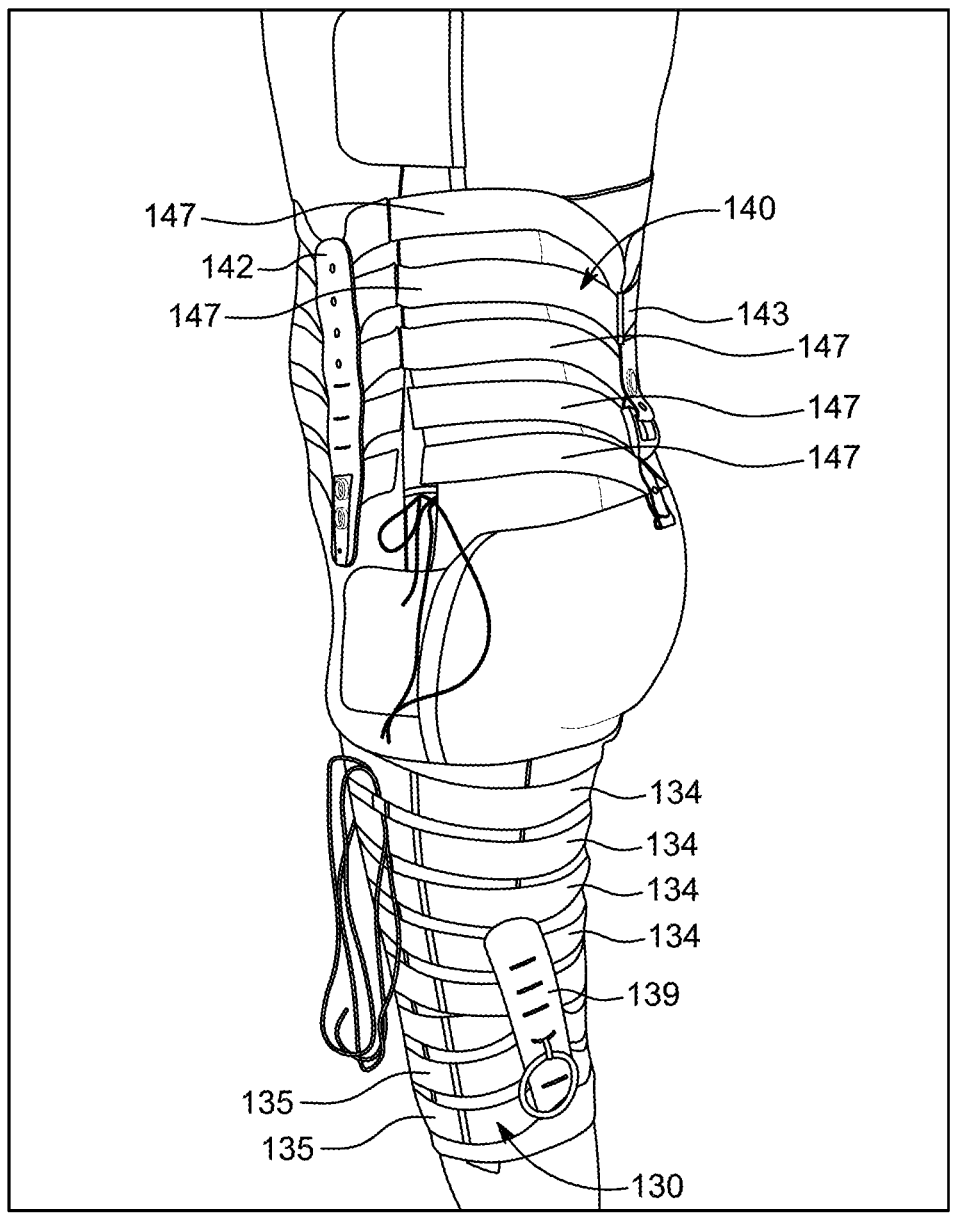

FIGS. 1G-1I show illustrative front, back, and side views, respectively, of the base layer without the presence of the stability or power layers. FIGS. 1G-1I, in particular, show thigh distribution member 120, thigh distribution member 130, and lower torso distribution member 140. Thigh distribution member 120, thigh distribution member 130, and lower torso distribution member 140 are the same as distribution members 102, discussed above, but have been relabeled for further discussion. Thigh distribution member 130 can include stays 131 and 132 that run along the length of the thigh and are attached to a series of straps 133 that span the inside of the thigh and to another series of straps 134 that span the outside of the thigh. When a force (e.g., an upward force in direction of the hips) is applied to stays 131 or 132, the load is transferred through straps 133 and 134. Additional straps, such as straps 135, may encircle the thigh, but are not coupled to stays 131 and 122. Straps 135 may be coupled to other stays such as stays 138 and 139. Some of straps 133 and 134 may be coupled to stays 138 and 139, in addition to stays 131 and 132. When a force (e.g., an upward force in direction of the hips) is applied to stays 138 or 139, the load is transferred through straps. Fasteners 136 and 137 may exist on stays 131 and 132, respectively.

Thigh distribution member 120 can include stays 121 and 122 that run along the length of the thigh and are attached to a series of straps 123 that span the inside of the thigh and to another series of straps 124 that span the outside of the thigh. When a force (e.g., an upward force in direction of the hips) is applied to stays 121 or 122, the load is transferred through straps 123 and 124. Addition straps, such as straps 125, may encircle the thigh, but are not coupled to stays 121 and 122. Straps 125 may be coupled to other stays such as stays 128 and 129. Some of straps 123 and 124 may be coupled to stays 128 and 129, in addition to stays 121 and 122. When a force (e.g., an upward force in the direction of the hips) is applied to stays 128 or 129, the load is transferred through straps 123, 124, and 125. Fasteners 126 and 127 may exist on stays 121 and 122, respectively.

Lower torso distribution member 140 may be distributed around part of the waist, back, and hips of the wearer. Distribution member 140 can include stays 141-145. Straps 146 may be coupled to stays 141 and 142. Stays 141 and 142 may include several slots 158 that can be used to secure FLAs 103 in place. Inclusion of several slots allows the wearer to place an end of FLA 103 at a position that provides the best fit. Stay 145 may also include several slots 157 that can be used to secure FLAs 107 in place. Straps 147 may be coupled to stays 142 and 143, and straps 148 may be coupled to stays 144 and 141. Straps 149 may be coupled to stays 143 and 145, and straps 150 may be coupled to straps 145 and 144. When forces are applied to one or more of stays 141-145, the load is distributed through lower torso distribution member 140. Stays 141 and 142 may include fasteners 152 and 153. Stays 143 and 144 may include adjustment elements 108 and fasteners (not clearly shown as they are obscured by adjustment elements 108). Stay 145 may include fasteners 156.

One of elastic elements 111 may be connected to fasteners 126 and 152, and another one of elastic elements 111 may be connected to fasteners 136 and 153. The inclusion of several fasteners for each stay may provide flexibility and fitting the wearer of the exosuit. Elastic element 112 may be connected to fasteners on each of thigh distribution member 120, thigh distribution member 130, and lower torso distribution member 140. Elastic element 113 may be connected to fasteners on lower torso distribution member 140 and yoke distribution member 160 (shown below in FIG. 1K).

Figure 1J:
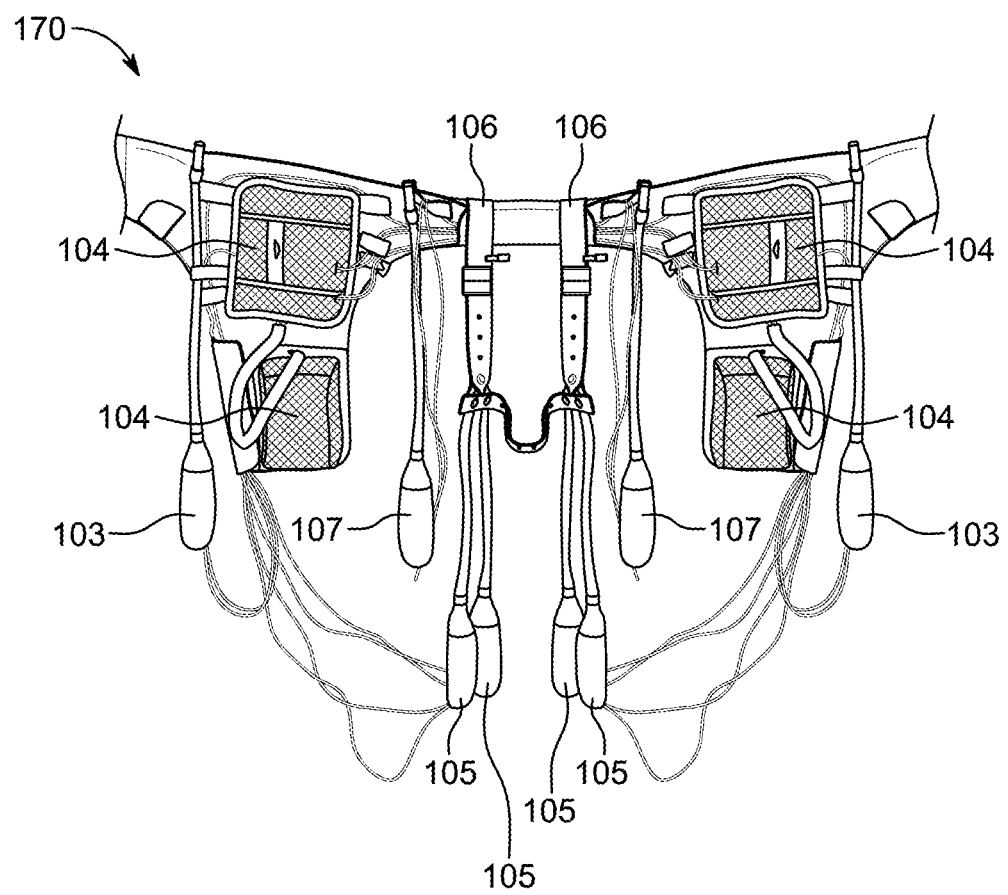
FIG. 1J shows an illustrative chassis strap system constructed to be worn around the lower torso region of the wearer according to some embodiments of the present disclosure.

FIG. 1J shows an illustrative chassis strap system 170 that constructed to be worn around the lower torso region of the wearer and on top of load distribution member 140. Chassis strap system 170 may include electronics 104, tendon elements 106, FLAs 103, 105, and 107. After chassis strap system 170 is dinned by the wearer, FLAs 103 and 105 may be attached to thigh distribution members 120 and 130. One of FLAs 103 may be attached to stays 121 and 141 and the other one of FLAs 103 may be attached to stays 131 and 142. This way, FLAs 103 are attached to two different load distribution members (e.g., distribution members 140/120 and distribution members 140/130). When FLAs 103 are activated, a tension force pulls the thighs and torso together to assist in hip flexor movement. For example, when the left thigh FLA 103 is activated, the tension force pulls on stays 131 and 143 to pull the thigh in a hip flexor movement. The forces on stays 131 and 143 are distributed throughout distribution members 130 and 140.

FLAs 105 may be attached to stays 128, 129, 138, and 139 and tendon elements 106. Tendon elements 106 may be connected to adjustment elements 108. Attaching one end of FLAs 105 to tendon elements 106 enables FLAs 105 to be secured to torso distribution member 140. The positioning of tendon element 106 can be adjusted via adjustable elements 108 to provide the best fit for the wearer. Thus, the left thigh FLAs 105 are attached to stays 138 and 139 and to torso load distribution member 140 via tendon element 106. The right thigh FLAs 105 are attached to stays 128 and 128 and to torso distribution member 140 via tendon 106. When FLAs 105 are activated, they apply a hip extensor assistance movement between torso distribution member 140 and thigh distribution members 120 and 130. When the left thigh FLAs 105 are activated, the tension force generated by these FLAs are distributed through torso distribution member 140 and thigh distribution member 130. When the right thigh FLAs 105 are activated, the tension force generated by these FLAs are distributed through torso distribution member 140 and thigh distribution member 120.

Figure 1K:
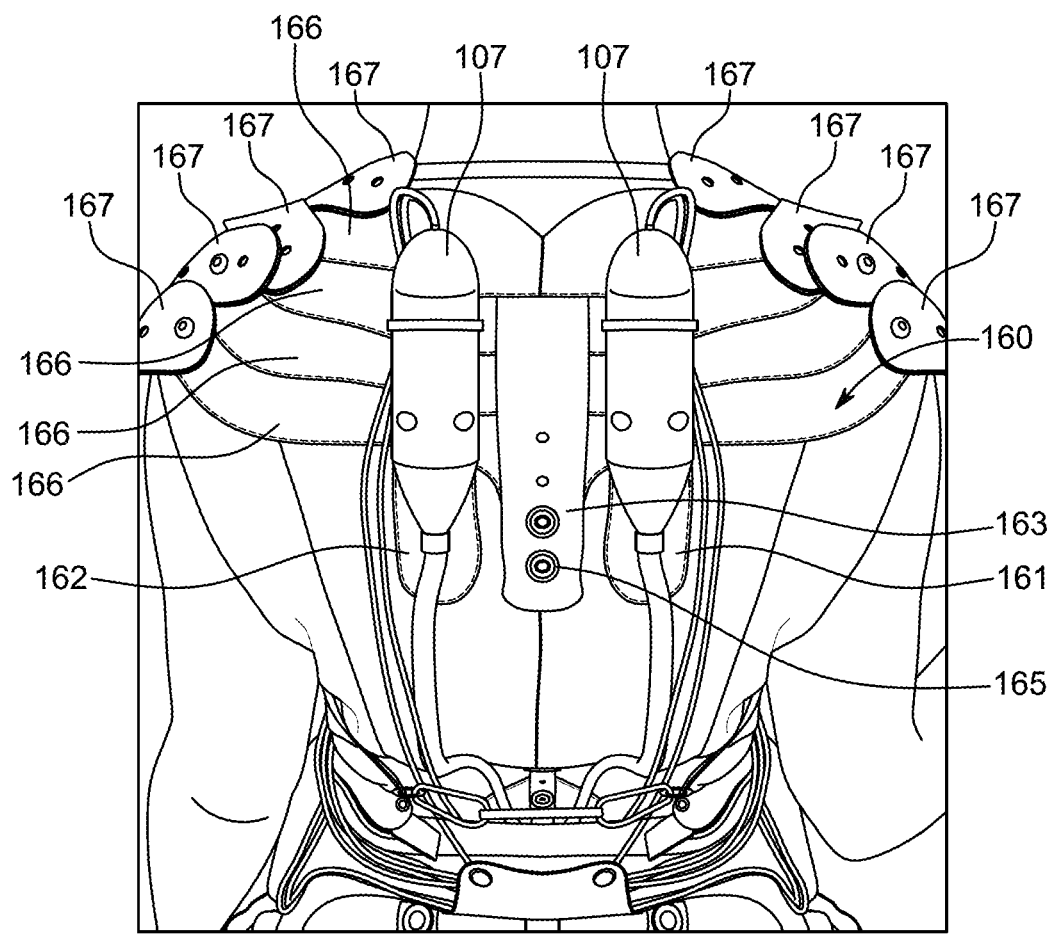
FIG. 1K shows yoke distribution member disposed around an upper torso portion of a user according to some embodiments of the present disclosure.

FIG. 1K shows yoke distribution member 160 disposed around an upper torso portion of a user. Adjustable shoulder harness 109 is attached to the yoke distribution member 160 and torso distribution member 140. Lacing 110 along the sides of the torso and can be adjusted to fit shoulder harness 109 to the wearer. Yoke distribution member 160 can include stays 161-163. Stays 161 and 162 may be coupled to FLAs 107. Stay 163 may include fasteners 165. Fasteners 165 and 156 (FIG. 1H) may be used to secure elastic member 113 (shown in FIG. 1E).

Yoke member 160 can include straps 166 that run along the back of the wearer. Any number of straps 166 may be used, and the embodiment shown in FIG. 1K has 4 such straps. Each of straps 166 may be coupled shoulder harness interfacing straps 167, which connect to shoulder harness 109. Shoulder harness interfacing straps 167 may pivot or move relative to straps 166 to accommodate different sized users.

FLAs 107 can be coupled to stays 161 and 162 of yoke distribution member 160 and to stay 145 of torso distribution member 140. When FLAs 107 are activated, they provide the exosuit with postural support or spinal extension. In particular, when FLAs 107 apply force tension, they pull down on yoke distribution member 160 and pull up on torso distribution member 140. Thus, the load caused by the force tension applied FLAs 107 is distributed across yoke distribution member 160 and torso distribution member 140.

Outerwear (Over-the-Clothes) Assistive Exosuit System

FIGS. 2A-2E illustrate an outerwear assistive exosuit (OAE) system that is intended to be worn over the wearer's clothing according to some embodiments of the present disclosure.

Figure 2A:
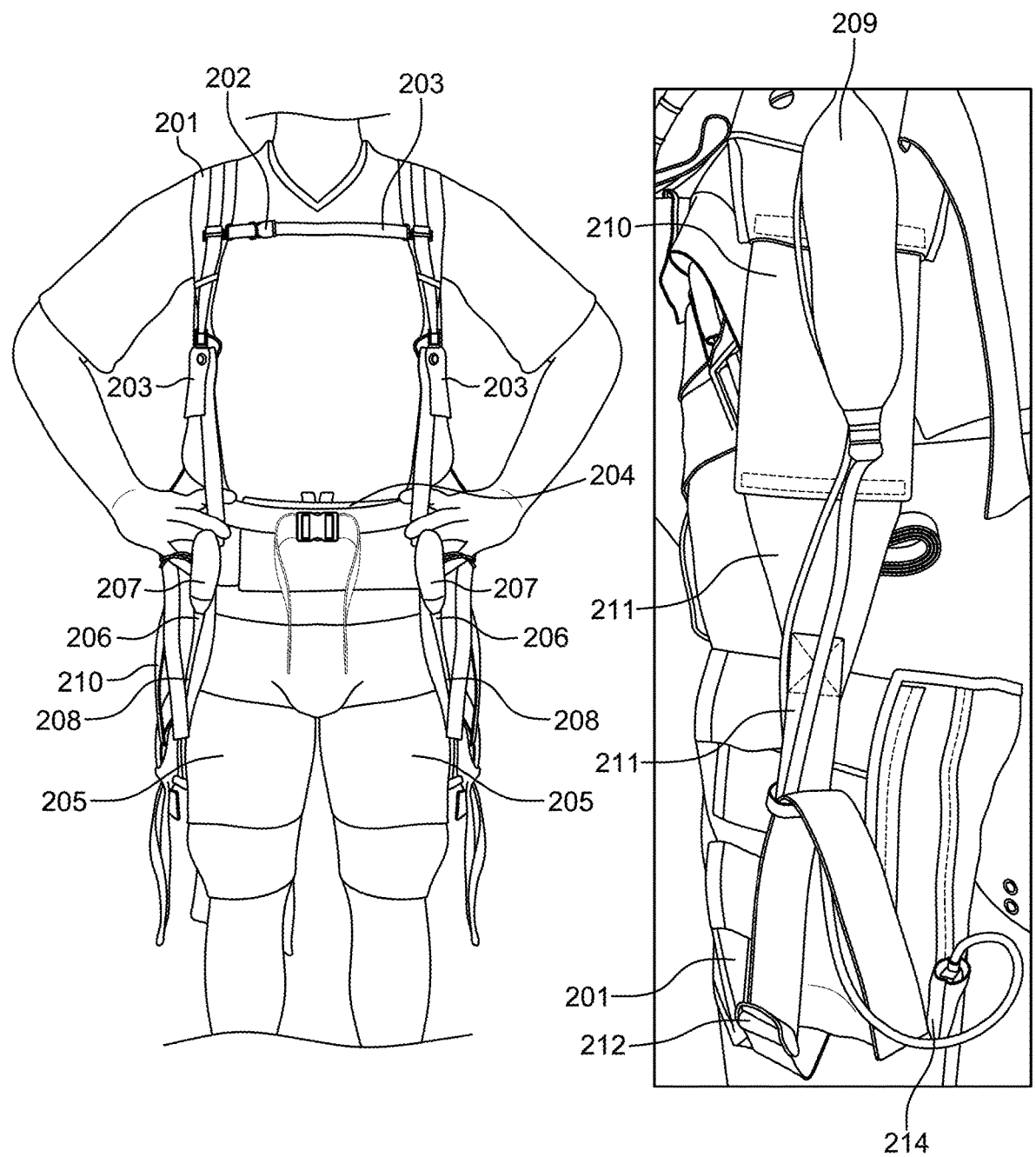
FIG. 2A shows a front view of an assistive exosuit that is to be worn over the wearer's clothing according to some embodiments of the present disclosure.

FIG. 2A shows a front view of the OAE according to some embodiments of the present disclosure. A shoulder harness (201) with cross-straps (202) attaches to the wearer's upper body. Tension lock fittings (203) allow adjustment of the size and tightness of the shoulder harness and cross straps. Load distribution members (204, 205) encircle the wearer's waist and thighs, respectively. FLAs (206) configured as hip flexors attach at the waist and thighs. The FLAs may include a rounded, contoured housing (207) around the motor, transmission and spindle assembly for protection of the components and comfort of the wearer. The twisted strings of the FLAs are housed in braided tubing (208) that protects the strings from abrasion, tangling or snagging. The FLAs may be further enclosed (209) in fabric or other elements of the OAE for cosmetic integration, protection and comfort. Elastic elements (210) are configured in parallel with the FLA, such that they also mimic hip flexors. Webbing (211) connects the elastic elements (210) to an adjustment fitting (212), which is anchored to the Load distribution members at the thigh (205). The webbing (211) acts as a tendon for the FLAs (206) transmitting force to the leg Load distribution members (205) and also acting as a method of shortening and lengthening for wearer height variation. Since the elastic elements (210) and FLAs (206) attach to the lower end of the Load distribution members (205), an internal stay transmits compressive loads back up through the Load distribution members so that the load is evenly distributed across the thigh without rolling the Load distribution member up. This permits use of the full surface of the thigh while still maintaining the stroke length for the FLA, as well as providing conformance to the contours of the wearer's body without pinching or kinking the FLA or power transmission. An IMU is attached to the front of each thigh (214) so that the sensor and controls layer can detect movement of the legs.

Figure 2B:
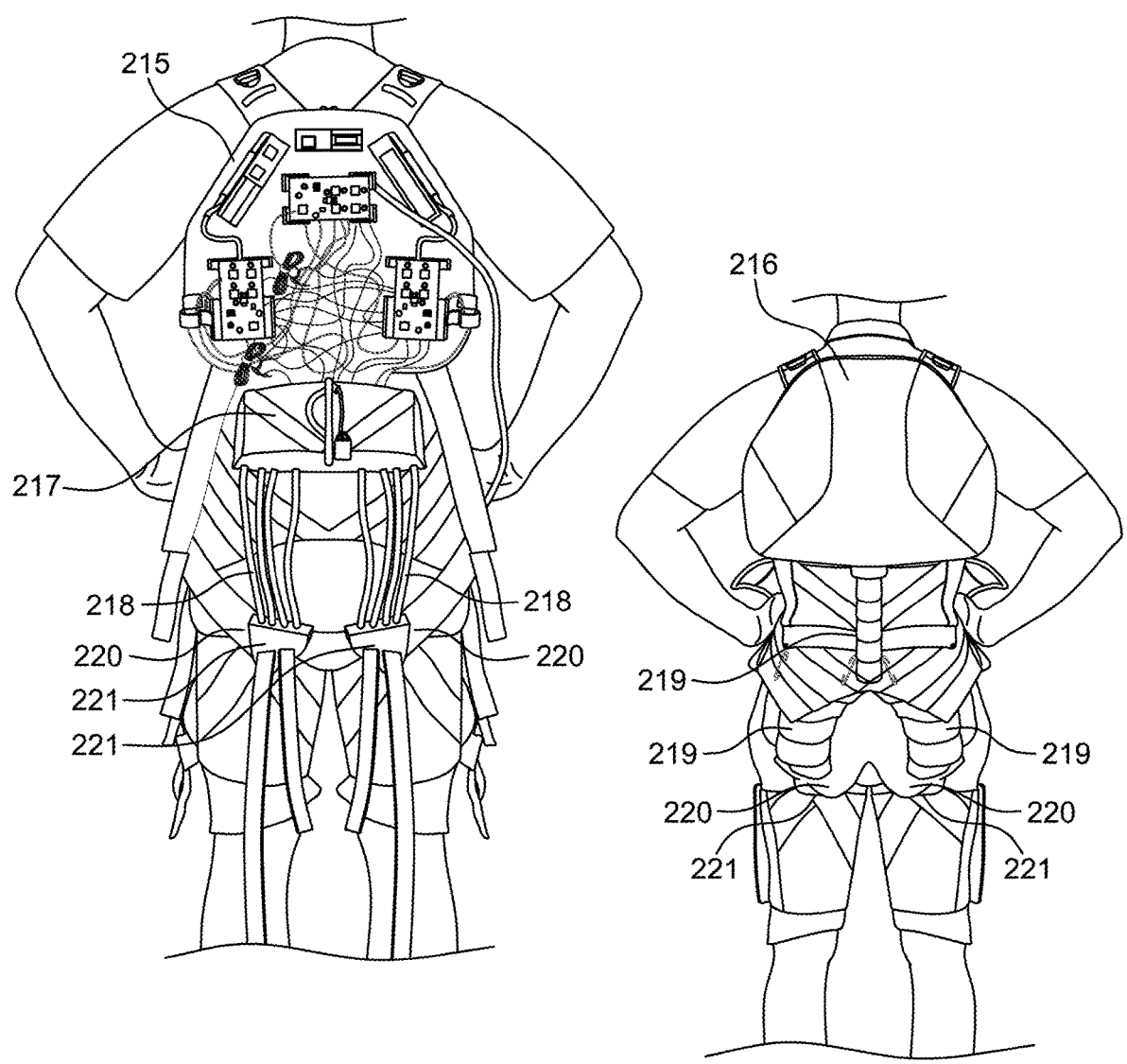
FIG. 2B shows a back view of an assistive exosuit that is to be worn over the wearer's clothing according to some embodiments of the present disclosure.

FIG. 2B shows the back view of an OAE according to some embodiments of the present disclosure. Electronic components (215) including batteries, circuit boards and cables are mounted in a backpack type area of the upper back. The electronics are typically covered with an enclosure or fabric cover (216) for protection and aesthetics. Two FLAs (217) configured in parallel traverse the lumbar spine, mimicking spinal extensor muscles. Four FLAs (218) configured in parallel attach between Load distribution members at the waist and each thigh, mimicking hip extensors or gluteal muscles. Fabric coverings (219) hide the FLAs for protection and aesthetics. The coverings (219) may be pleated, reticulated or compliant to accommodate length changes of the FLAs. Elastic elements (220) of the stability layer are arranged in parallel with the FLAs. The elastic elements (220) and FLAs (218) attach to the Load distribution members via adjustable interconnections (221) allowing the size or tension to be adjusted to the individual wearer, with webbing tendons (211) as described above providing the range of adjustment as well as conformance to the wearer's body.

Figure 2C:
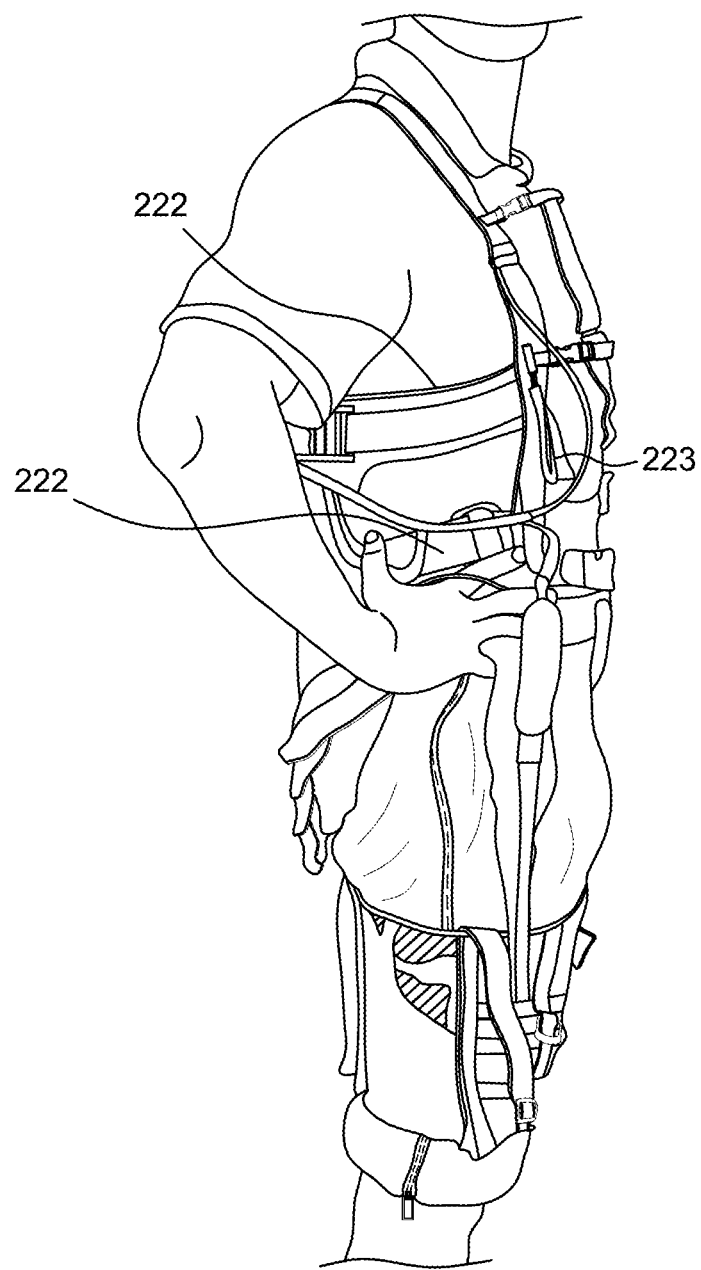
FIG. 2C shows a side view of an assistive exosuit that is to be worn over the wearer's clothing according to some embodiments of the present disclosure.

FIG. 2C shows a side view of the OAE according to some embodiments of the present disclosure. One or more side bands (222), five in this example, connect between the front and back of the torso portion of the OAE. The one or more side bands are adjustable to accommodate the wearer's size. Tightening the side bands grips the wearer's torso to distribute loads across the suit, effectively functioning as a Load distribution member. An easily accessible emergency stop switch (223) is located on the wearer's chest.

Figure 2D:
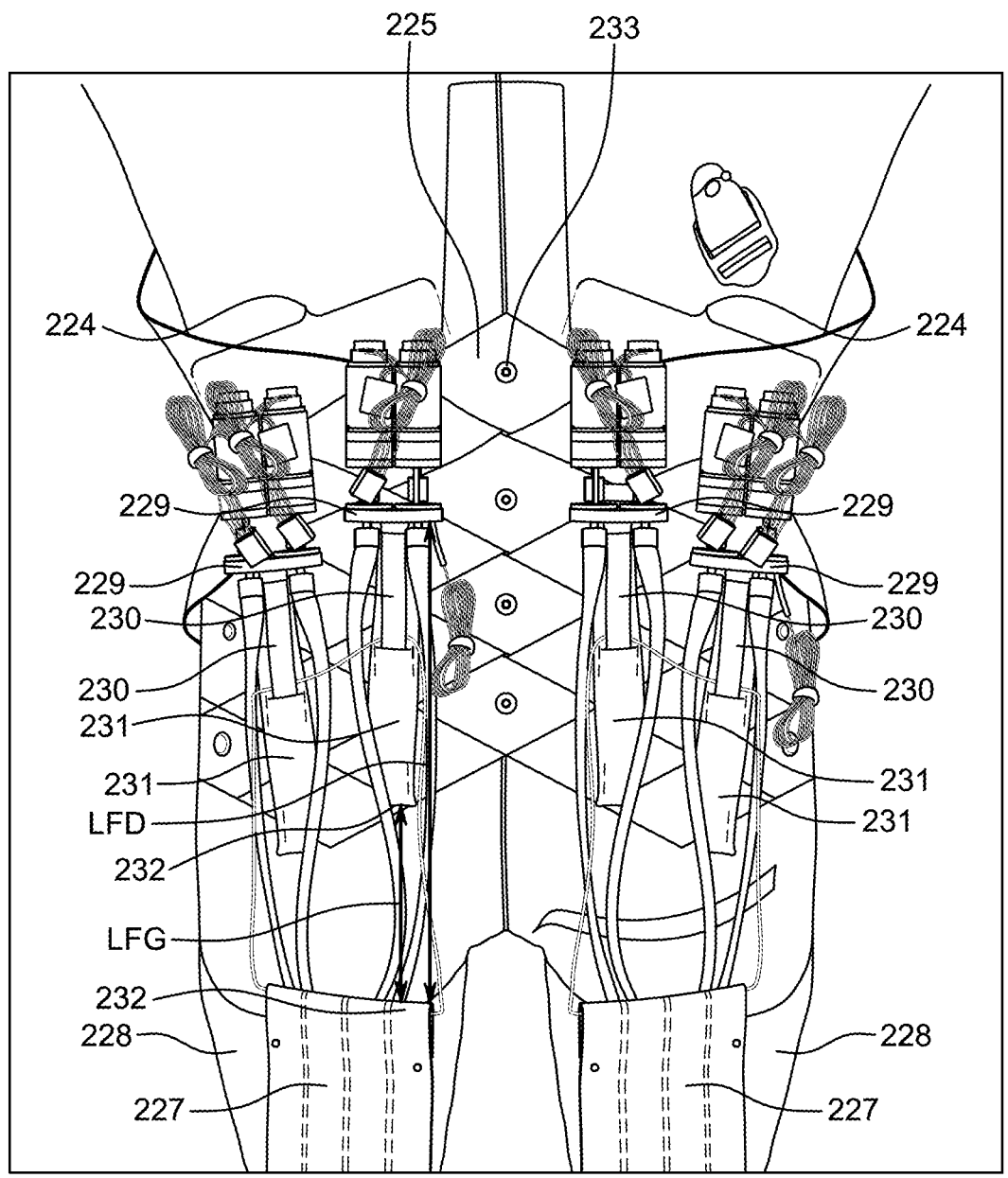
FIG. 2D shows a detail view of an assistive exosuit that is to be worn over the wearer's clothing, including Load distribution member with pivots and compressive elements attached to a torso according to some embodiments of the present disclosure.

FIG. 2D shows a detailed back view of components of the OAE according to some embodiments of the present disclosure. The waist Load distribution member (225) comprises segments of webbing arranged in a biaxial braid with rivets (233) at the intersections. This arrangement allows the Load distribution member to both conform to the wearer's waist, as well as constrict and grip the wearer's trunk as loads are applied to the attachment points (232). Two groups of four FLAs (224) are arranged in parallel, attached to the load distribution members at the waist (225). Each group of FLAs is attached at the opposite end to the webbing tendons (227) that transmit the FLA forces to Load distribution members at the thighs (228). Within each group of four FLAs (224), pairs of drives are yoked together with brackets (229) mounted on stays (230), which insert into sleeves (231) on the base layer Load distribution member. The stays transmit compressive loading between the FLAs and Load distribution members, in order to allow optimal, independent placement and orientation of the FLAs and Load distribution members. In this example, the optimal situation of the Load distribution members at the waist and thighs results in the distance (LFG) between the attachment points (232) of the Load distribution members being much shorter than the optimal free length (LFD) of the FLAs. The stays (230) permit use of FLAs with an optimal length (LFD), while transmitting the FLA forces to optimal attachment points (232) of the Load distribution members.

Figure 2E:
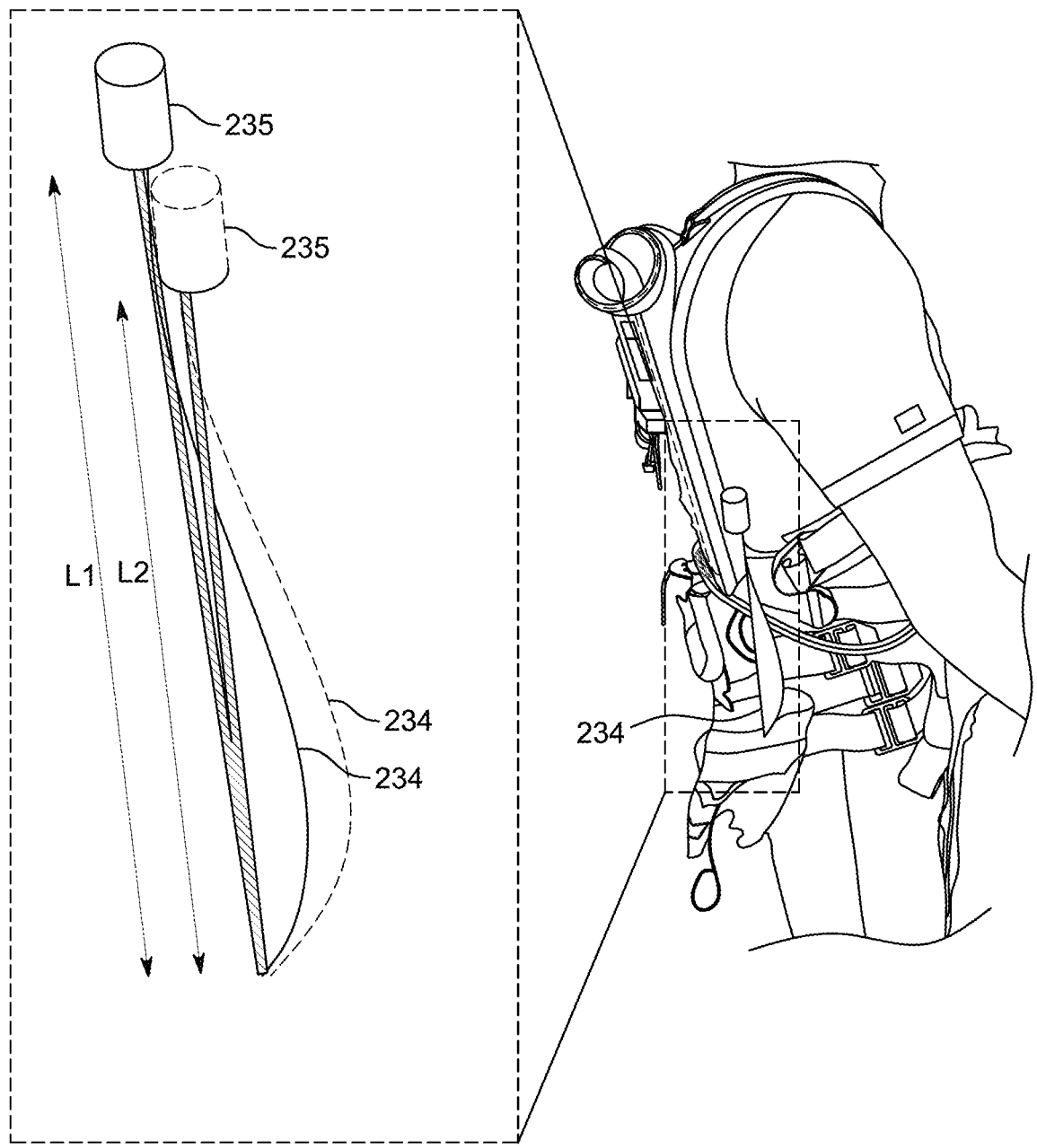
FIG. 2E shows a detail view of a postural support subsystem of an assistive exosuit that is to be worn over the wearer's clothing according to some embodiments of the present disclosure.

FIG. 2E illustrates a lumbar or postural bolster as implemented in the OAE according to some embodiments of the present disclosure. The bolster comprises a semi-rigid panel (234) that follows the contour of the lower back. When the spinal extensor FLA (235) is actuated, it contracts and shortens from a first length (L1) to a shorter length (L2). The shorter length (L2) increases the curvature (arrow) of the bolster panel (234), providing increased lumbar and postural support. The bolster is seated in a pocket in the base layer, with a tongue feature that transversely distributes the bolster forces throughout the Load distribution members along the spine and trunk.

Figure 2F:
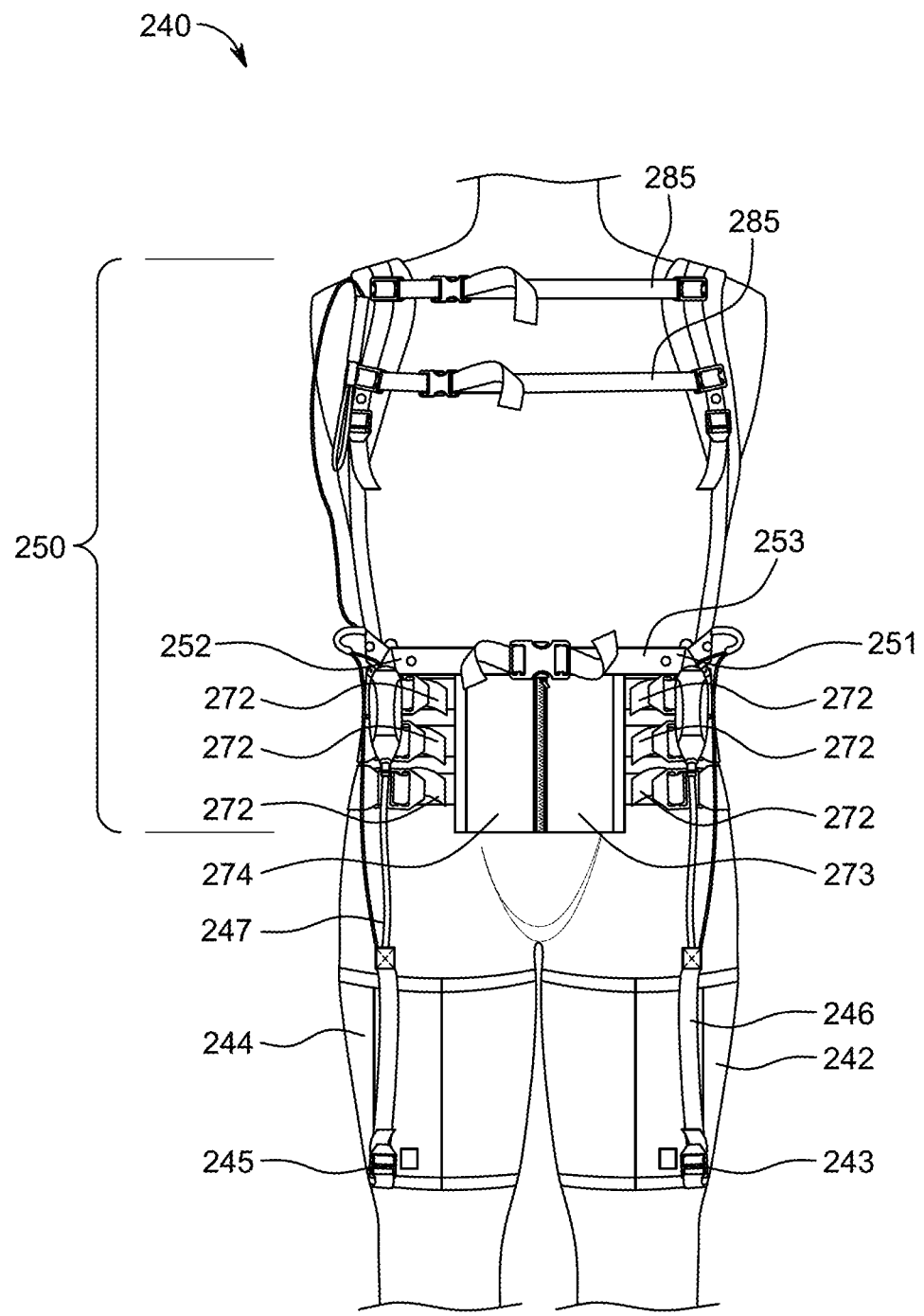
FIGS. 2F-2J illustrate another outerwear assistive exosuit (OAE) system that is intended to be worn over the wearer's clothing according to some embodiments of the present disclosure.
Figure 2G:
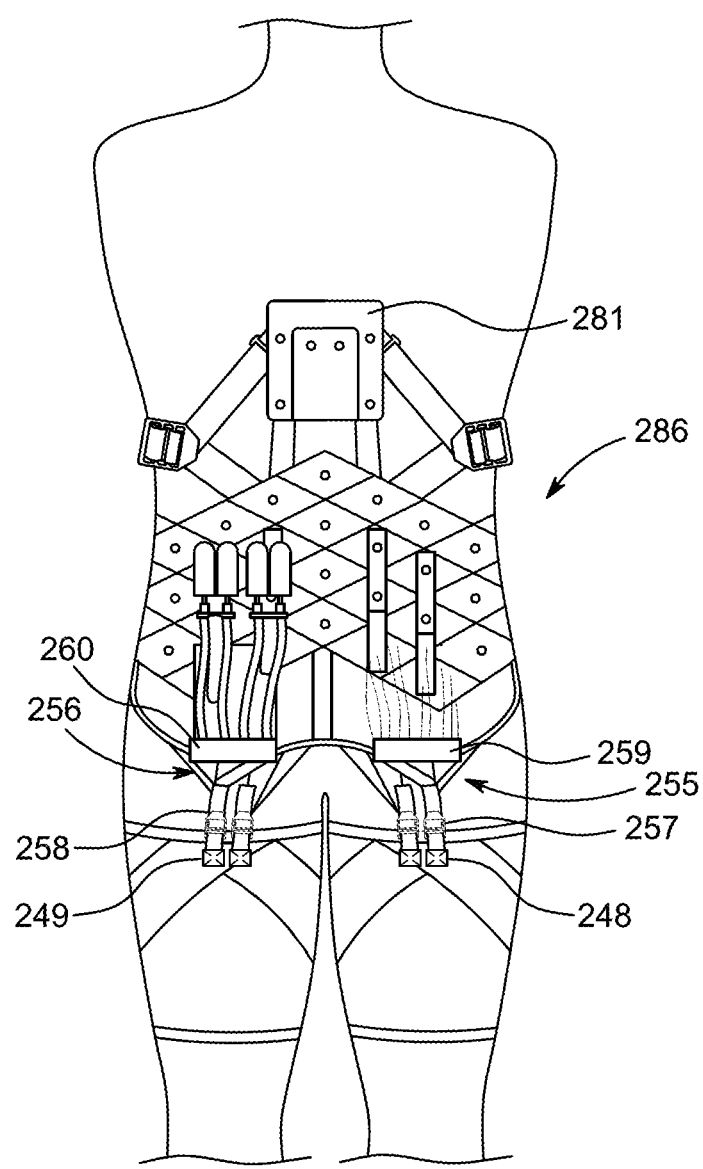
Figure 2H:
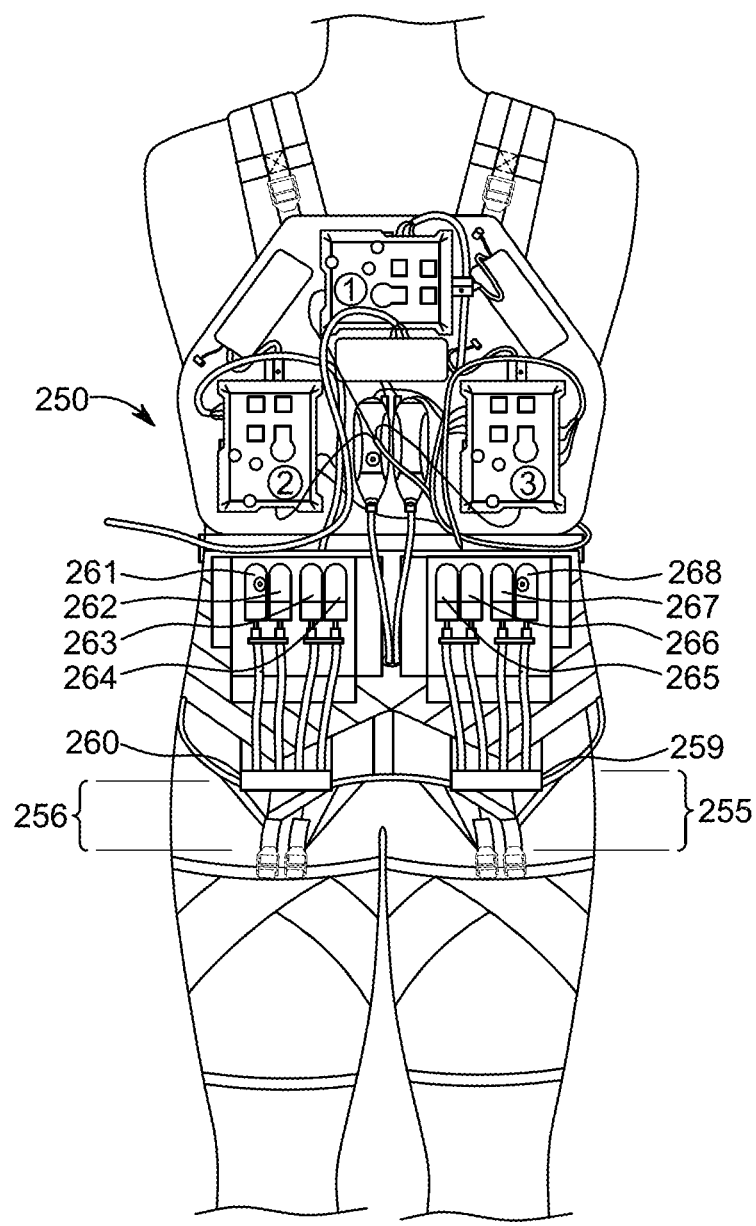
Figure 2I:
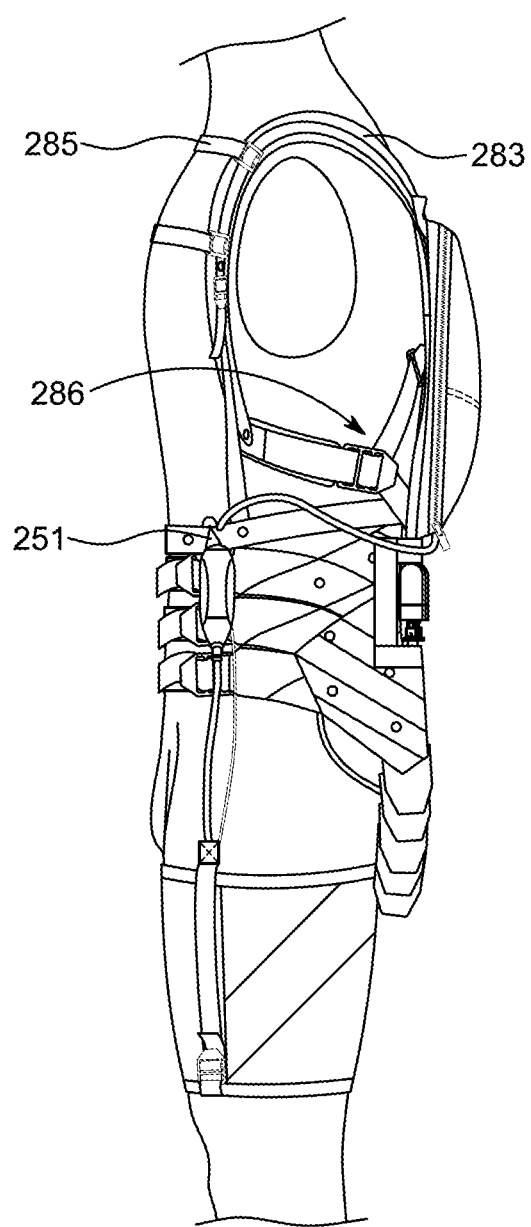
Figure 2J:
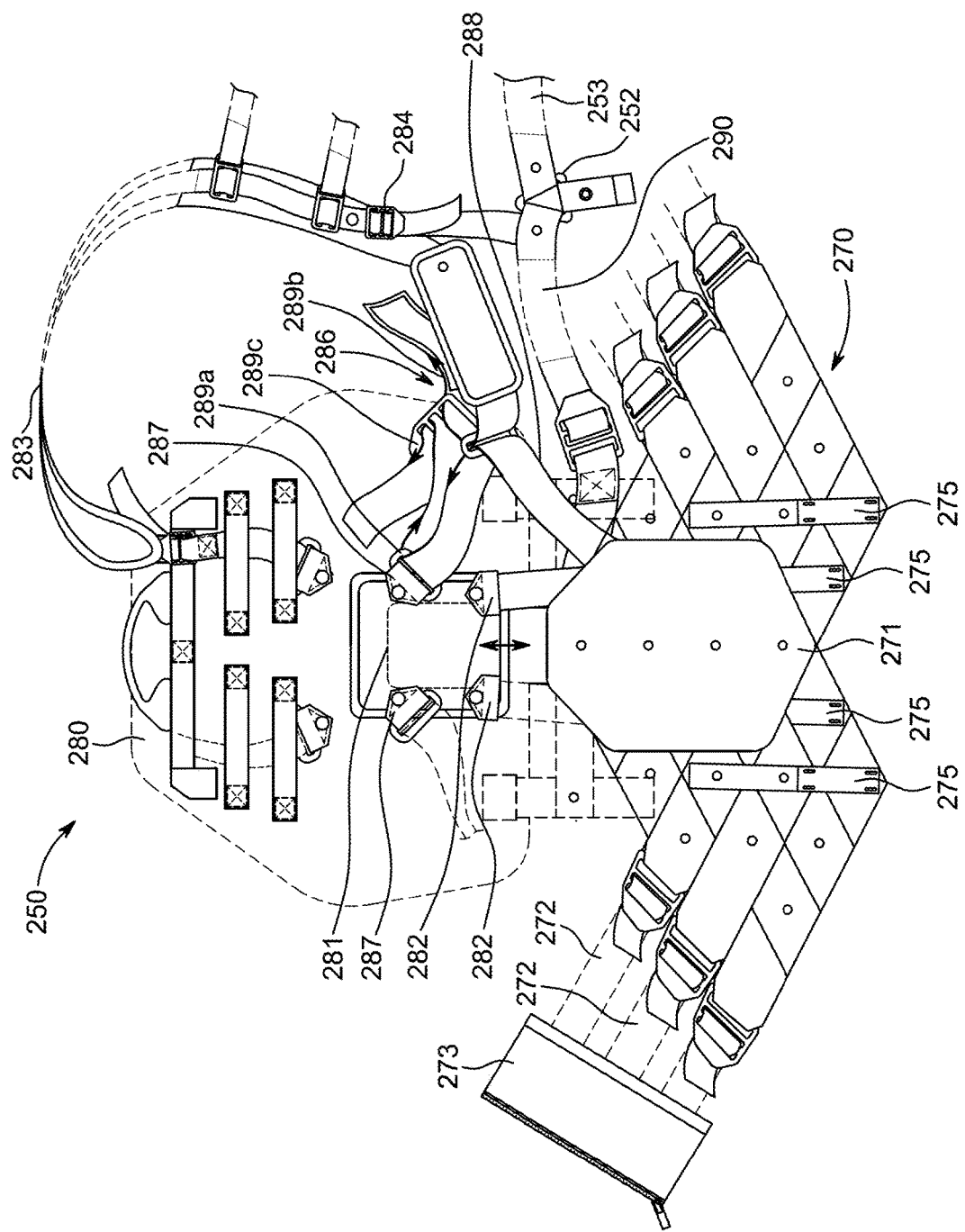

FIGS. 2F-2I illustrate another outerwear assistive exosuit (OAE) system 240 that is intended to be worn over the wearer's clothing according to some embodiments of the present disclosure. FIG. 2F shows an illustrative front view of exosuit 240. FIG. 2G shows a back view of a partially assembled exosuit 240. FIG. 2H shows a back view of an assembled exosuit 240 that does not have any coverings present. FIG. 2I shows a side view of an assembled exosuit 240 that has coverings present. FIG. 2J shows torso support system 280. Each of FIGS. 2F-2J will be discussed collectively.

Exosuit 240 can include thigh load distribution members 242 and 244, and torso support system 250. Thigh load distribution members 242 and 244 are constructed to fit around the thighs of the user wearing exosuit 240 and each include attachment elements 243 and 245 for securing an end of hip flexor FLAs 246 and 247 in place. The other end of hip flexor FLAs 246 and 247 may be attached to hip flexor anchoring system 251 and 252, respectively, of torso support system 250. Thigh load distribution members 242 and 244 can include attachment elements 248 and 249 that can be secured to extensor anchoring systems 255 and 256. Extensor anchoring systems 255 and 256 can include straps 257 and 258 that are coupled to attachment elements 248 and 249. Straps 257 and 258 can be adjusted to best fit the user. Extensor anchoring systems 255 and 256 can also include anchoring elements 259 and 260 for securing an end of hip extensor FLAs 261-268 in place.

Torso support system 250 can include scissor load distribution member 270, spine hub 271, adjustable straps 272, belly bands 273 and 274, FLA stays 275, support structure 280, lumbar pocket 281, shoulder straps 283, shoulder adjustment elements 284, chest adjustment straps 285, and chest depth strap systems 286. Scissor load distribution member 270 is coupled to belly bands 273 and 274 via adjustable straps 272. Belly bands 273 and 274 can be attached together, for example, via a zipper or other coupling device. Belly bands 273 and 274 may be a tri-zoned (or triple layered) graduated pressure packet that focuses load below the natural waist of the user and also applies pressure above the natural waist (e.g., 1-4 inches or 2 inches above). The tri-zoned construction of belly bands 273 and 274 enable the bands to apply comfortable transverse abdominal pressure to the user. A top portion of bands 273 and 274 may be constructed from a relatively soft elastic material. A middle portion of bands 273 and 274 may be constructed from a material having a first elastic stiffness that is greater than a stiffness of the first portion. A bottom portion of bands 273 and 274 may be constructed from a material having a second elastic stiffness that is greater than the first elastic stiffness. Thus, by varying the stiffness of each portion belly bands 273 and 274, a graduated change in stiffness is provided, but not so stiff that no part of the bands 273 and 274 does not stretch.

Scissor load distribution member 270, in combination with straps 272 and belly bands 273 and 274 is operative to distribute forces around the body of the user when hip extensor FLAs 261-268 are applying their tension force. One end of the FLAs 261-268 (e.g., such as the motor) may be coupled to stays 275 and the other end of FLAs 261-268 are coupled to extensor anchoring systems 255 and 256. Scissor load distribution member 270 is constructed with a series of pivoting unions that bend, flex, and/or scissor (about the pivots) in response to user movement or FLA 261-268 activation. Stays 275 may be positioned on load distribution member 270 such that they load member 270 near the hip of the user.

Spine hub 271 may be coupled to load distribution member 270 and to lumbar pocket 281 via attachment points 282. Spine hub 271 may be referred to as a lumbar dreidel because it has a cross-section of a top. Spine hub 271 is operative to support weight of torso support system 250, including all components. It does this by driving the FLA forces and weight of system 250 into load distribution member 270. Spine hub 271 can be rigid structure that can provide lumbar support to the user. When spine hub 271 is pulled closer to load distribution member 270, the rigidity of the structure can place pressure above and below the lumbar curve of the user, while simultaneously enabling the user to maintain the curve.

Lumbar pocket 281 may be relatively rigid material that distributes loads of the lumbar FLAs into spine hub 271 and scissor load distribution member 270. In addition, lumbar pocket 281 may be mounted to structure 280 and thereby enables structure 280 to move back and forth (in the same direction a user moves his/her back forward and backwards with respect to the hips). Lumbar pocket 281 may be coupled to chest depth strap systems 286 via attachment points 287. FLAs (shown in FIG. 2H) can be coupled to lumbar pocket 281 and to either spine hub 271 or scissor load distribution member 270. These FLAs may be provide spinal extensor assistive movement.

Chest depth strap systems 286 can exhibit a V shape that enables structure 280 to remain close to the user's back when the user is moving around, and in particular, while bending forward. Chest depth strap systems 286 can include strap 288 that is coupled to a shoulder strap 283 and scissor load distribution member 270. Strap 288 runs through rings 289a, 289b, and 289c. The combination of rings 289a, 289b, and 289c, strap 288, and shoulder strap 283 enables structure 280 to move in concert with the user's back.

Flexor load strap 253 may exist between hip flexor anchoring system 251 and 252. Flexor load strap 253 may have a buckle for easy donning and doffing. Strap 290 is attached to hip flexor anchoring system 252 and scissor load distribution member 270 (or spine hub 271). The combination of straps 253 and 290 and system 252 enable forces created by flexor FLA 247 to be transversely distributed into load distribution member 270 and thigh load member 244. A strap similar to strap 290 may be attached to hip flexor anchoring system 251 and scissor load distribution member 270 (or spine hub 271).

Figure 3:
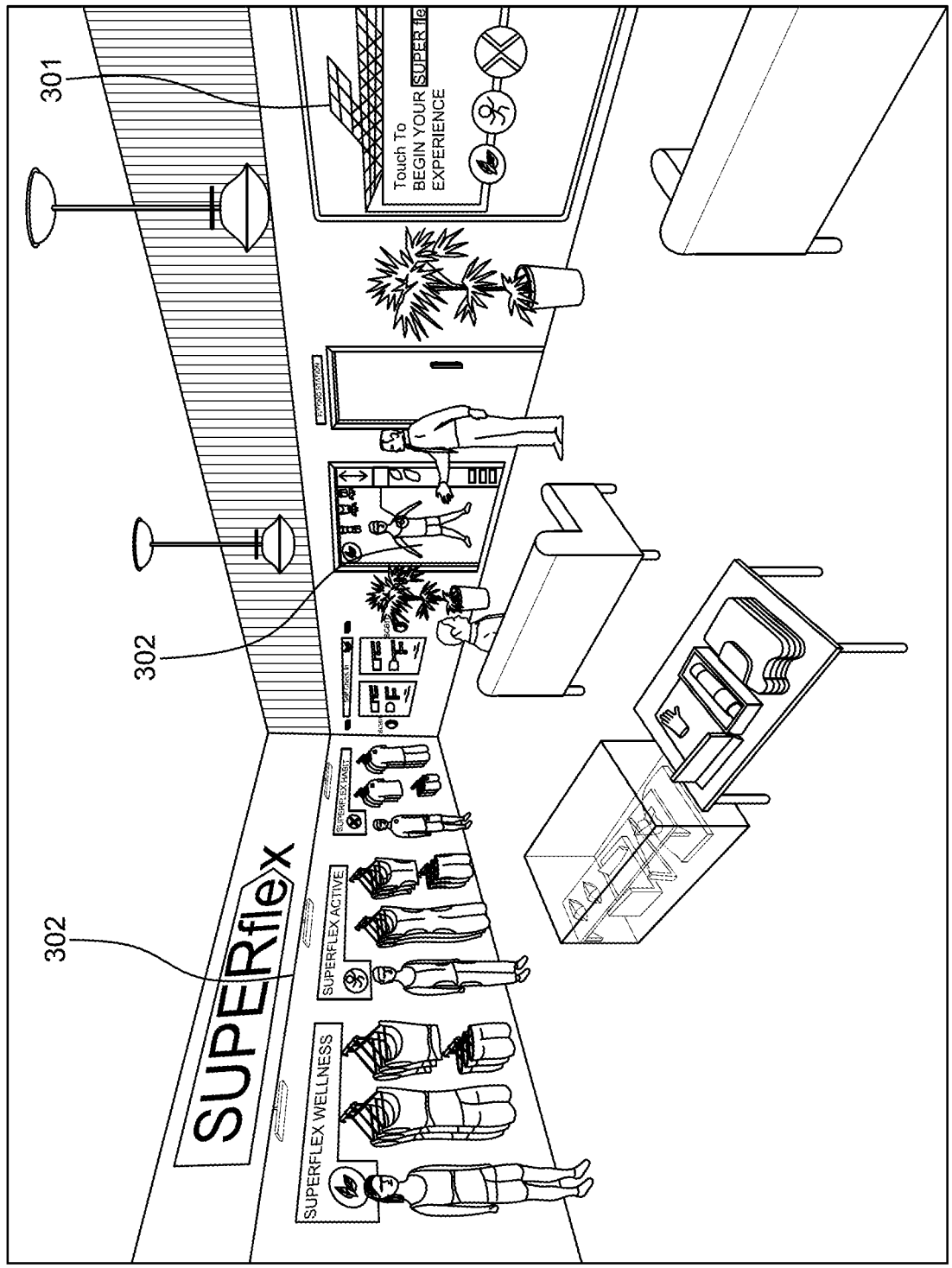
FIG. 3 shows a studio retail or service setting according to some embodiments of the present disclosure.

FIG. 3 shows a retail and customer service setting for the exosuit system according to some embodiments of the present disclosure. In come embodiments, the retail and customer service setting may also be described as a studio. A touchscreen display (301) provides an interactive setting for a wearer to initiate configuration of the suit, such as whether the purpose of the suit is for health/wellness, sports/activity, or other habit/lifestyle purposes. Several exosuits and exosuit components are on display (302). These may be "off-the-shelf" suits and components to configure a suit that is appropriate for the wearer, which may include different shapes or sizes to accommodate for individual wearers of different anthropometry, biomechanics or kinematics. The suit configured with these components may either be a provisional suit used to optimize a custom suit for the wearer, or they may represent the final suit. A representative, sales associate, or technician is shown interacting with a wearer (302) to configure and optimize an exosuit, as well as train the wearer in its operation. Each layer of the exosuit may incorporate some adaptation (customization and optimization). The base layer can be adapted to the wearer's size, comfort requirements, and other specific aspects of the desired use, such as whether it is to be worn over or under the wearer's clothing. The stability layer can be adapted for the appropriate amount of stability to be provided to different parts of the body, based on the wearer's physical characteristics and expected activities. Likewise, the power layer can be adapted to provide the amount of assistance desired for different parts of the body in different activities. The length, speed, and strength of the FLA powered actuators may be selected or adjusted to optimize these parameters. The wearer may perform a specific set of activities so that the sensor and controls layer can calibrate itself and adapt to the wearer's patterns of movements.

Figure 4:
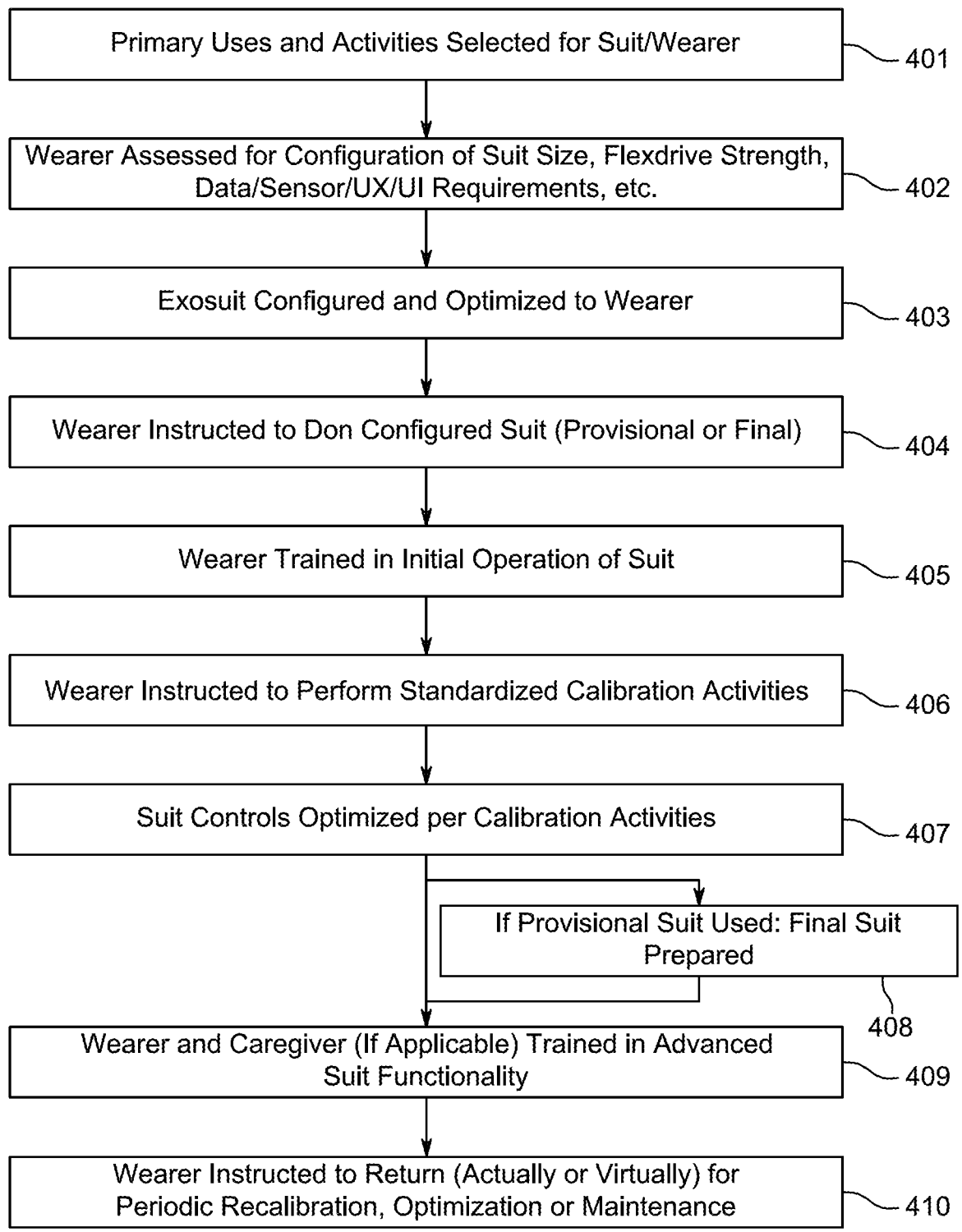
FIG. 4 is a flowchart of a process for providing an assistive exosuit system according to some embodiments of the present disclosure.

FIG. 4 outlines a process for adapting the assistive exosuit to a wearer according to some embodiments of the present disclosure. In some embodiments, the process can be modified by, for example, having steps combined, divided, rearranged, changed, added, and/or removed. This process may be integral to the retail and service experience described above. First, with input from a wearer or their assistant (e.g. companion, caregiver, or anyone else assisting the wearer in obtaining the exosuit), the primary uses and activities that the suit can be intended to assist (401) are selected. The wearer is then assessed for configuration of the exosuit components and parameters such as size, powered actuator/FLA strength and speed, requirements of the sensors and controls layer, and user interface (402). This may also include identification of the wearer from a group of body types based on their general proportions. An exosuit is then configured, optimized to the wearer (403). The wearer can then be instructed to don (put-on) the configured exosuit, which may be either a provisional or final suit that the wearer can use (404). The wearer can then be trained in the initial operation of the suit (405), and instructed to perform standardized activities (406) to optimize and calibrate the sensors and control layer, as well as confirm that the configuration is appropriate (407). If a provisional suit was initially used, the final suit can then be prepared (408). The wearer, as well as a caregiver or companion, if applicable, can then be trained in advanced suit functionality (409). The wearer may be instructed to return to the retail or service center periodically or as-needed for re-calibration, optimization or maintenance of the suit (410), which may be performed on-site, or virtually through remote connections to the suit. Remote connections to the suit may additionally enable a service center to monitor status of the suit, remotely upgrade software, or notify the wearer if service is needed. In one embodiment, the process described above is performed by a one or more computational systems or databases. In another embodiment, the process described above is performed by providing a combination of training, collateral, instrumented or computational systems, or other services, by a manufacturer, distributor, franchise or licensee.

Figure 5:
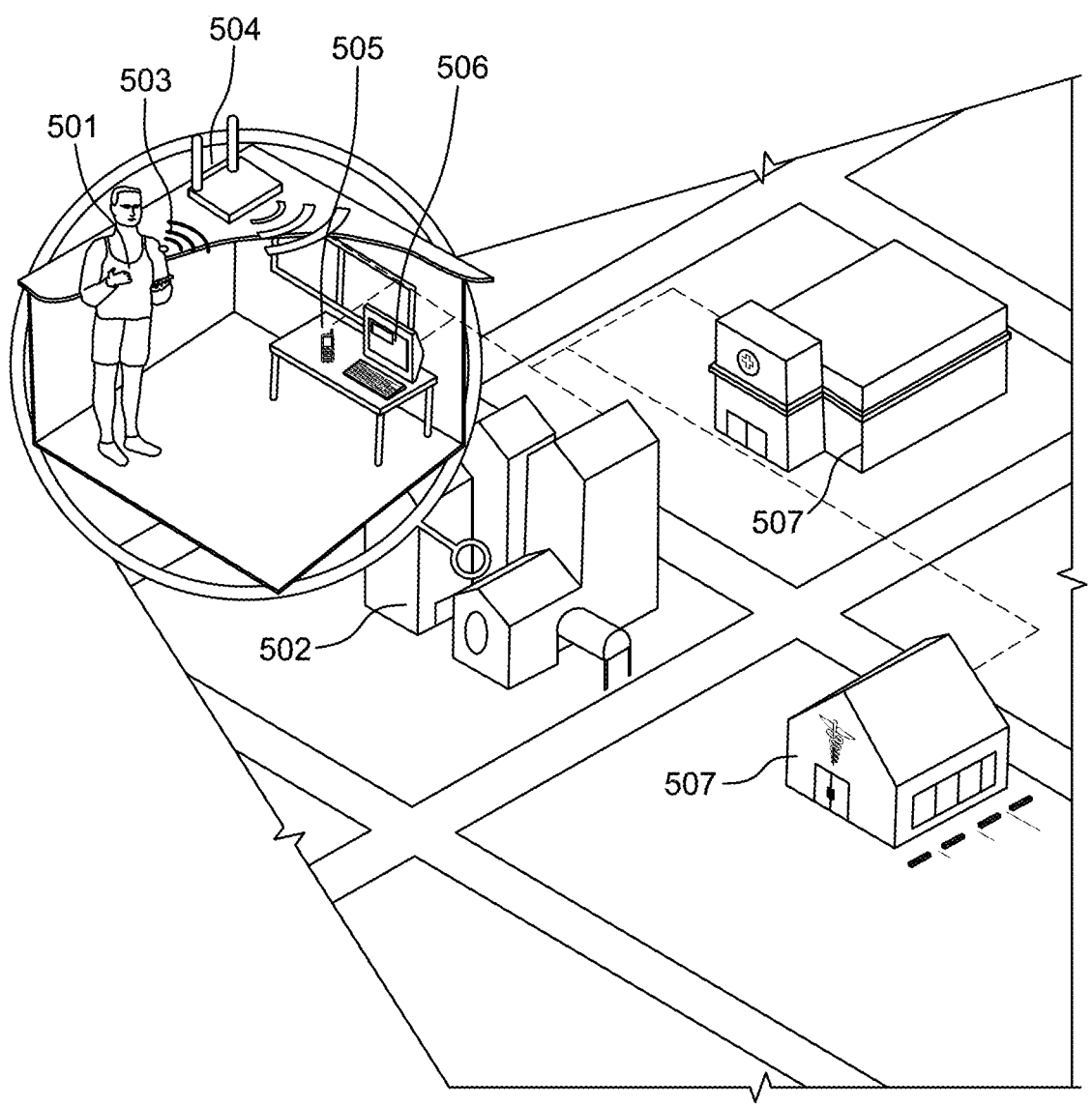
FIG. 5 shows a platform and communication network for an assistive exosuit system according to some embodiments of the present disclosure.

FIG. 5 shows an example assistive exosuit system platform incorporating a communication network according to some embodiments of the present disclosure. As shown, a wearer with an assistive exosuit (501) is at large in the community or a residence (502). A wireless communication link (503) is established between the exosuit and a network, such as a cellular network or home wireless internet connection (504). The network connection enables connection to a personal electronic device such as a tablet or smartphone (505) or PC (506). These can allow the wearer, their companion or caregiver to adjust configurations of the suit (particularly the sensors and controls layer), as well as monitor data related activity levels, the wearer's health, etc. The network connection also enables monitoring and control by one or more remote centers (507) such as a clinical office or service center.

The exosuit system may include other communication systems such as Bluetooth or radio-frequency identification (RFID) that allow communication with devices or systems in close proximity to the suit or wearer. These features may enable assistive or lifestyle convenience functionality such as digital identification of the wearer. In one example, the exosuit system is able to confirm the identity of the individual wearer by detecting unique characteristics of the wearer through the sensors and control layer. The individual characteristics may include patterns of movement such as gait or cadence, body size or morphometry, forces sensed by the suit, and the like. The exosuit system may then verify the wearer's identity to other system such as personal electronics, internet and computer log-ins, banking equipment (ATMs, retail payment systems, etc.), home security systems, door locks, automobile locks and ignition systems, etc. Communication links such as Bluetooth can enable direct communication with electronic devices such as smartphones, tablets and PCs without connection through the broader internet. These connections may be used for functionality as described above.

Figure 6A:
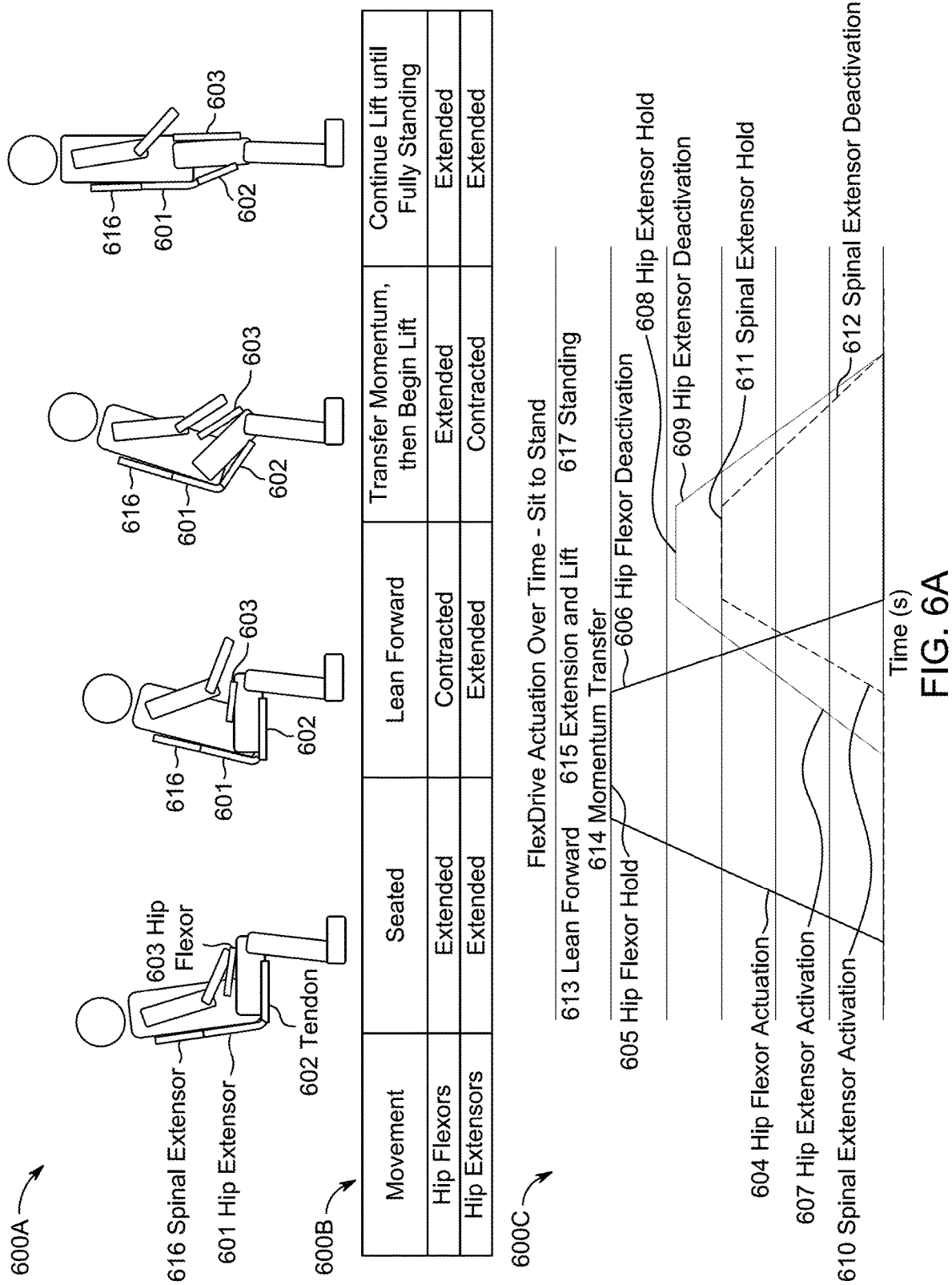
FIG. 6A shows a motion profile for a sit-to-stand activity according to some embodiments of the present disclosure.

Pre-programmed activity or motion profiles enable the sensors and controls layer to actuate components of the power layer for specific activities. While the activity/motion profiles are generally pre-programmed, they may be calibrated or adapted to individual users as described previously. In the following examples, actuators are typically identified by the corresponding muscle groups (e.g. hip flexor, hip extensor, or spinal extensor). Continuing the muscle analogy, actuation of the FLAs corresponds to transition to a contracted state; while deactivation corresponds to transition to an extended state. The motion profiles discussed below in connection with FIGS. 6A-6I may be implemented in an exosuit including several sensors, several load distributing members, and several FLAs that are coupled to and operative to apply forces between the load distributing members such that the exosuit provides assistance in one or more of spinal extensor, hip extensor, and hip flexor muscle movements FIG. 6A illustrates a sit-to-stand activity/motion profile according to some embodiments of the present disclosure. The motion and actuation of the FLAs or powered actuators of the power layer are illustrated in schematic (600A), tabular (600B), and graphical (600C) format. In one example, the hip flexor (603) is actuated to lean the wearer's torso forward and briefly held in this position (605). This forward lean both cues the wearer that the standing motion is about to initiate, as well as moves the wearer's center of gravity forward, over their feet. This is referred to as the Lean Forward (613) phase as the torso leans forward, and the momentum transfer phase (614) as the wearers weight is transferred from the seat to their feet. Next, in the extension and lift phase (615) the hip extensors (601) and spinal extensors (616) are actuated (607, 610) as the hip flexors (603) are deactivated (606), assisting the wearer as they rise into a standing position. In the standing phase (617) the hip extensors (601) and spinal extensors (616) are held in an actuated state (608, 611) while the wearer assumes a balanced standing posture. The hip extensors (601) and spinal extensors (616) are then deactivated (609, 612) to allow freedom of movement in the standing posture. In this example, tendon components (602) are shown in series with the hip extensors (601). The tendons (602) transmit tensile loads, allowing the FLAs to operate across spans longer than the FLAs, as well as enabling optimal placement of the FLAs for comfort and functionality.

Figure 6B:
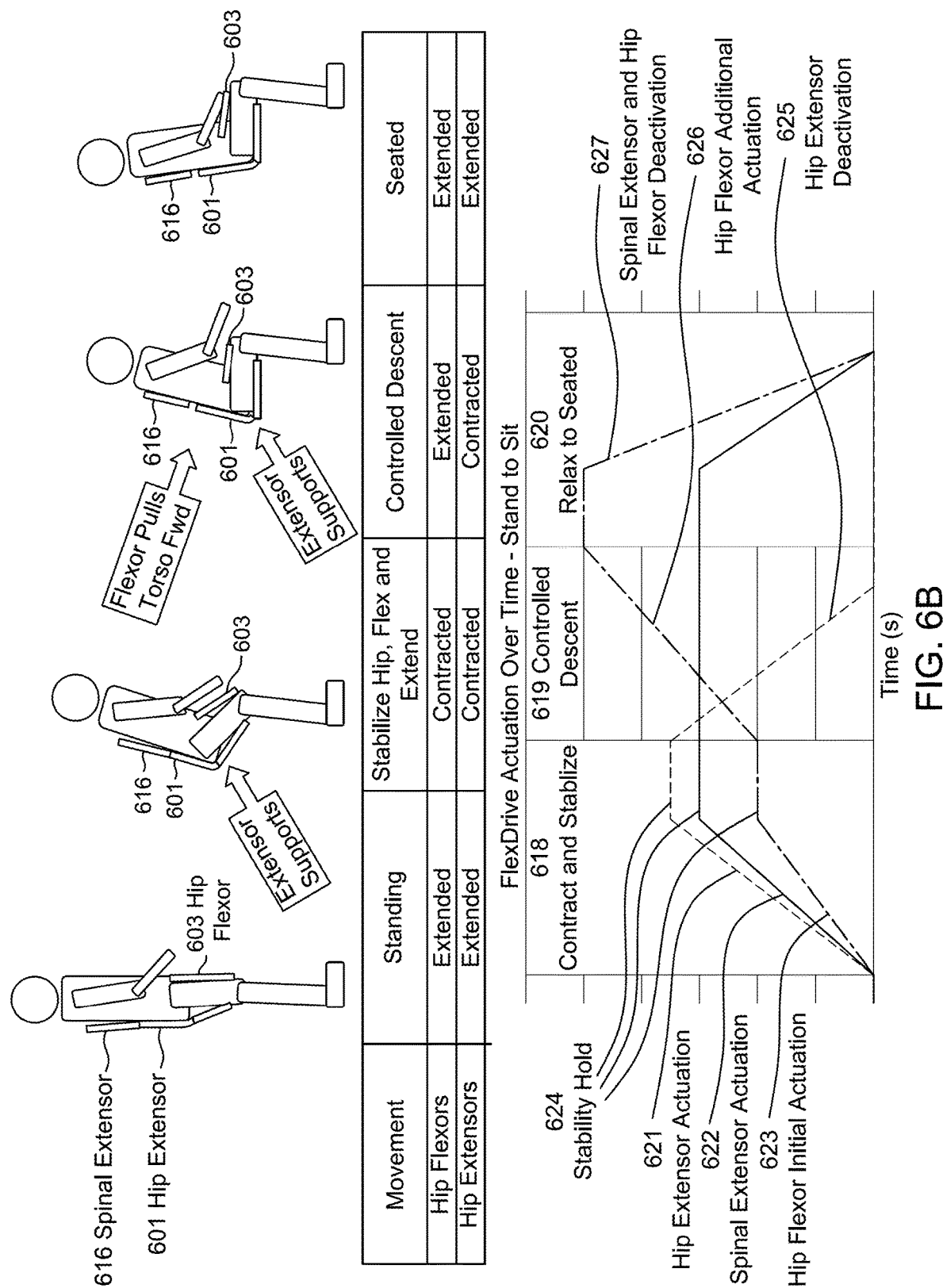
FIG. 6B shows a motion profile for a stand-to-sit activity according to some embodiments of the present disclosure.

FIG. 6B illustrates a stand-to-sit motion/activity profile according to some embodiments of the present disclosure. In the initial contract and stabilize phase (618), the spinal extensors (616), hip extensors (601) and hip flexors (603) are all actuated (621, 622, 623) to provide stability to the wearer prior to initiating movement, as well as to cue the wearer that the movement is about to start. After a brief hold for stability (624), in the controlled descent phase (619) the hip extensors are deactivated (625) while additional actuation of the hip extensors (626) assist the wearer during descent and transition to the seated position. In this way, the exosuit provides assistance analogous eccentric muscle activity. In the final phase (620), the spinal extensors and hip flexors deactivate (627), allowing the wearer to relax in the seated position.

Figure 6C:
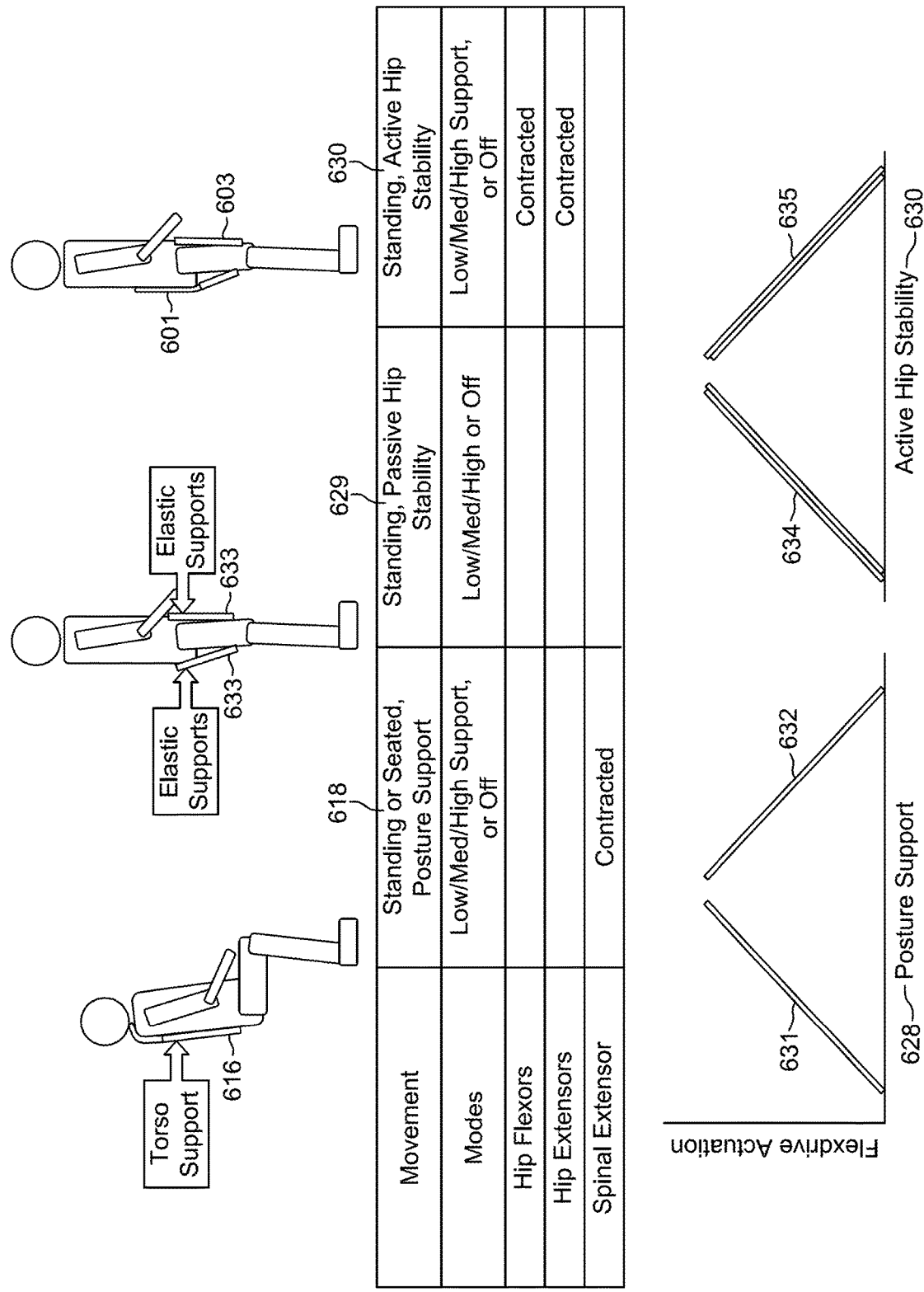
FIG. 6C shows a motion profile for providing postural stability according to some embodiments of the present disclosure.

FIG. 6C illustrates profiles or modes for postural and stability support according to some embodiments of the present disclosure. Postural support (628) in the standing or seated position typically involves actuation (631) of the spinal extensors (616). Actuation of the spinal extensors typically reduces thoracic kyphosis (forward bending) or increases lumbar lordosis (backward bending), moving the head backward such that the upper body is in a more balanced posture over the hips. Support maintaining this posture can reduce fatigue and increase comfort in both the standing and seated positions. When the postural support is no longer needed or if another motion or activity is to be performed, the spinal extensors may be deactivated (632).

In a passive standing hip stability mode (629), elastic supports (633) analogous to the hip flexors and hip extensors maintain passive stability of the hips. The elastic supports (633) are typically components of the stability layer. The elastic supports (633) may be engaged or adjusted manually such as by tensioning a strap, or by simply coupling or uncoupling the supports from anchors on the suit such as snaps or other fasteners. As described further below in FIG. 6E, the elastic supports may be engaged, disengaged and adjusted using a combination of powered actuators and clutches. Likewise, the active supports described here may be used in combination with elastic supports and clutching mechanisms.

Standing, active hip stability (630) may be provided by simultaneous actuation (634) of the hip flexors (603) and hip extensors (601). This is analogous to simultaneous, isometric contraction of the hip flexor and extensor muscles to stabilize the joint in the standing position. When active hip stability is no longer required, the hip flexors and hip extensors simultaneously deactivate (635). Different modes or amounts of hip stability support may be provided, such as high, medium or low amounts or support; or variable support depending on the instantaneous needs of the wearer. The amount of support may be determined by wearer characteristics such as height, weight, age and strength; or may be actively controlled by the sensors and controls layer. For example, data from one or more inertial measurement units (IMUs) may indicate a level of active stability needed to assist the wearer.

Figure 6D:
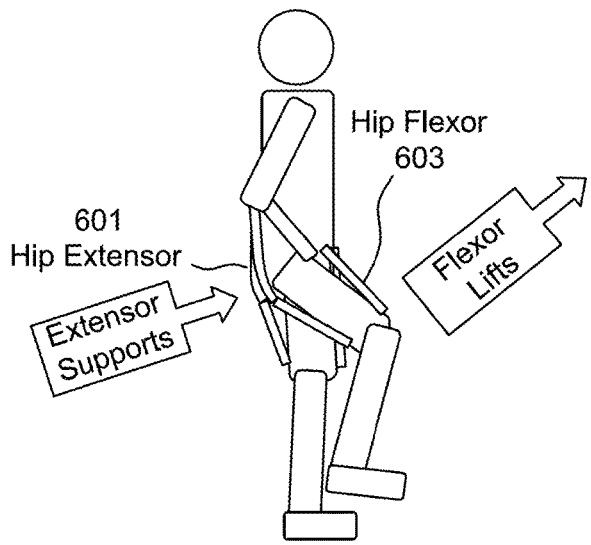
FIG. 6D shows a motion profile for gait assistance according to some embodiments of the present disclosure.
Figure 6D:
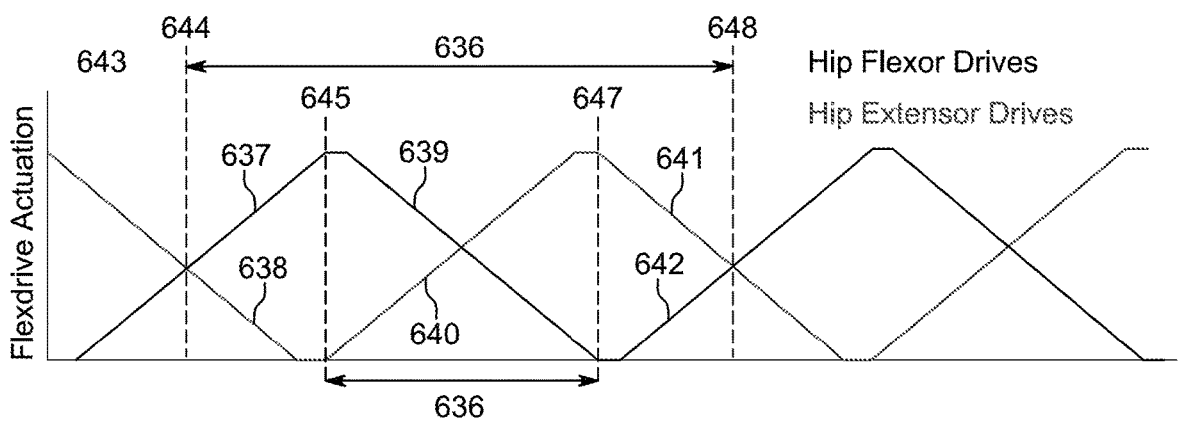

FIG. 6D illustrates a profile or mode for gait assistance according to some embodiments of the present disclosure. In gait assistance, the hip flexor (603) and hip extensor (601) FLAs act in conjunction to cyclically assist moving the legs forward and backward during a gait cycle (walking). FLA actuation of a single leg during gait assistance is shown graphically (643). During a single gait cycle (636) beginning from the mid-swing position (644), the leg is swung forward by simultaneously actuating the hip flexors (637) and deactivating the hip extensors (638). Typically beginning at heel-strike (645), the hip flexors are then deactivated (639) while the hip extensors are actuated (640), moving the leg back through the stance phase (646). Then, typically at toe-off (647), the hip flexors are again actuated (641) while the hip extensors are deactivated (642), initiating the swing phases, and returning the leg to mid-swing, where the cycle repeats. The opposite leg is actuated in the same manner, but in the opposite phase—i.e., one leg can have the hip flexors actuated during the swing phase, while the opposite leg has the hip extensors actuated during the stance phase.

The gait cycle may be manually initiated and controlled by the wearer via user interface controls, or automatically initiated and controlled by the sensors and controls layer. For example, sensors such as IMUs may detect that the wearer is walking, control algorithms determine the appropriate assistance to be provided during the gait cycle, and the FLAs are actuated accordingly.

Figure 6E:
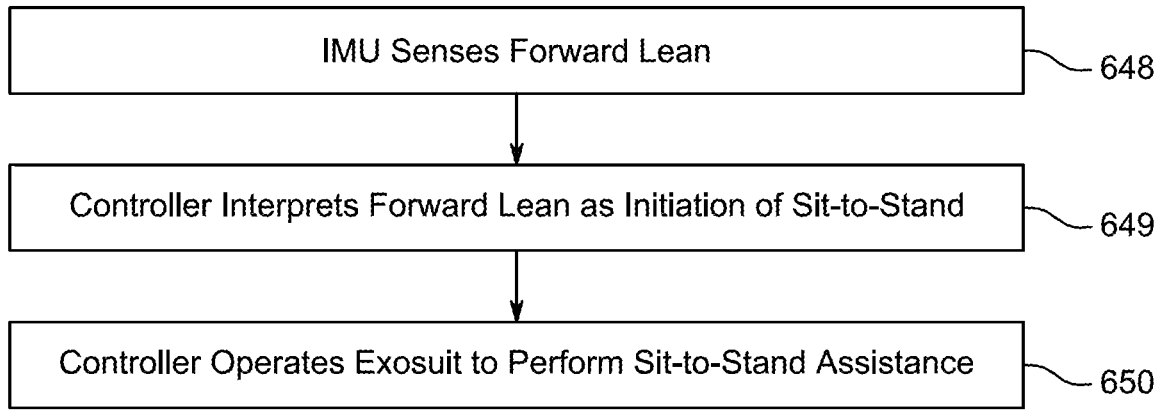
FIG. 6E illustrates an embodiment of a process for executing sit-to-stand assistance according to some embodiments of the present disclosure.

FIG. 6E illustrates an embodiment of a process for executing sit-to-stand assistance. One or more inertial measurement units (IMUs) sense the wearer leaning forward (648). A controller or central processing unit (CPU) interprets the forward lean as the wearer initiating a sit-to-stand movement (649). Alternatively, the wearer could indicate to the exosuit system via a user interface that they are about to perform a sit-to-stand movement. The controller or CPU then operates the exosuit to assist with the sit-to-stand movement (650), typically by actuating one or more FLAs or clutch elements according to a motion profile as described above.

In one embodiment, the sit-to-stand assistance movement may be implemented as follows. The FLAs responsible for hip flexor assistance movement (the hip flexor FLAs) may be activated to initiate a lean forward movement of a torso of a body. The hip flexor FLAs increase force tension until a hip flexor force reaches a hip flexor holding force threshold. The hip flexor force can be maintained at the hip flexor holding force threshold for a first period of time. The FLAs responsible for hip extensor assistance movement (the hip extensor FLAs) may be activated prior to an end of the first time period to initiate a lift movement of the body. The hip extensor FLAs increase force tension until a hip extensor force reaches a hip extensor holding force threshold. The FLAs responsible for spinal extensor assistance movement (the spinal extensor FLAs) may be activated to assist in the lift movement of the body. The spinal extensor FLAs increase force tension until a spinal extensor force reaches a spinal extensor holding force threshold. The hip flexor FLAs may be deactivated at the end of the first period time such that hip flexor FLAs decrease force tension to further assist in the lift movement of the body. Deactivation of the hip flexor FLAs decreases the hip flexor force relative to increases to the hip extensor and spinal extensor forces.

When the sensors detect that the body is standing, the hip extensor FLAs may be deactivated and the spinal extensor FLAs may be deactivated.

Figure 6F:
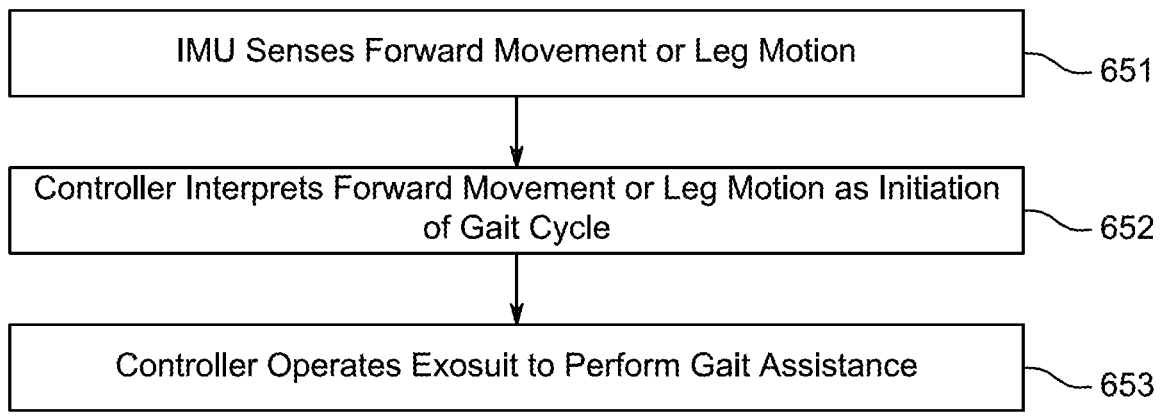
FIG. 6F illustrates an embodiment of a process for executing gait (walking) assistance according to some embodiments of the present disclosure.

FIG. 6F illustrates an embodiment of a process for executing gait (walking) assistance. One or more IMUs sense forward motion or leg movement of the wearer (651). The controller or CPU interprets the forward motion or leg movement as the wearer initiating a gait cycle, i.e. beginning to walk (652). Alternatively, the wearer could indicate to the exosuit system via a user interface that they are beginning to walk. The controller or CPU then operates the exosuit to assist with walking or gait assistance, typically by actuating one or more FLAs or clutch elements according to a motion profile as described above (653).

In one embodiment, the gait assistance movement may be implemented as follows. For a first leg, the FLAs responsible for hip flexor assistance movement associated with the first leg the second leg flexor FLAs and the FLAs responsible for hip extensor assistance movement associated with the first leg (the first leg hip extensor FLAs) may be alternatively activated and deactivated. For a second leg, the FLAs responsible for hip flexor assistance movement associated with the second leg (the second leg hip flexor FLAs) and the FLAs responsible for hip extensor assistance movement associated with the second leg (the second leg hip extensor FLAs) may be alternatively activated and deactivated. The activation and deactivation of the second leg flexor FLAs and the second leg hip extensor FLAs are out of phase with respect to the activation and deactivation of the first leg flexor FLAs and the first leg hip extensor FLAs. The first leg extensor FLAs may be simultaneously activated in conjunction with activation of the second leg hip flexor FLAs, and the second leg flexor FLAs may be simultaneously activated while deactivating the second leg hip extensor FLAs. For the first leg, when the first leg extensor FLAs exert a maximum extensor force, the first leg flexor FLAs may exert no force, and when the first leg flexor FLAs exert a maximum flexor force, the first leg extensor FLAs may exert no force.

Figure 6G:
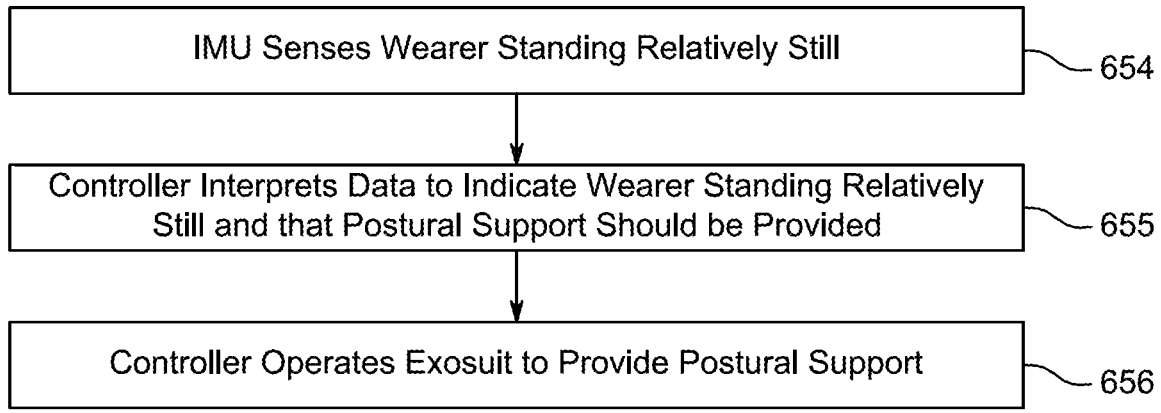
FIG. 6G illustrates an embodiment of a process for executing standing postural support assistance according to some embodiments of the present disclosure.

FIG. 6G illustrates an embodiment of a process for executing standing postural support assistance. One or more IMUs sense that the wearer is standing relatively still (654). The controller or CPU interprets from the IMU data that the wearer is standing relatively still and that postural support should be provided (655). Alternatively, the wearer could indicate to the exosuit system via a user interface that they are standing still and postural support is desired. The controller or CPU then operates the exosuit to assist with postural support, typically by actuating one or more FLAs or clutch elements according to a motion profile as described above (656).

In one embodiment, the stand-to-sit assistance movement may be implemented as follows. The FLAs responsible for spinal extensor assistance movement (the spinal extensor FLAs) may be activated to increase lumbar lordosis. The spinal extensor FLAs may increase force tension until a spinal extensor force reaches a spinal extensor holding force threshold. The spinal extensor FLAs may be deactivated in response to determining that postural stability is not required. Posture stability may be further enhanced by executing hip stability, which can include simultaneously activating the FLAs responsible for hip flexor assistance movement (the hip flexor FLAs) and the FLAs responsible for hip extensor assistance movement (the hip extensor FLAs). The hip flexor FLAs can increase force tension until a hip flexor force reaches a hip flexor holding force threshold, and the hip extensor FLAs increase force tension until a hip extensor force reaches a first hip extensor holding force threshold. The hip flexor holding force threshold may be defined according to a hip stability mode that includes at least two different amounts of support, and wherein the hip extensor holding force is defined according to the hip stability mode. The hip flexor holding force threshold and the hip extensor holding force may be based on inputs received from the sensors.

Figure 6H:
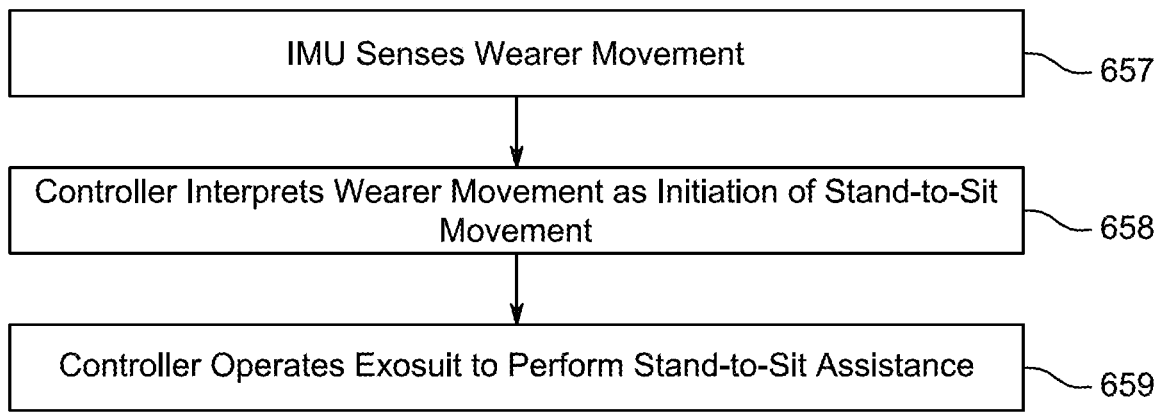
FIG. 6H illustrates an embodiment of a process for executing assistance with a stand-to-sit motion according to some embodiments of the present disclosure.

FIG. 6H illustrates an embodiment of a process for executing assistance with a stand-to-sit motion. One or more IMUs sense motion of the wearer (657). The controller or CPU interprets the motion as the wearer initiating a stand-to-sit movement (658). Alternatively, the wearer could indicate to the exosuit system via a user interface that they are beginning to walk. The controller or CPU then operates the exosuit to execute stand-to-sit assistance, typically by actuating one or more FLAs or clutch elements according to a motion profile as described above (659).

In one embodiment, the stand-to-sit assistance movement may be implemented as follows. The FLAs responsible for hip flexor assistance movement (the hip flexor FLAs), the FLAs responsible for hip extensor assistance movement (the hip extensor FLAs), the FLAs responsible for spinal extensor assistance movement (the spinal extensor FLAs) may be simultaneously activated. The hip flexor FLAs increase force tension until a hip flexor force reaches a hip flexor holding force threshold, wherein hip extensor FLAs increase force tension until a hip extensor force reaches a first hip extensor holding force threshold, and the spinal extensor FLAs may increase force tension until a spinal extensor force reaches a spinal extensor holding force threshold. The hip flexor force may be maintained at the first hip flexor holding force threshold. The hip extensor force may be maintained at the hip extensor holding force threshold. The spinal extensor force may be maintained at the spinal extensor holding force threshold for a first time period. At an end of the first time period, and during a controlled decent duration, the hip flexor force may be reduced by deactivating the hip flexor FLAs, the spinal extensor force may be maintained at the spinal extensor holding force threshold, and the hip extensor force may be increased to a second hip extensor holding threshold by further activating the hip extensor FLAs. During the controlled decent duration, the reduction in the hip flexor force and the increase the hip extensor force is proportional to a speed at which the body approaches the sit position. If the sensor detect that the user is sitting, the hip extensor FLAs and the spinal extensor FLAs may be deactivated.

Figure 6I:
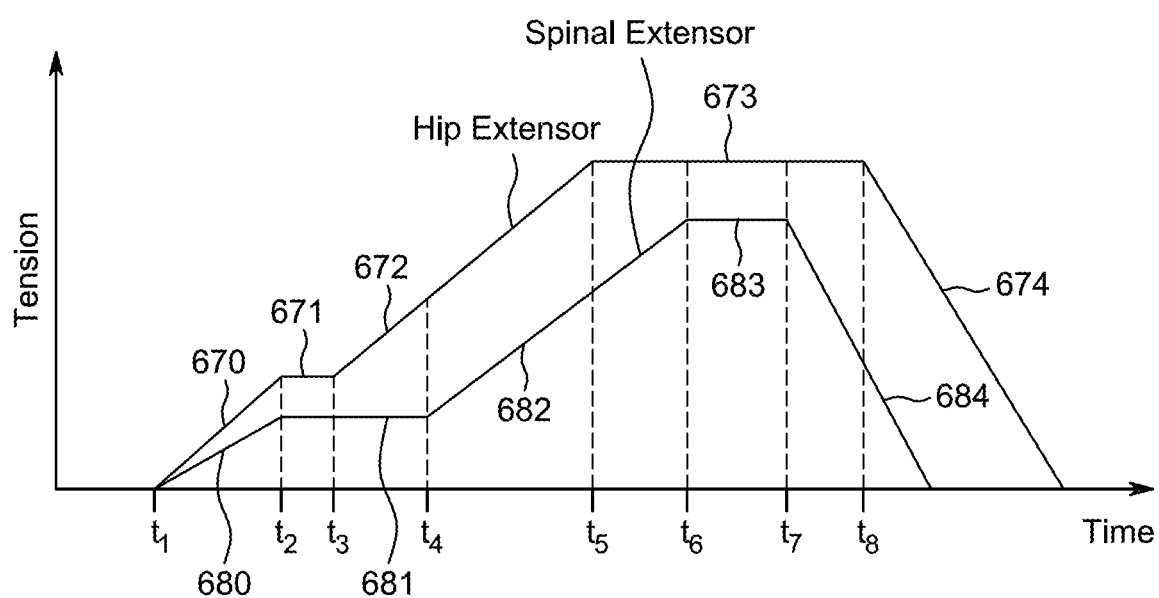
FIG. 6I illustrates a sit-to-stand activity/motion timing diagram according to some embodiments of the present disclosure.

FIG. 6I illustrates a sit-to-stand activity/motion timing diagram according to some embodiments of the present disclosure. FIG. 6I illustrates a sit-to-stand assistive movement using only hip and spinal extensors, and no hip flexors. At time t1, the exosuit may receive an indication that a sit-to-stand assistive movement is requested. After receiving the request, the exosuit may pre-twist hip extensors 670 and spinal extensors 680 to provide pre-tension of extensors 670 and 680. The pre-twist action may tighten up any slack that may exist within the twisted strings associated with the FLAs that perform hip and spinal extensor movements. This way, when the user engages his/her own muscles, the FLAs provide immediate support and do not have to "catch up" to the user. At time, t2, the hip and spinal extensors may be held at respective first hip extensor hold 671 and first spinal extensor hold 681. At time, t3, the hip extensor FLAs may further activate to increase tension from time, t3, to time, t5, as shown by segment 672. At time, t4, the hip extensor FLAs may maintain tension at second hip extensor hold 673.

Starting at time, t4, the spinal extensor FLAs may increase tension from time, t4, to time, t6, as shown by segment 682. At time, t5, the spinal extensor FLAs may maintain tension at second spinal extensor hold 683. The hip extensors and spinal extensors are then deactivated at times, t8 and t7, respectively to allow freedom of movement in the standing posture.

Figure 7:
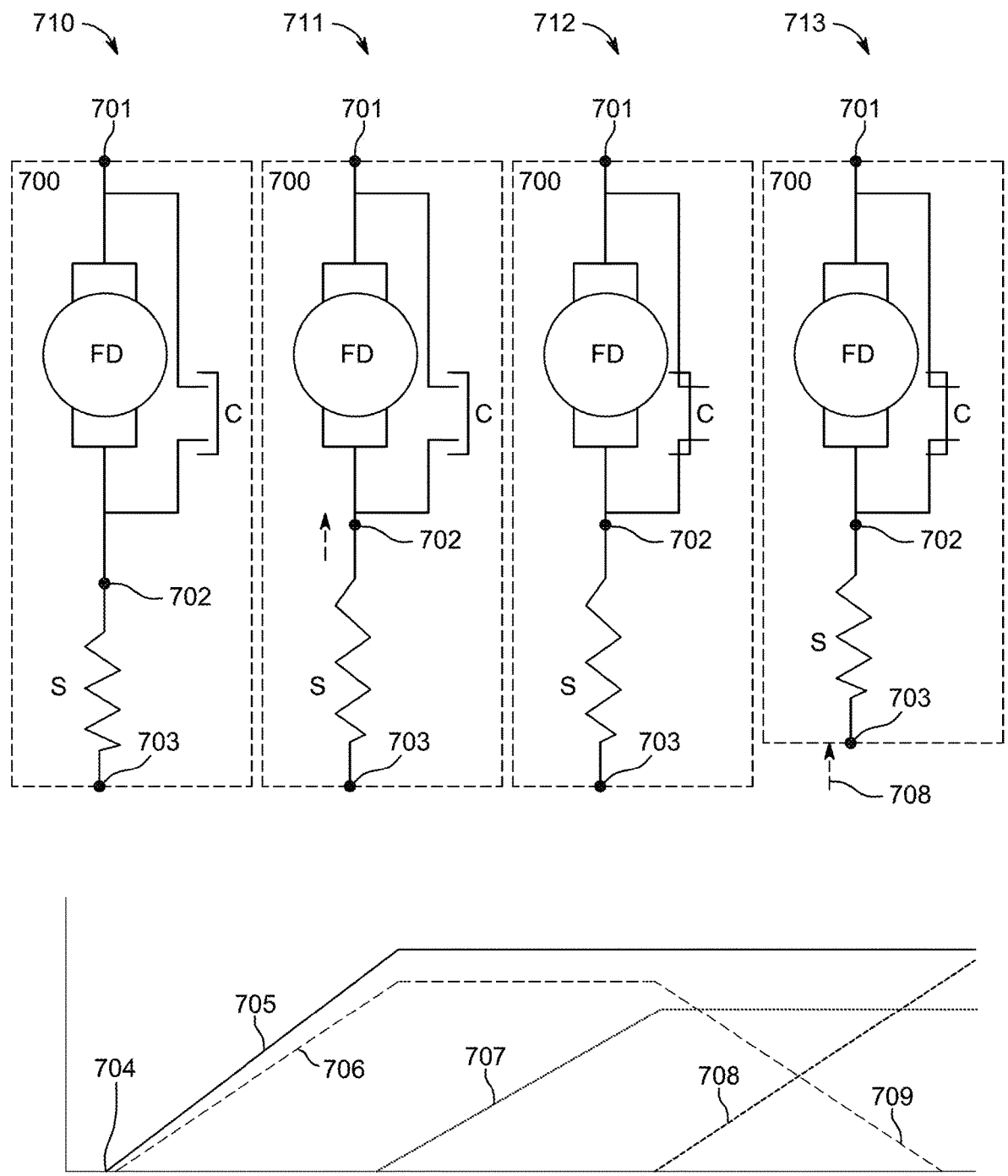
FIG. 7 shows a schematic and motion profile for a clutched flexible linear actuator (FLA) and spring subsystem according to some embodiments of the present disclosure.

FIG. 7 illustrates an example of a sub-system (700) of an assistive exosuit system and motion profile that incorporates an FLA (FD), clutch (C) and spring (S). In this example, the FLA (FD) and clutch (C) are arranged in parallel, attached at a first end (701) to an anchor on the exosuit and at the second end (702) to one or more springs (S). The opposite end of the one or more springs (703) is attached to one or more anchors at a second location on the exosuit. Initially (704), the FLA (FD) is in the deactivated state, the clutch (C) is disengaged, and the spring (S) is in a relaxed state, generating little or no force. In some embodiments, the spring (S) may represent the twisted string that can be wound up or unwound by the FD. When the twisted string is under force tension, the spring (S) may be represented as being under tension (as shown in phases 711 and 712). When the twisted string is relaxed, the spring (S) may be represented as being relaxed (as shown in phases 710 and 713). In another embodiment, the spring (S) may represent an element that is completely separate from the FLA. That element may be a spring element such as an elastic band that is attached to the twisted string of the FLA.

The FLA (FD) is then actuated (705), drawing the second end (702) of the FLA (FD) toward the first end (701) of the FLA. At the same time the spring (S) is elongated, generating a tensile force and potential energy (706) in the spring. Next, the clutch (C) is engaged (707), maintaining the distance between the first and second ends (701, 702) of the FLA (FD) without further actuation of the FLA. At this point, the spring (S) is still elongated, generating a tensile force and stored potential energy.

As the wearer performs an activity or moves (708) into a position that reduces the distance between the first end (701) of the FLA and opposite end (703) of the spring, the force and potential energy stored in the spring assist the wearer in the activity or motion, decreasing (709) as the motion is completed.

In one example, such a subsystem (700) may be configured as a hip extensor for assisting the wearer when moving from a seated to standing position (sit-to-stand). The first end (701) of the FLA may be anchored to the torso in the region of the lower back, while the opposite end (703) of the spring may be anchored to the back of the thigh. In the initial state (710), the FLA (FD) and clutch (C) are deactivated, with little or no force in the spring (S) while the wearer is seated. In the next phase (711) in preparation to stand, the FLA is actuated (705), generating a tensile force and potential energy (706) in the spring. In the next phase (712), the clutch (C) is engaged (707), to maintain the spring tension without further actuation or back-driving the FLA. In the next phase (713), the wearer moves into the standing position. The tensile force and potential energy stored in the spring assist in this motion, while the force and tensile energy decrease (709) as the motion is performed and the distance is reduced between the first end (701) of the FLA and opposite end (703) of the spring.

Sub-system (700) can be used in an exosuit. Such an exosuit may include a first load distribution member configured to be worn around a first body segment of a human, and a second load distribution member configured to be worn around a second body segment of the human. The exosuit can include a muscle assistance sub-system (e.g., such as sub-system 700) coupled to the first and second load distribution members. The muscle assistance sub-system can include a first attachment point coupled to the first load distribution member, a second attachment point coupled to the second load distribution member, and a flexible linear actuator (FLA) coupled to the first and second attachment points. The FLA can include a motor (e.g., shown as FD in sub-system 700) and at least one twisted string coupled to the motor and the second attachment point. In this embodiment, the twisted string may serve as the spring (S) in sub-system 700. However, it should be appreciated that a separate spring element may be coupled to the twisted string and to the second attachment point. The exosuit can include clutch positioned in parallel with the motor such that it is coupled to the first attachment point and a third attachment point existing between the motor and the second attachment point. When the clutch is disengaged, a tensile force in the at least one twisted string is maintained by the motor, and when the clutch is engaged, the tensile force in the at least one twisted string is maintained by the clutch. The exosuit can also include control circuitry operative to control operation of the motor and the clutch.

The motor may be operative to increase the tensile force by rotating in a first direction, or the motor may be operative to decrease the tensile force by rotating in a second direction. The second direction is opposite of the first direction. To save power, the FLA may be deactivated when the clutch is engaged. When the clutch is engaged and the tensile force is set at a first tensile force threshold, the FLA may be deactivated for a first period of time such that if the clutch were to be disengaged, the tensile force would drop below the first tensile force threshold, and at an end of the first period of time, the FLA is activated such that if the clutch where to be disengaged, the tensile force is maintained at or above the first tensile force threshold.

Figure 8A:
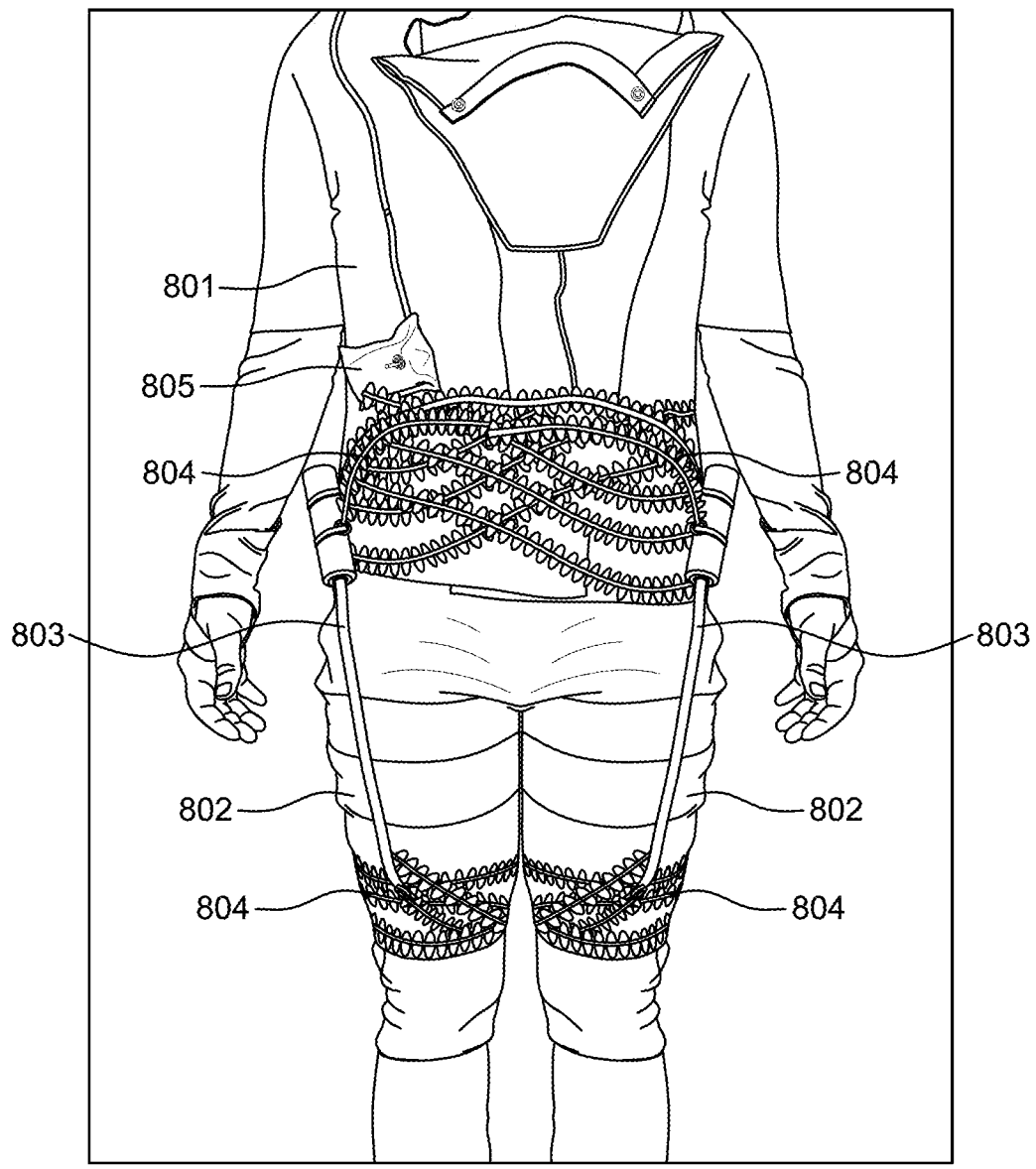
FIG. 8A shows a front view of an exosuit according to some embodiments of the present disclosure.
Figure 8B:
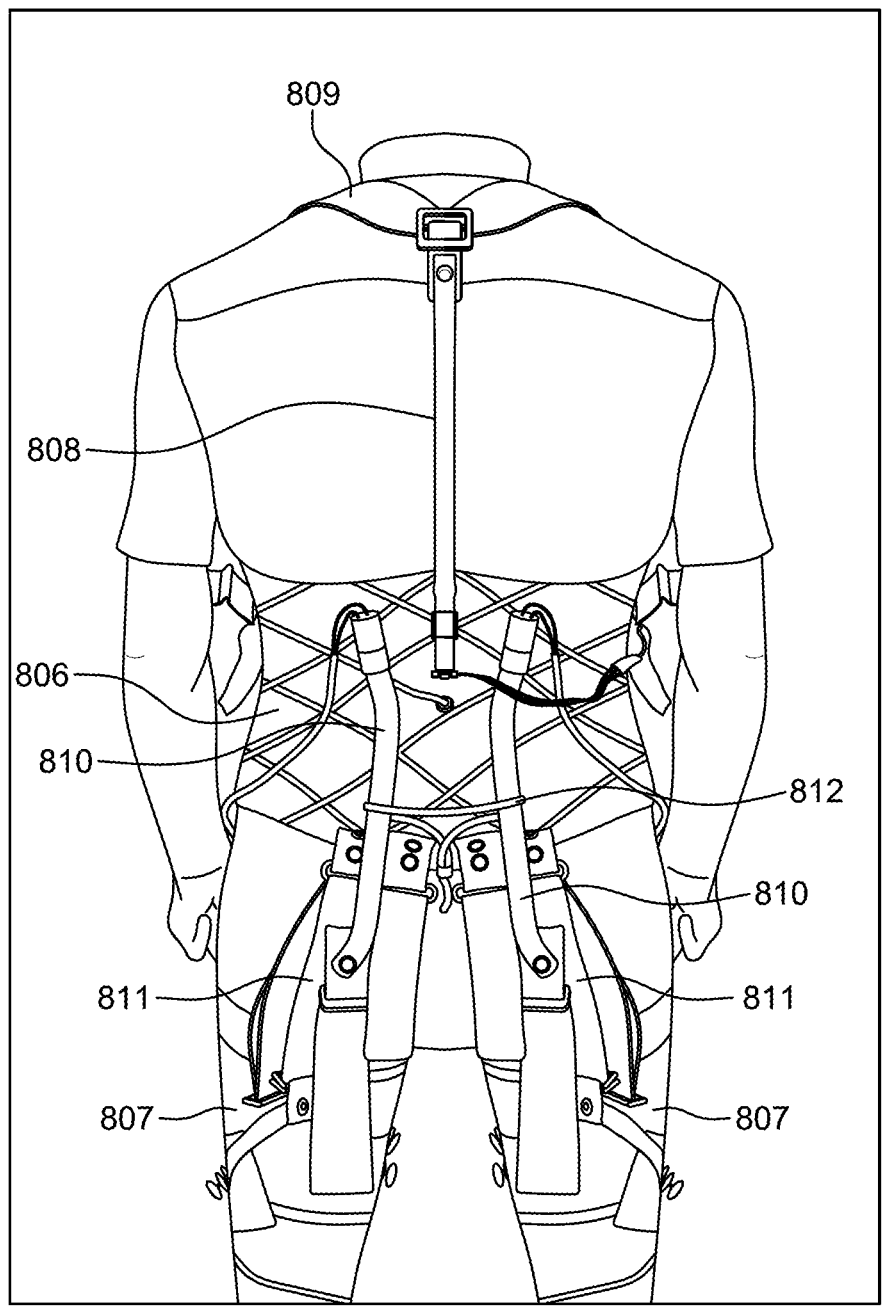
FIG. 8B shows a back view of an exosuit according to some embodiments of the present disclosure.
Figure 8C:
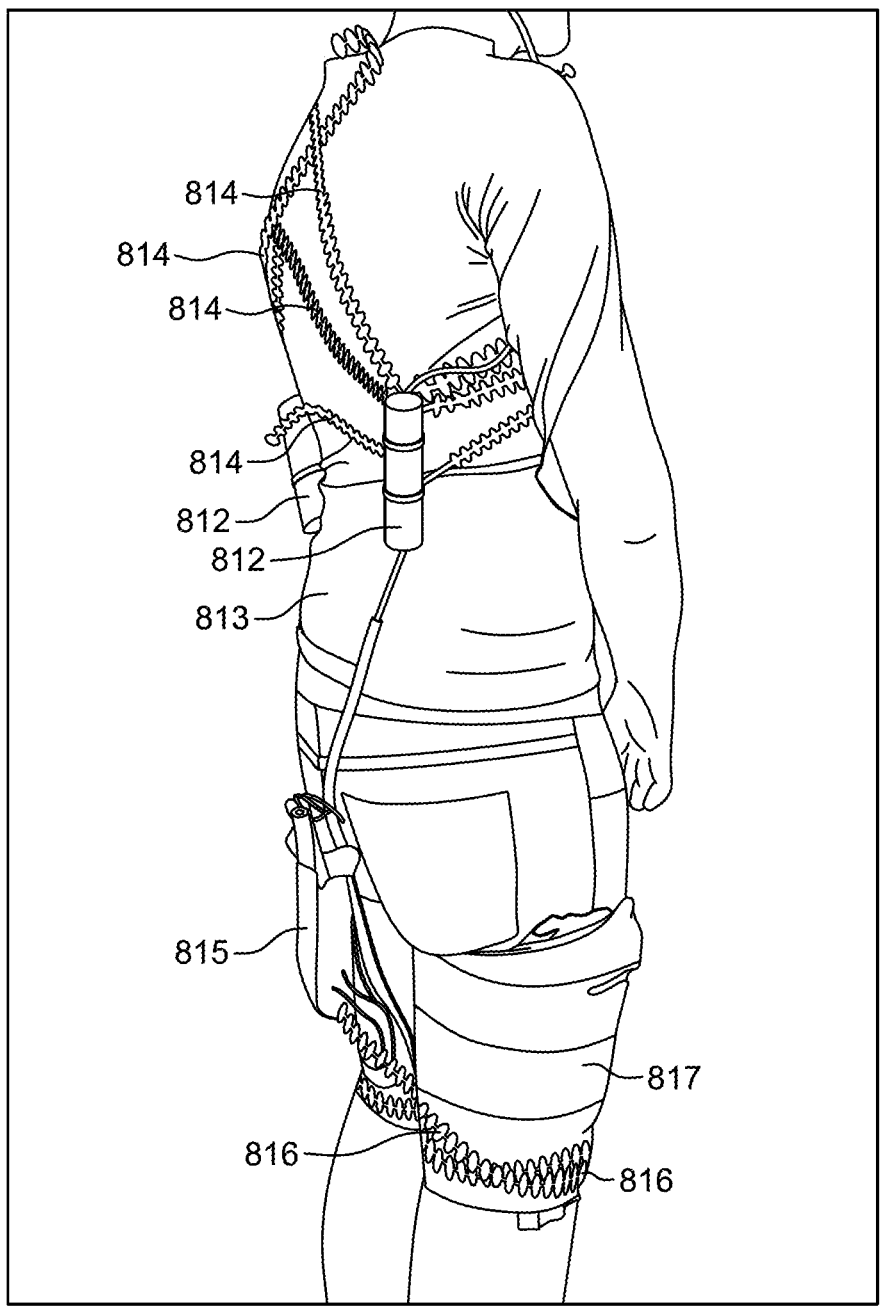
FIG. 8C shows a side view of an exosuit according to some embodiments of the present disclosure.

FIGS. 8A-8C illustrate an assistive exosuit according to some embodiments of the present disclosure. In FIGS. 8A-8C, the assistive exosuit is extensively or infinitely configurable for testing or provisional use while optimizing a suit for an individual wearer. In these situations—where a suit is used for testing with different wearers, or where a suit is being configured specifically for an individual wearer, it may be desirable to adjust the position or orientation of suit components such as power layer FLAs, stability layer elastic elements, and base layer load distribution members. In some embodiments, a provisional/testing exosuit (PTE) includes modular components that can be assembled in extensively or infinitely varied arrangements or configurations for testing purposes or optimization for a specific wearer.

To allow for additional configurable capability of the PTE, a tether may allow for some electronic and mechanical components to be housed off the suit. In one example, electronics such as circuit boards and batteries may be over-sized, to allow for added configurability or data capture. If the large size of these components makes it undesirable to mount them on the PTE, they could be located separately from the suit and connected via a physical or wireless tether to reduce system weight that can interfere with accurate evaluations of functionality. Larger, overpowered motors may be attached to the PTE via flexible drive linkages that allow actuation of the power layer without requiring large motors to be mounted directly on the PTE. Such over-powered configurations allow optimization of PTE parameters without constraints requiring all components to be directly attached or integrated into the PTE.

FIG. 8A shows a front view of a PTE according to some embodiments of the present disclosure. In this example, the base layer comprises shirt (801) over the arms and trunk, and legging sections (802) over the thighs. The base layer is initially non-structural, and provides surfaces to attach exo-suit components. The outer surface of the PTE base layer ideally is suited to attach modular components, for example with hook and loop fasteners. In this example, the surface of the base layer comprises loops that mate with hooks on the components that are to be attached. Depending on the activities that can be tested or utilized, the base layer may be adapted to different areas of the body such as the legs, core, arms, etc. The inner surface of the base layer preferably provides friction to grip against the wearer's clothing or skin. The friction resists forces generated by the power or stability layers such that the base layer remains in place along the wearer's body.

Components of the stability and power layers may be modularly positioned and attached to the base layer. In the example of FIG. 8A, two FLAs (803) are attached to the waist and anterior thighs, analogous to hip flexor muscles. The FLAs are attached to the base layer with a plurality of cords with attached fastener segments, described as load bearing strap (804) (as discussed in more detail below in connection with FIGS. 19A and 19B). In this example, the fastener segments of the load bearing strap include small pieces of hook-and-loop fastener (hook portion) laminated to supporting structures that are stitched to the cord. The hook-and-loop fasteners allow the load bearing strap to be easily attached to the base layer in almost any configuration. Typically, a plurality of fern-tape segments can be attached to ends of the stability or power layer components and arranged in configurations such as catenary curves to create an effective load distribution member and distribute loads evenly across surfaces of the wearer's body. The load bearing strap and corresponding components may be removed and repositioned to optimize the exosuit layout for properties such as biomechanical performance, comfort, body type or specific activities to be performed. The power layer may be actuated and controlled via manual controls (805) operated by the wearer, by remote controls operated by a technician, or by automated electronic controls.

FIG. 8B shows a back view of a PTE according to some embodiments of the present disclosure. The base layer comprises large elastic segments (806, 807) around the waist and thighs, respectively. In this example, a single FLA (808) is positioned along the midline of the spine, approximating a spinal extensor. The spinal extensor FLA (808) is attached to the waist with the load bearing strap, and is attached at the upper end to webbing tendons (809) over the shoulders. The load bearing strap and webbing allow fast, easy adjustment and optimization of the position and length of the FLA.

Two FLAs (810) attach at the waist and posterior thighs, approximating hip extensor or gluteal muscles. The upper ends of the FLAs (810) are attached to the base layer at the waist with fern-tape. The lower ends of the FLAs (810) are attached to webbing tendons. The opposite ends of the webbing tendons are then attached to fern-tape fastened to the base layer at the posterior thighs. A guide feature (812) controls the alignment and routing of the hip extensor FLAs (810) to optimize the lines of action of the FLAs. In this example, the guide is simply a loop of cord that pulls the middle section of the FLAs medially. A guide could also comprise an eyelet, pulley, hook, track or the like.

Elastic elements (811) of the stability layer are attached to the base layer at the waist and thigh, also with the load bearing strap. In this example, the elastic elements comprise multiple segments of elastic webbing. Adding or removing elastic segments or adjusting their length allows adjustment of the stiffness of the elastic elements. The load bearing strap and adjustable webbing attachments further allow easy adjustment of the position and size of the elastic elements.

FIG. 8C shows a side view of a PTE according to some embodiments of the present disclosure. FLAs (812) approximating hip extensor or gluteal muscles are attached to the base layer (813) at the upper waist with a plurality of load bearing strap segments (814) configured in catenary curves to create a load distribution member. The lower ends of the FLAs (812) are attached to webbing tendons (815) that transmit forces generated by the FLAs to the thighs, via load bearing strap (816) attached to the base layer (817) at the thighs.

Figure 9A:
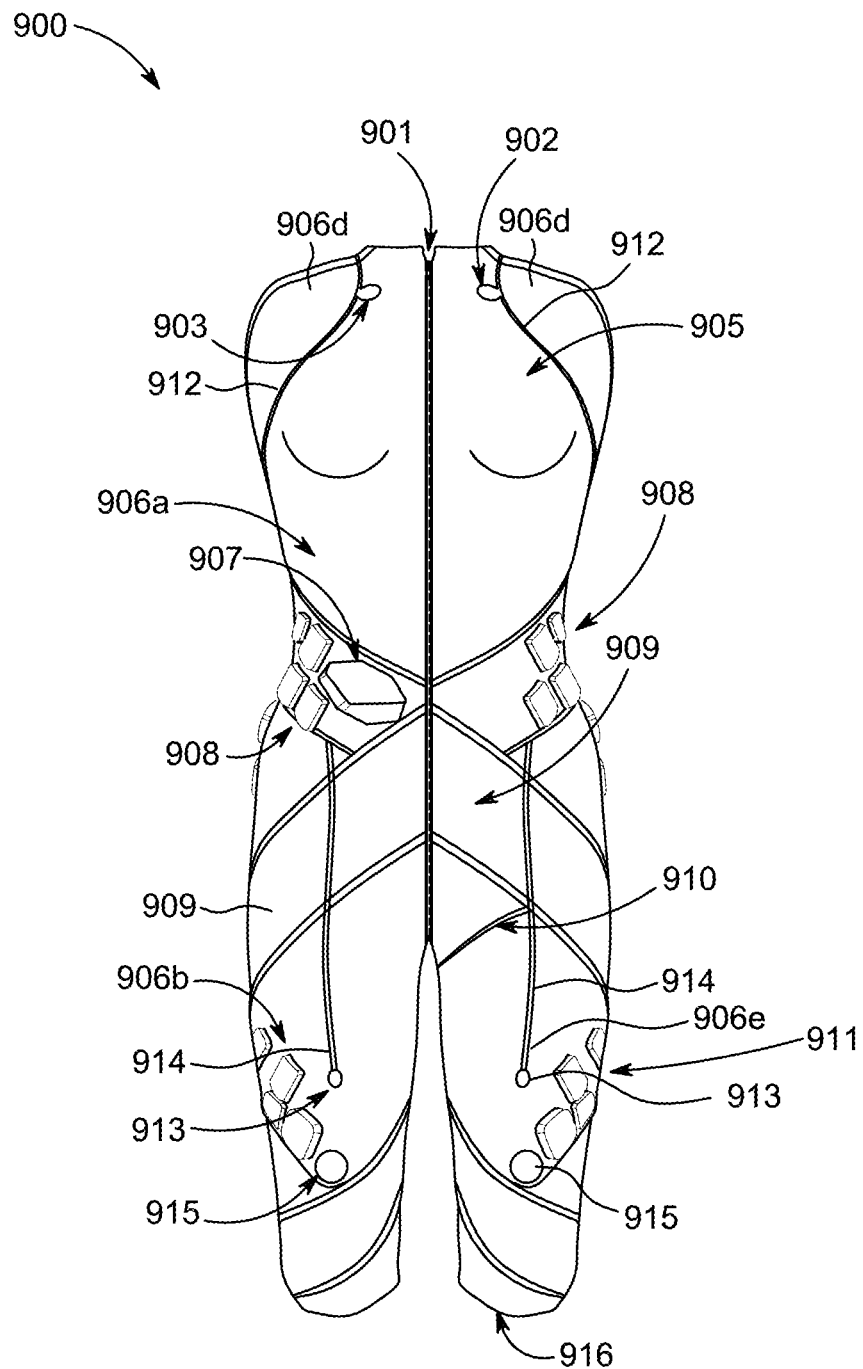
FIG. 9A shows a front view of a uni-suit assistive exosuit according to some embodiments of the present disclosure.
Figure 9B:
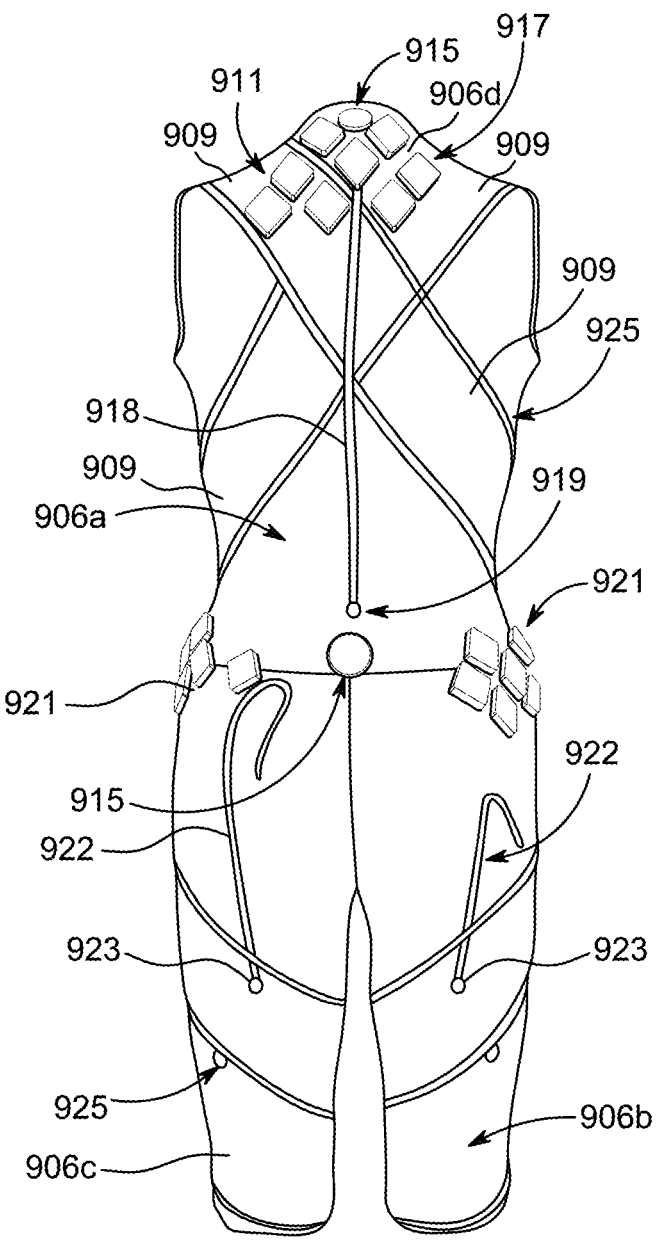
FIG. 9B shows a back view of a uni-suit assistive exosuit according to some embodiments of the present disclosure.

The previous examples generally described assistive exosuits that are to be worn either under or over the wearer's clothing. In some embodiments, the assistive exosuit itself may be stylized and designed such that it is worn as clothing. FIGS. 9A-9B illustrate such an example of assistive exosuit primary clothing, in this case a uni-suit assistive exosuit (USAE) according to some embodiments of the present disclosure. The USAE may represent an integration of two or more of the base layer, stability layer, power layer, and user interface layer.

FIG. 9A shows a front view of a USAE 900 according to some embodiments of the present disclosure. The USAE in this example extends from just above the knees to the shoulders, however alternate configurations are contemplated including covering the lower legs, feet, arms or neck depending on desired aesthetics and exosuit assistive functionality. A long, 2-way zipper (901) provides opening and closure to facilitate donning and doffing the suit. Alternatively, the USAE may include large arm and/or neck openings that allow the suit to be dinned and doffed without a closure feature. A speaker (902) and microphone (903) offer functionality such as voice commands for the wearer to operate the suit, or to act as a mobile communication device. Electrical connections such as wires and cables can travel through channels (912) embedded in USAE 900. Alternatively, conductive materials may be directly woven, braided, printed or otherwise embedded within USAE 900.

USAE 900 may be primarily fabricated from breathable and moisture-wicking textiles (905), with a form-fitting, ultra-soft base fabric (916). Load distribution members (906a, 906b, 906c, and 906d) may be integrally attached or embedded in USAE 900. Load distribution member 906a may be lower torso load distribution member that can function similar to load distribution members 140 and 270 (as discussed above). Load distribution members 906b and 906c may be thigh distribution members that can function similar to load distribution members 120, 130, 242, and 244. Load distribution member 906d may be a shoulder or yoke type of distribution member that can support, for example, spinal extensor loads. FLAs (908) approximating the right and left hip flexors can be attached at the waist (at load distribution member 906a) and anterior thighs (at load distribution members 906b or 906c). FLA anchoring systems (913) can be formed integrally formed with load distribution members (906a, 906b, 906c, and 906d) to support one or more of the motor component of FLAs 908 and the twisted string component of the FLAs. The twisted strings of the FLAs can travel through integral channels (914) formed with USAE 900.

A detachable (or integral) communication hub (907) may provide functionality of a UX/UI layer, such as communication with caregivers, companions, clinical staff or service technicians, health and activity monitoring, or lifestyle features such as identity verification. Custom and/or contoured batteries (911) can be integrated in USAE 900, in configurations optimized for the wearer's comfort. Inertial measurement units (IMUs, 915) are attached to the suit in locations to detect applicable movements. For example, IMU 915 can be positioned on the thighs to detect gait and body position.

An elastic postural support strap (909) component can contour around the hips and trunk to provide core and postural support. Elastic postural support strap 909 may form a double X-shape that crisscrosses the body. For example, support strap 909 may cross near the abdomen region of the suit and again near the upper back of the suit. Support strap 909 may also extend over the shoulders to integrate with load distribution members 906*d*, and support strap 909 may extend around the thighs to integrate with load distribution members 906*b* and 906*c*. Strap 909 may also integrate with load distribution members 906*a*. One or more discrete openings 910 near the groin permit use of the toilet without removing the entire suit. In some embodiments, the groin area may be completely devoid of any layers of the exosuit. In such an embodiment, the user may wear underwear over the suit.

FIG. 9B shows a back view of USAE 900. Custom and/or contoured batteries (911) may be integrally or detachable attached to the suit, for example, near the back of the neck and/or below the shoulders. IMUs (915) may be attached to the upper and lower back to detect trunk position and movement. One or more FLAs (917) approximating spinal extensor muscles can span from load distribution member 906*d* to anchoring system 919 to provide postural support, with the twisted strings running through channels (918) along the spine. One end of postural support FLAs (917) may terminate at FLA anchoring system (919), which efficiently transmits FLA loads to load distribution member (906*a*). FLAs (921) approximating hip extensors or gluteal muscles are attached near the waist, and in particular may be attached load distribution member 906*a*. The twisted strings associated with FLAs 921 may run through channels (922) along the back of the thighs to anchoring systems (923), which transmit FLA forces to load distribution members (906*b* and 906*c*).

One or more pressure sensors (925) may be embedded in USAE 900 to detect pressures experienced by the wearer. The pressure sensing may be utilized by the sensors and control layer to adjust USAE 900 for comfort, or for control of the FLAs to adapt to the specific assistance required for different activities.

USAE 900 may employ a modularity system that enables components typically associated with the power layer such as the FLAs, channels (e.g., control electronics, sensors, and batteries to be removed from the base layer. The base layer may include the fabric worn by the user, the load distribution members (906*a-d*), which are integrated or enhance portions of the fabric, anchor stays, and support straps (such as strap 909). The power layer components can be removed for servicing (e.g., repair, replacement, or battery charging) and the base layer can be washed. Additional discussion on the modularity of power layer components can be found below in connection with the description accompanying FIGS. 20A, 20B, and 21.

Figure 10:
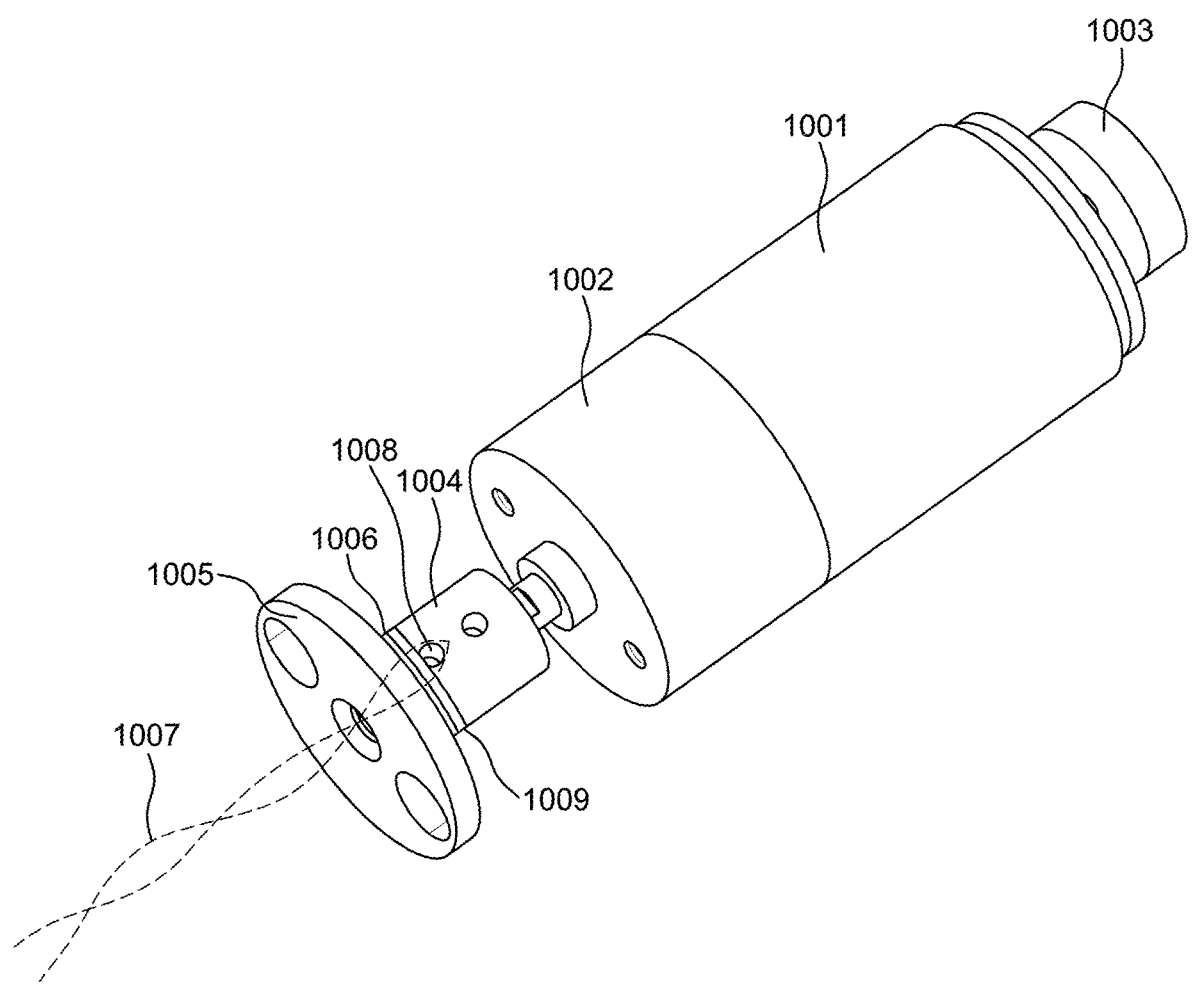
FIG. 10 shows a concept for a twisted string actuator (TSA) motor and spindle configuration according to some embodiments of the present disclosure.

FIG. 10 shows components of a twisted string actuator (TSA) 1000 that may form part an FLA according to some embodiments of the present disclosure. In FIG. 10, TSA 1000 can include a motor (1001), transmission (1002), rotary position sensor (1003), spindle (1004), thrust-plate (1005) and force sensor (1006). In some embodiments, TSA 1000 can include more or less components. The motor (1001) can be a DC motor, either brushed or brushless with direct commutation. The motor can be selected for optimal performance and efficiency, based on the requirements of the exosuit for the intended wearer and activity, as well as the specific details of TSA 1000 such as overall length, stroke length, force, speed and power requirements. The transmission (1002) further enables conversion of the speed and torque of the motor to that required by TSA 1000. The transmission may be geared or use other linkages such as belts or flexible couplings, and be optimized for efficiency and acoustics. The rotary position sensor (1003) detects fractional or full rotations of the motor or transmission for control of TSA 1000. The rotary position sensor may be a magnetic or optical encoder with absolute, relative or quadrature signals; a rotary potentiometer or other similar sensor.

A spindle (1004) is attached to the output of the motor or transmission. The twisted string pair (1007) of the TSA forms a continuous loop around a dowel (1008) in the spindle. The spindle bears against a thrust plate (1005) that bears the tensile forces generated by the TSA. A force sensor such as a load cell, thin film resistor, capacitive force sensor or force sensing resistor positioned between the spindle (1004) and thrust plate (1005) senses the tensile load generated by the TSA for use by the sensors and controls layer. A thrust bearing (1009) positioned between the spindle and force sensor or thrust plate reduces friction and protects stationary components such as the force sensor or thrust plate from damage by the rotating components such as the spindle.

Figure 11:
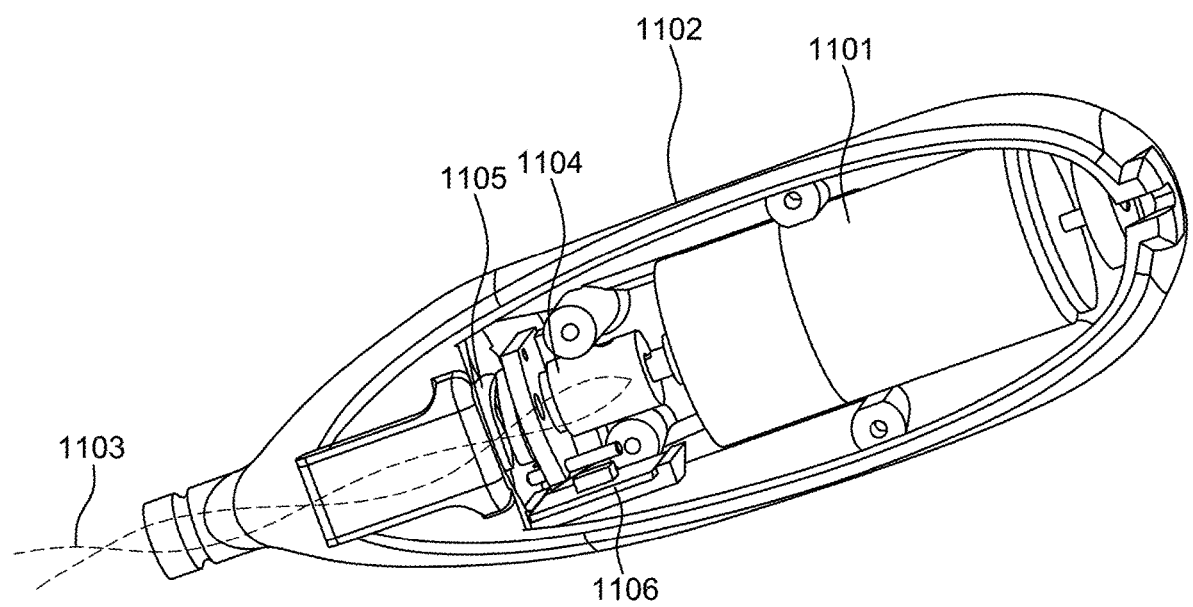
FIG. 11 shows a concept for a TSA configuration with force sensing capability according to some embodiments of the present disclosure.

FIG. 11 illustrates a force sensor system for TSA 1100 according to some embodiments of the present disclosure. The mechanical components including motor and transmission (1101) are enclosed in a contoured housing (1102). Actuation of TSA 1100 generates tensile forces in the twisted string pair (1103). These tensile forces in turn create a compressive force between the spindle (1104) and housing (1102). A spring (1105) placed between the spindle (1104) and housing (1101) can be compressed in response to this compressive load. Compression of the spring (1105) results in displacement of the end of the spring closest to the spindle (1104). This displacement is detectable by a displacement sensor (1106) such as a hall effect sensor, linear encoder, potentiometer or other sensor. The displacement is related to the tensile force in the TSA by the properties of the spring (1105), such as the spring constant. Thus, the displacement detected by the displacement sensor may be utilized by the sensors and controls layer to calculate the tensile force in the TSA.

Figure 12:
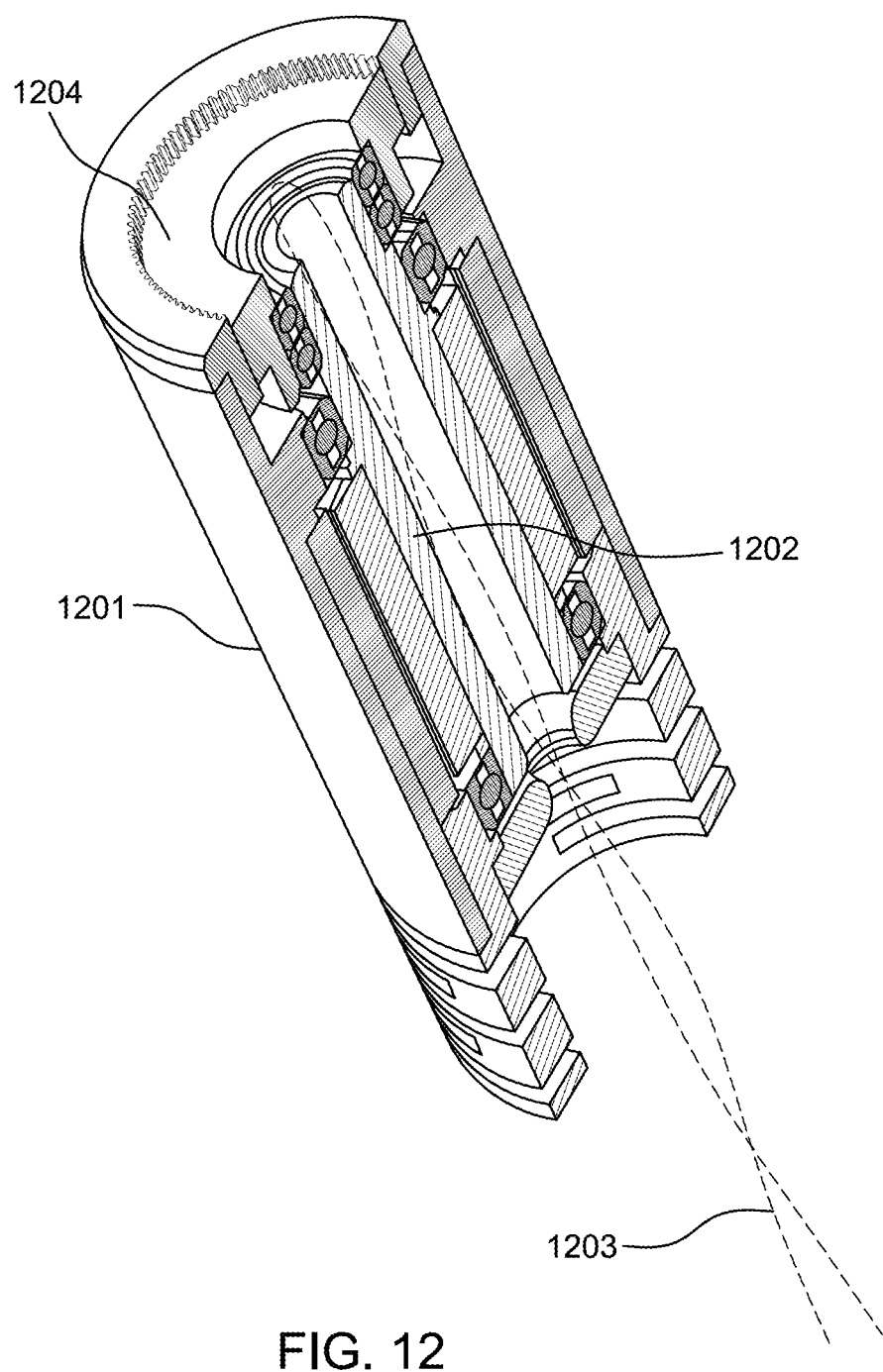
FIG. 12 shows a TSA configuration with a hollow motor and cycloid drive according to some embodiments of the present disclosure.

FIG. 12 illustrates a configuration of TSA 1200 that reduces the overall length required for the TSA assembly according to some embodiments of the present disclosure. A motor (1201) has a central channel or bore (1202). The twisted string pair (1203) runs through this central bore 1202. This significantly reduces the total length of TSA 1200, as the portion of the twisted string pair (1203) within the central bore (1202) is in parallel with the motor (1201) instead of in series with the motor, thus reducing the overall length by this amount. Additionally, a cycloid drive (1204) may provide a substantial gear reduction within a compact size.

Figure 13:
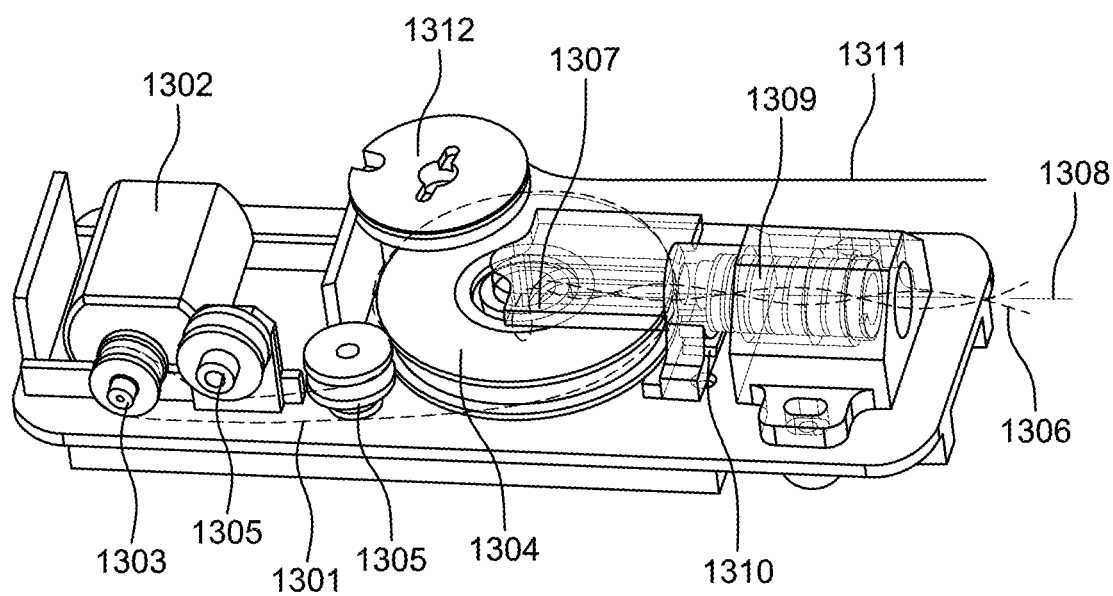
FIG. 13 shows a TSA configuration with an o-ring drive, force sensing and length sensing capability according to some embodiments of the present disclosure.

FIG. 13 illustrates TSA 1300 with an o-ring or belt drive 1301 that enables a large transmission ratio with one or more 90-degree transmissions, a low physical profile and minimal noise according to some embodiments of the present disclosure. An o-ring or flexible belt (1301) is looped around an input pulley (1303) and output pulley (1304). The input pulley (1303) is coupled to the output shaft of the motor (1302), and the output pulley (1304) is attached to the twisted string pair (1306). In this example, two idler pulleys (1305) control alignment of the o-ring or belt (1301). The twisted string pair (1306) is attached to the output pulley (1304) such that as the output pulley rotates, the string is twisted, causing TSA 1300 to contract and generate a tensile force. As the twisted string pair exits the output pulley, it follows a curved bearing surface (1307) so that the effective longitudinal axis (1308) of the string is at an angle, typically perpendicular, to the rotational axis of the output pulley. The angular or perpendicular transmissions that are possible with the o-ring/belt drive and path of the twisted string pair around the bearing surface allow each component to be oriented in the lowest-profile configuration. This is desirable to reduce the overall profile of TSA 1300, both for the wearer's comfort and aesthetics. As with the previous examples, a spring (1309) and displacement sensor (1310) provide tensile load sensing for sensors and control circuitry.

Length sensing is achieved with a string or cord (1311) configured substantially in parallel with the effective longitudinal axis of the twisted string pair (1308). One end of the string or cord (1311) is wound around a spring-loaded reel (1312). The opposite end (not shown) of the string or cord (1311) is anchored to or near the opposite end of the TSA. As the TSA is actuated or deactivated, causing its overall length to lengthen or shorten, the string or cord (1311) is pulled from or retracted onto the spring-loaded reel (1312). A rotational sensor such as a rotary encoder, hall effect sensor, potentiometer or the like detects rotation of the reel (1312). The sensors and control circuitry are then able to utilize the signal from the rotational sensor to calculate absolute length of twisted string pair 1308, which may be an important parameter for control algorithms used to operate the power layer.

Figure 14:
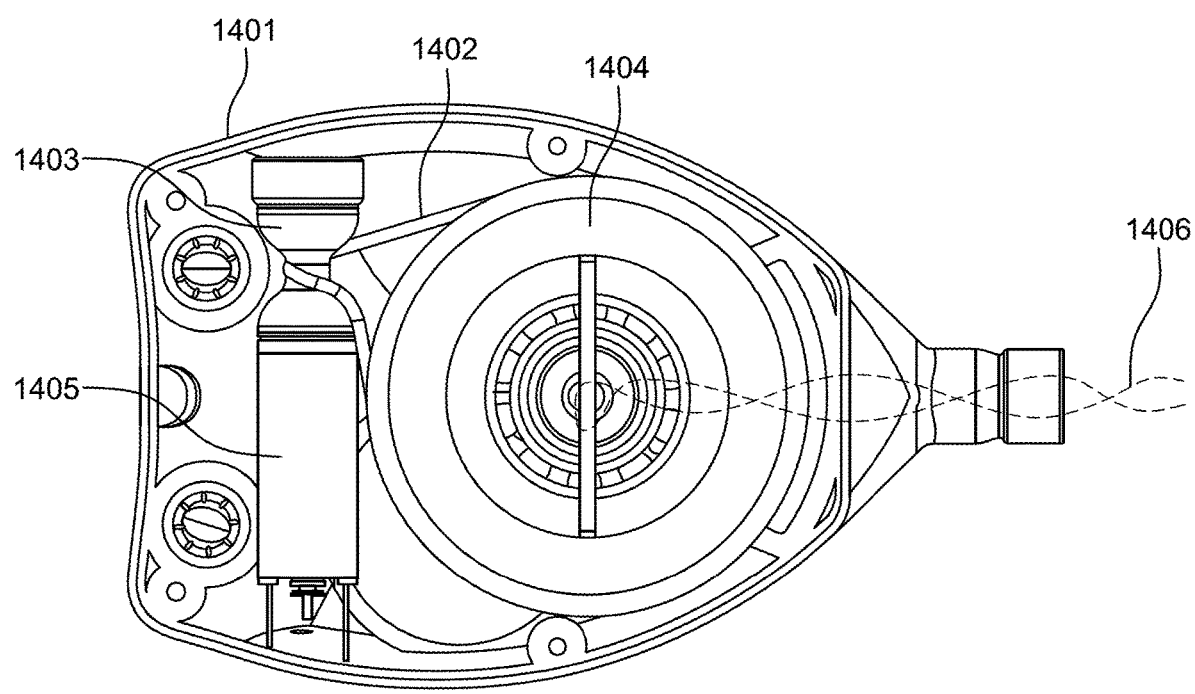
FIG. 14 shows a TSA configuration with an o-ring drive and low-profile housing according to some embodiments of the present disclosure.

FIG. 14 shows TSA 1400 with an o-ring transmission, enclosed in a low-profile, contoured housing (1401) according to some embodiments of the present disclosure. An o-ring or flexible belt (1402) loops around an input pulley (1403) and an output pulley (1404). A motor (1405) drives the input pulley (1403), while the output pulley (1404) twists the twisted string pair (1406) as TSA 1400 is actuated. The right-angle transmission enabled by the o-ring drive allows the motor and output pulley to be oriented within the housing (1401) in the lowest-profile configuration. Friction-based transmissions such as the o-ring drive are also quieter than gear-based transmissions of similar ratios.

Figure 15:
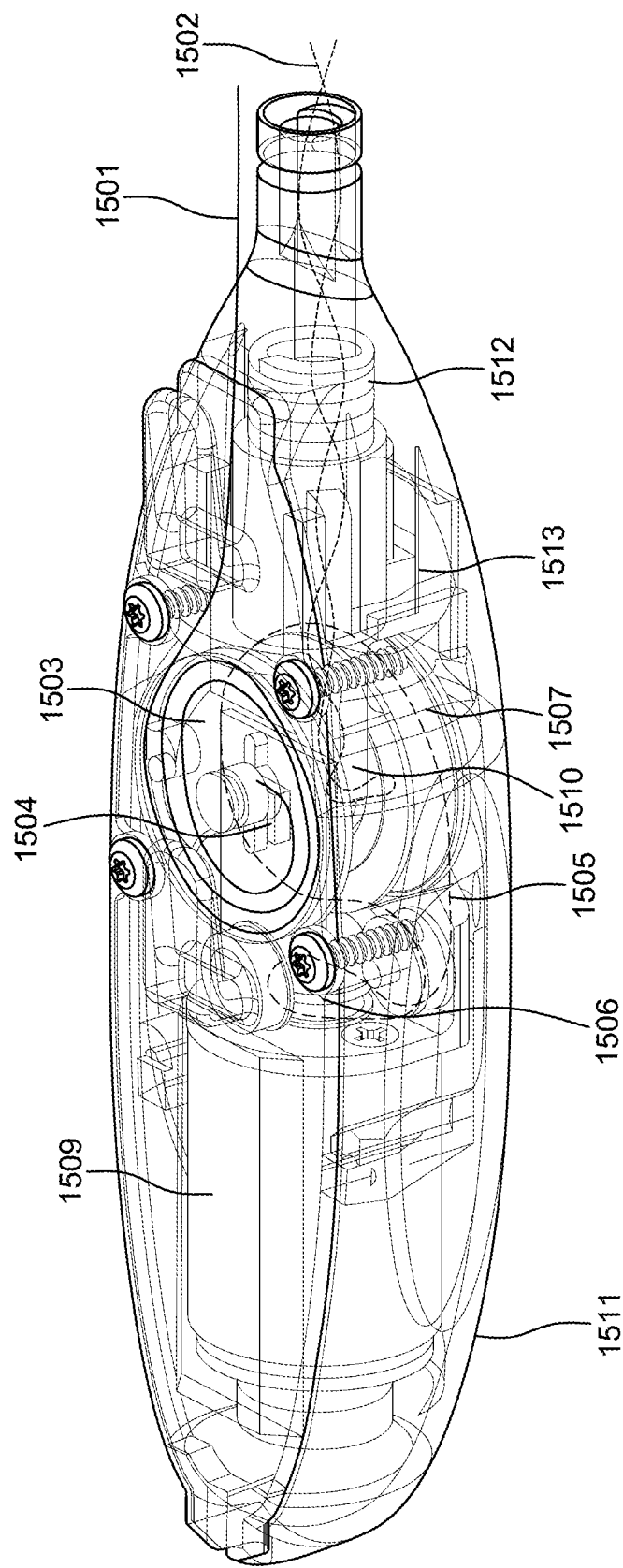
FIG. 15 shows a TSA configuration with o-ring drive and length-sensing according to some embodiments of the present disclosure.

FIG. 15 illustrates TSA 1500 according to some embodiments of the present disclosure. In some embodiments, TSA 1500 includes the features described above, as well as absolute length sensing. Length sensing is achieved with a string or cord (1501) configured substantially in parallel with the effective longitudinal axis of the twisted string pair (1502). One end of the string or cord (1501) is wound around a spring-loaded reel (1503). The opposite end (not shown) of the string or cord (1501) is anchored to or near the opposite end of the FLA (which TSA 1500 is a component thereof). As TSA 1500 is actuated or deactivated, causing the overall length of the twisted string pair 1502 to lengthen or shorten, the string or cord (1501) is pulled from or retracted onto the spring-loaded reel (1503). A rotational sensor (1504) such as a rotary encoder, hall effect sensor, potentiometer or the like detects rotation of the reel (1503). The sensors and controls layer is then able to utilize the signal from the rotational sensor (1504) to calculate absolute length of the TSA, which may be an important parameter for control algorithms used to operate the power layer.

As in previous examples, an o-ring or flexible belt (1505) loops around an input pulley (1506) and output pulley (1507), as well as idler pulleys (1508). The input pulley (1506) is driven by a motor (1509), while the output pulley (1507) twists the twisted string pair (1502), which follows a contoured bearing surface (1510). The o-ring transmission and contoured bearing surface allow the motor and pulleys to be configured in an optimal or minimal profile within a housing or enclosure (1511), with a significant transmission ratio and minimal noise. A spring (1512) between the housing (1511) and output pulley (1507) and displacement sensor (1513) permit measurement of the tensile force generated by the TSA, as described previously.

Figure 16:
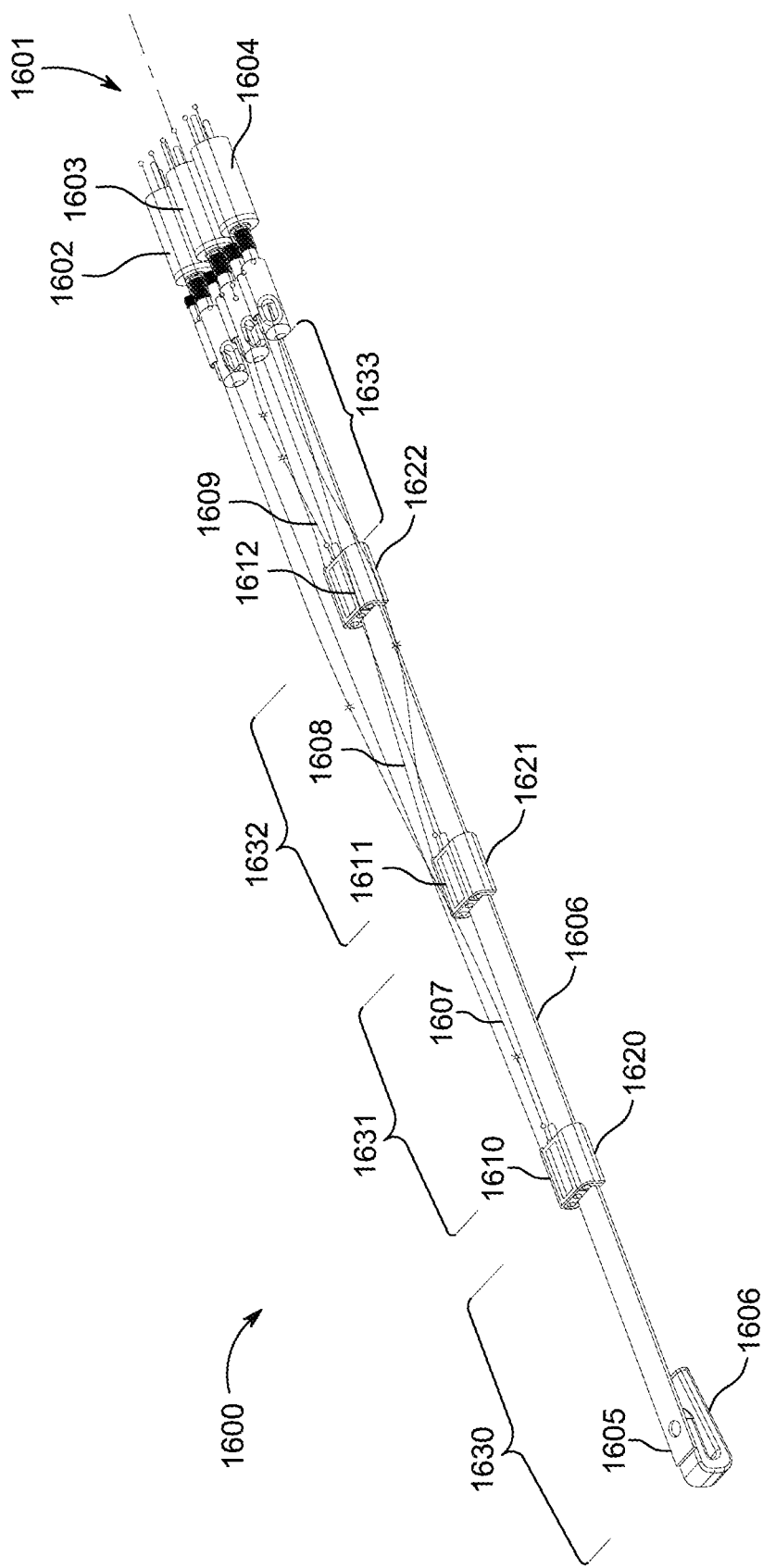
FIG. 16 shows a TSA configured with phased actuators and clutching elements according to some embodiments of the present disclosure.

FIG. 16 illustrates TSA 1600 with phased actuators according to some embodiments of the present disclosure. TSA 1600 has a first end (1601) with first, second and third powered actuators (1602, 1603, 1604, respectively). TSA 1600 has a second end (1605) with an anchor (1606), which is a hook in this embodiment. The first, second and third powered actuators (1602, 1603, 1604) are attached to first, second and third twisted string pairs (1607, 1608, 1609), which are in turn attached at the opposite ends to first, second and third clutching elements (1610, 1611, 1612), respectively. Clutching elements 1610, 1611, and 1612 may be electrolaminate clutches, or other electrical or mechanical clutches. Electrolaminate clutches may provide superior clutching strength with minimal power requirements for a clutch of a given size. First end 1601 and second end 1605 are joined by a telescoping tensile member (1613), with the clutching elements (1610, 1611, 1612) located at telescoping joints 1620, 1621, and 1622, respectively. Tensile member 1613 can include telescoping joints 1620-1622 and segments 1630-1633.

TSA 1600 allows phased actuation of powered actuators 1602-1604 and their respective twisted string pairs 1607-1609, for optimized speed, stroke length or force. For example, in a first phase, the first powered actuator (1602) is actuated. This results in twisting first twisted string pair 1607, and causes first telescoping joint 1620 to collapse. When first twisted string pair 1607 has been shortened to a desired or maximum amount, the first clutching element (1610) is activated to fix the first telescoping joint of the tensile member (1613). Next, the second actuator (1603) twists the second twisted string pair (1608) to shorten by a desired amount, when the second clutching element (1611) is actuated to lock the second telescoping joint of the tensile member (1613). This process is repeated for the third actuator (1604), twisted string pair (1609) and clutching element (1612) such that the stroke length of the TSA is the sum of the stoke lengths of all three twisted strings and actuators. The clutching elements allow the actuators to be operated in sequence, while the twisted string pairs that are not being actuated at that moment remain unloaded. This minimizes power requirements or the actuators being back-driven when they are not active. It can easily be recognized that such a phased actuator system may be configured with more or less actuators in parallel or in series, optimized to the specific requirements of the system.

The TSAs discussed above may be used as part of the FLAs that are incorporated in various exosuit embodiments. In some embodiments, for a given exosuit, each FLA may use the same type of TSA. In another embodiment, the FLAs for a given exosuit may use a different combination of TSAs. For example, hip extensor FLAs may use TSA 1400 and the hip flexor FLAs may use TSA 1500. In yet another example, hip extensor FLAs may use a mixture of TSAs 1000, 1100, 1200, 1300, 1400, and 1500. The FLAs may be constructed to have lengths ranging between six and twenty-four inches, with different stroke lengths.

Figure 17:
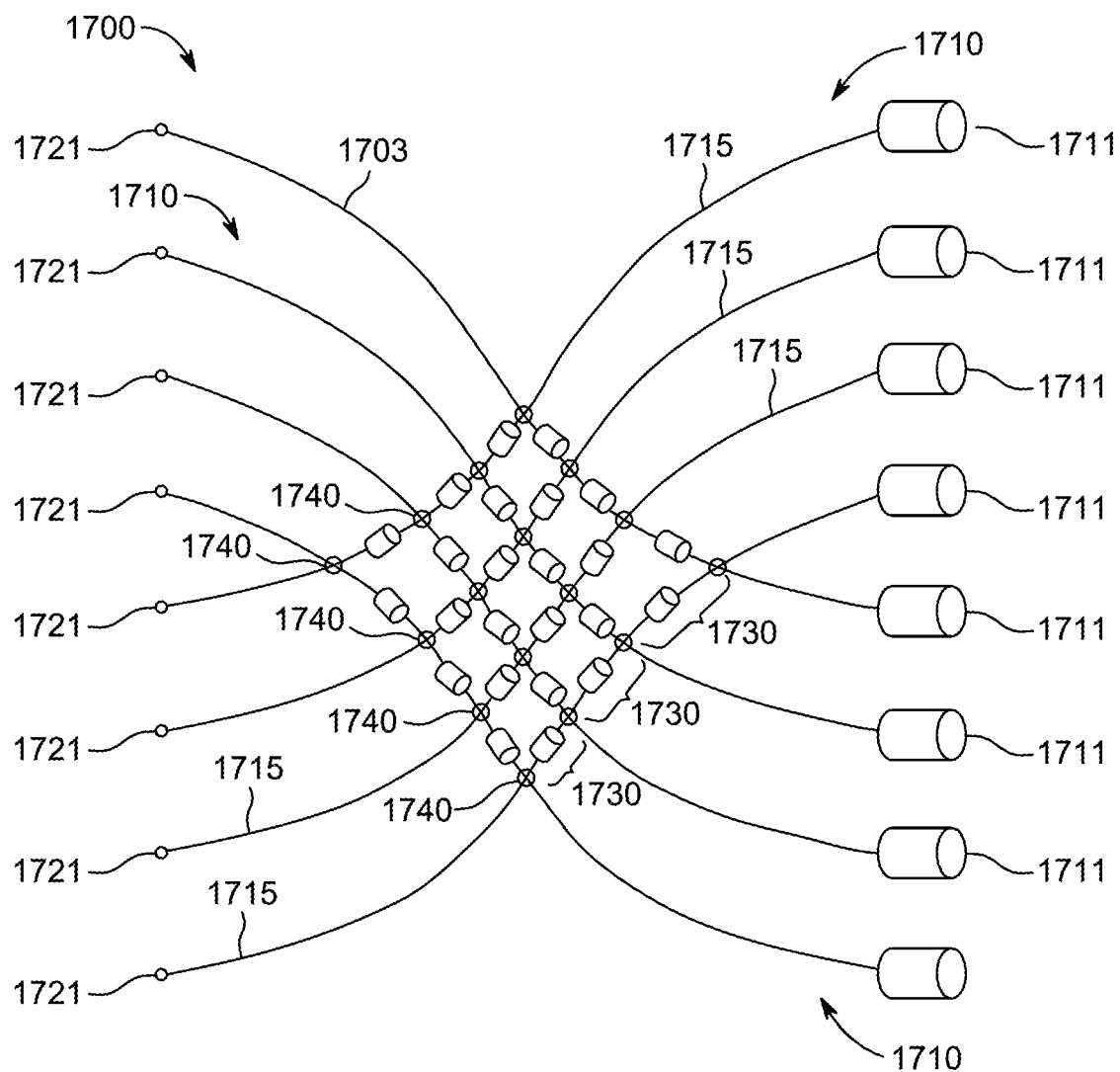
FIG. 17 shows an array of FLAs and clutching elements according to some embodiments of the present disclosure.

FIG. 17 illustrates FLA array 1700 according to an embodiment. Array 1700 may include a web of FLAs and clutching elements that operate together to provide optimized load distribution over a surface (of human anatomy). Array 1700 may be contoured for specific applications. For example, array 1700 may follow catenary curves or other paths similar to that of a load distribution member. In some embodiments, array 1700 may be used as a load distribution member.

FLA array 1700 may include several primary FLA strings 1710 that span from a motor 1711 to an anchor point 1721. Motor 1711 and anchor point 1721 may be secured in place to the exosuit (e.g., such as to one or more load distribution members). Motor 1711 may be a twisted string actuator (e.g., TSA 1000, 1100, 1200, 1300, 1400, and 1500) Each primary FLA strings 1710 can include a twisted string 1715 and one or more secondary FLAs 1730 that are connected in series with twisted string 1715 between motor 1711 and anchor point 1721. Primary FLA strings 1710 may be arranged to overlap each other to form an array or web of primary FLAs 1710 and secondary FLAs 1730. Nodes 1740 may exist at each intersection of the primary FLA strings 1710, including intersections among secondary FLAs 1730. Nodes 1740 may include sliding or guide elements to facilitate actuation of the FLAs across the intersections. Nodes 1740 may be fixed to the exosuit (e.g., the base layer), or may be free to move relative to exosuit (e.g., the base layer). Nodes 1740 may include clutching elements (e.g., such as an electrolaminate clutch or mechanical clutch). Engagement of the clutching elements can lock relative movement of FLAs 1710 and 1730 at that node, reducing power requirements to maintain desired segment distances, which are controlled by secondary FLAs 1730.

In some embodiments, all or a portion of array 1700 may travel through defined channels within an exosuit (e.g., the base layer), or may be free to move relative to the base layer. For example, each string 1715 may travel through channels or tubes existing on the exosuit. The channel or tube may be perforated with openings to allow other strings 1715 to interface to the string traveling through the channel or tube. FLAs 1730 may exist within the channel or tubes. Nodes 1740 may exist near the perforations.

Secondary FLAs 1730 can include a motor and a twisted string, where the motor is connected to one of nodes 1740 and the twisted string, and the twisted string is connected to another node 1740. With this arrangement, each secondary FLA 1730 forms a movable segment within FLA array 1700 that can independently shorten or lengthen its segment distance.

Each of primary and secondary FLAs 1710 and 1730 can be independently controlled to manipulate tension within FLA array 1700. In one embodiment, primary FLAs 1710 may provide coarse tension adjustments within array 1700 and secondary FLAs 1730 may provide fine tension adjustments within array 1700. Activation of motor 1711 in any primary FLA 1710 may manipulate the path of its twisted string 1715 relative to the other twisted strings. Activation of the motors associated with secondary FLA 1730 may manipulate a localized segment of the twisted string it is in series with. Thus, actuation of different FLA segments (via FLAs 1710 and/or 1730) within the array can generate forces and contractions in an exosuit that are optimally contoured for specific activities or body types. Selective actuation of FLAs 1710 and 1730 within the array may also distort or change the overall size of the array, in order to adapt to the wearer's body.

In some embodiments, FLA array 1700 can include as many primary and secondary FLAs 1710 and 1730 and clutches as necessary to perform the actions required of the exosuit. For example, FLA array can include dozens, hundreds, or thousands of individual primary and secondary FLAs and clutches. In one embodiment, the entire exosuit, or a relatively large portion thereof, can be one large FLA array 1700. In another embodiment, the exosuit can include multiple FLA arrays 1700. Regardless of whether the exosuit contains one or several FLA arrays 1700, FLA arrays 1700 can be controlled to provide assistive movements in accordance with embodiments discussed herein. For example, FLA array 1700 can provide hip flexor, hip extensor, and spinal extensor assistive movements, or any other muscle assistive movement. In some embodiments, FLA array 1700 can provide the user with a massage. In some embodiments, FLA array 1700 may serve as a load distribution member in the exosuit. In some embodiments, FLA array 1700 may serve double duty as both a load distribution member and a muscle movement assistant.

Figure 18:
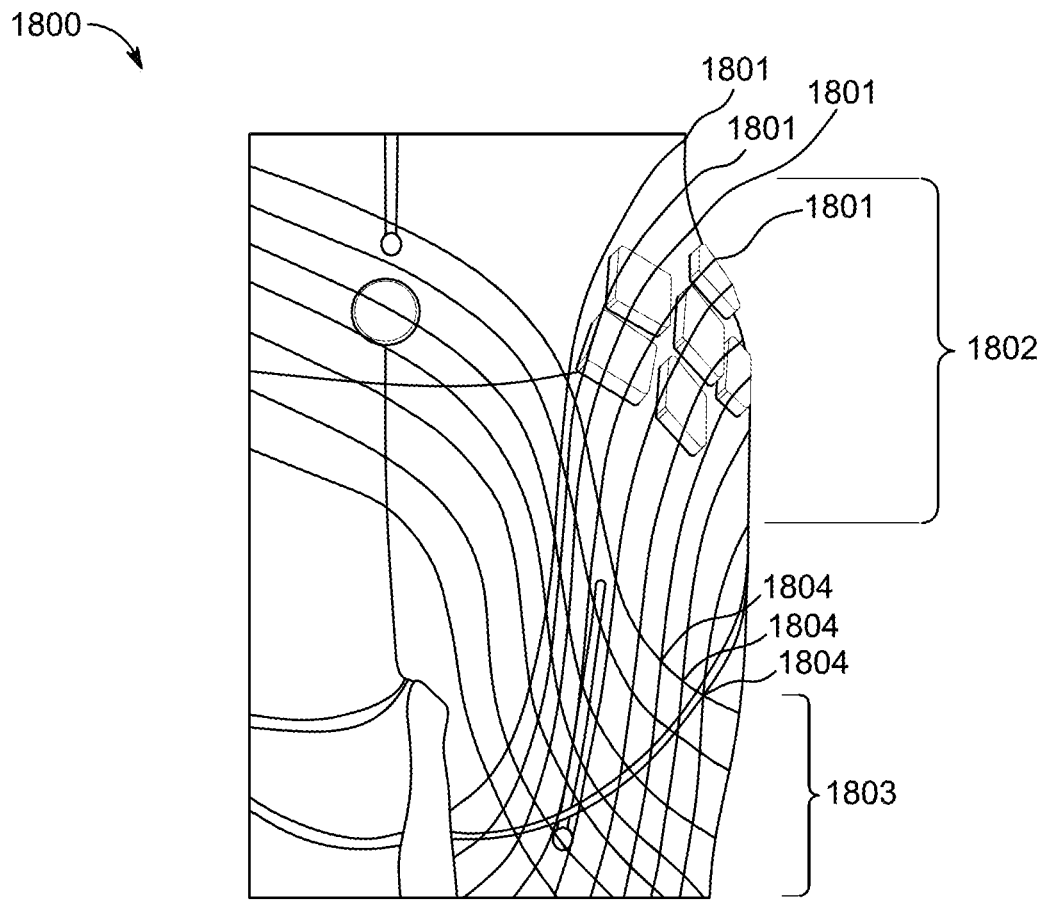
FIG. 18 shows an application of an array of FLAs and clutching elements according to some embodiments of the present disclosure.

FIG. 18 shows an illustrative example of FLA array 1800 being used as part of an exosuit according to an embodiment. FLA array 1800 may be similar to FLA array 1700. As shown in FIG. 18, FLA array 1800 is configured analogously to a hip extensor or gluteal muscle. FLA array 1800 is arranged along paths (1801) similar to that of a load distribution member. Each path 1801 may include a primary FLA and one or more secondary FLAs (not shown). The paths may approximate catenary curves to minimize or optimally distribute pressures and forces along the exosuit and wearer's body. In this example, upper portion 1802 of array 1800 originates around the waist and hips, and lower portion 1803 of array 1800 terminates around the thigh. As described previously, paths 1801 intersect at nodes 1804. Selective actuation of FLAs and/or clutching elements within the array may generate forces that assist the user in desired activities, such as moving from a seated to standing position, walking, lifting and the like, while evenly distributing the forces around the exosuit and wearer's body, as well as adapt the suit to the specific anatomy and geometry of the wearer's body. As described previously, the powered actuators such as motors may be engaged at the edges of the array at the ends of the paths 1801, or within the array along segments of the paths. Clutching elements at the nodes 1804 may selectively inhibit motion of specific paths, depending on the function or activity performed.

Figure 19A:
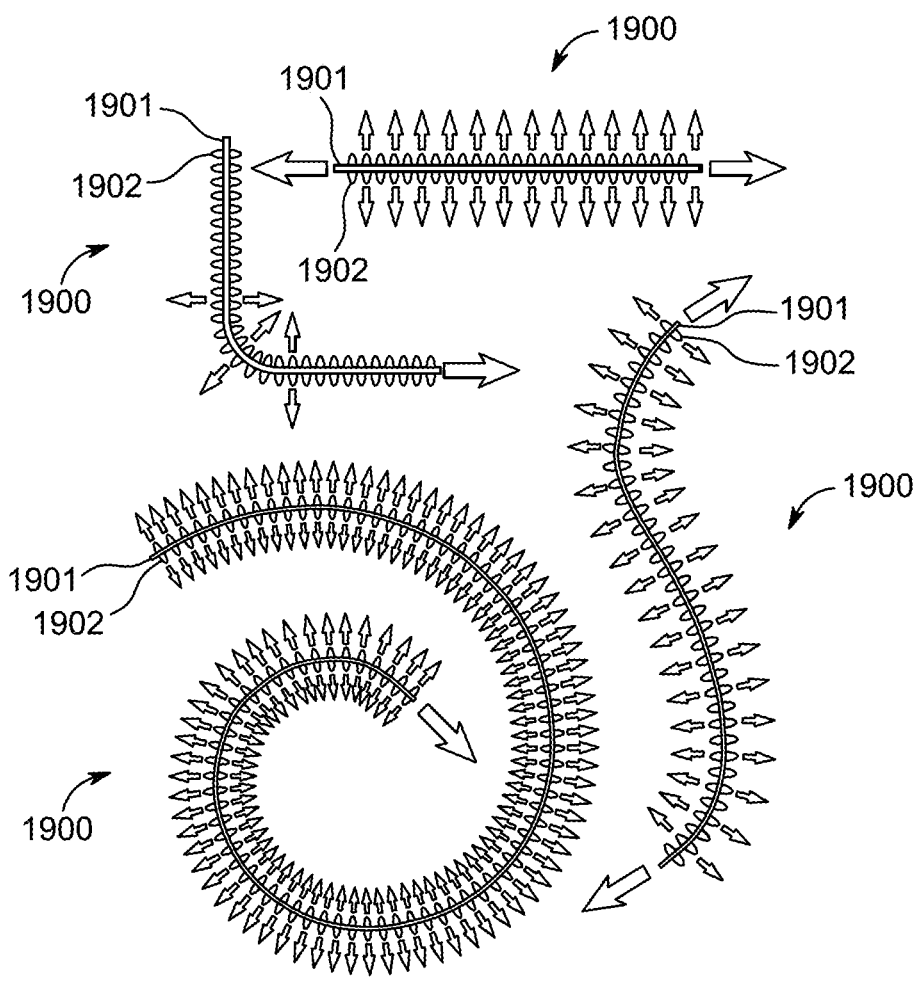
FIG. 19A illustrates possible configurations of a load distribution strap according to some embodiments of the present disclosure.

FIG. 19A illustrates possible configurations of load bearing strap 1900 according to some embodiments of the present disclosure. One or more load bearing straps 1900 may be used to create an extensively or infinitely configurable load distribution member. Load distribution strap 1900 may enable loads (shown by the arrows) to be distributed over any curved or straight path. For example, load bearing straps 1900 are shown in the exosuit of FIGS. 8A and 8C. Load bearing strap 1900 may include a longitudinal cord 1901 with tabs 1902 attached to cord 1901. The diameter of cord 1901 and the size and shape of tabs 1902 may be selected to achieve desired bending direction(s) and dimensions of a shape obtained through the bending. For example, a thinner diameter cord 1901 may permit strap 1900 to be moved into a smaller circumference curve than a larger diameter cord.

Any suitable shape of tabs 1902 may be used. Tabs 1901 assist with distribution of force while enabling strap 1900 to remain relatively flat. For example, the tap shape may be ovular, circular, rectangular, tooth shaped, or key stone shaped. Tabs 1902 may be shaped to control the direction in which strap 1900 can be moved. For example, as shown, tabs 1902 are ovular in shape. The ovular shape enables strap 1900 to be moved both directions (up and down or side-to-side) relative to cord 1901. A key stone or tooth shaped tab may limit movement of strap to one direction relative to cord 1901.

Figure 19B:
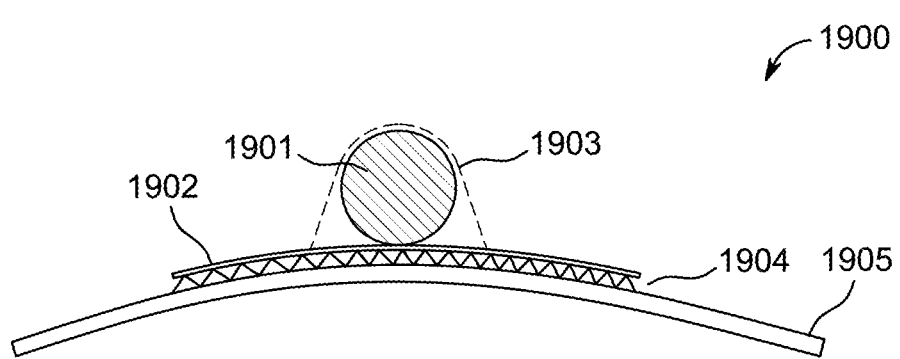
FIG. 19B illustrates a cross section of a load distribution strap according to some embodiments of the present disclosure.

FIG. 19B illustrates a cross section of load bearing strap 1900. Longitudinal cord 1901 can secured to the pads 1902 with stitches 1903 (or an adhesive). Hook and loop fasteners 1904 may exist on a bottom surface of pads 1902 and are operative to releasably attach pads 1902 to substrate 1905, which may be, for example, an exosuit base layer. The flexibility and releasably attachment capability can enable one or more straps 1900 to be repeatedly re-configured to produce load distribution member that is optimize for improved comfort and function. In some embodiments, strap 1900 can be coupled to substrate 105 by way adhesives, stitching, or other type of adherence.

Figure 20A:
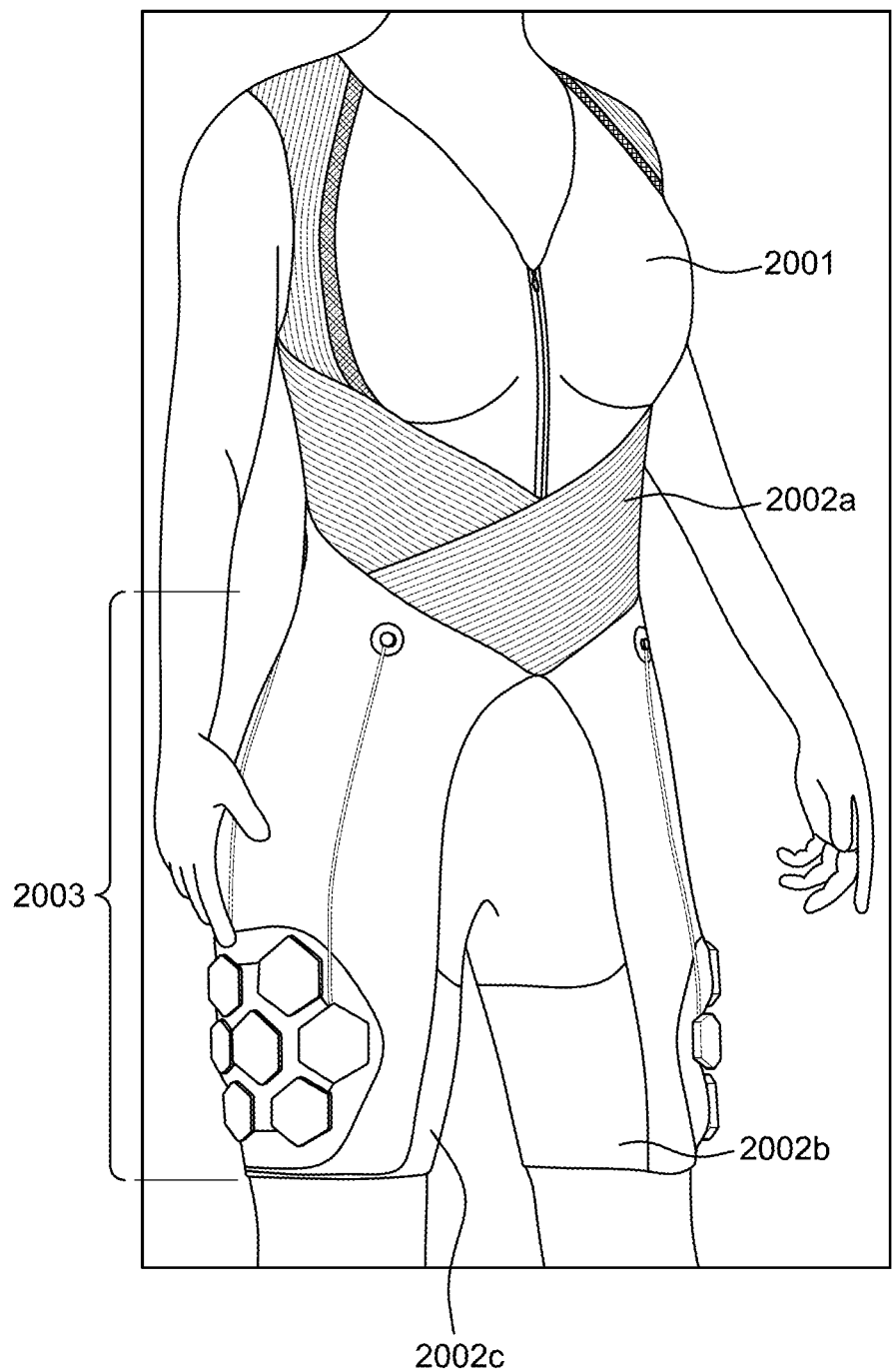
FIG. 20A Shows a front-right oblique view of an undergarment assistive exosuit with modular components according to certain embodiments of the present disclosure.
Figure 20B:
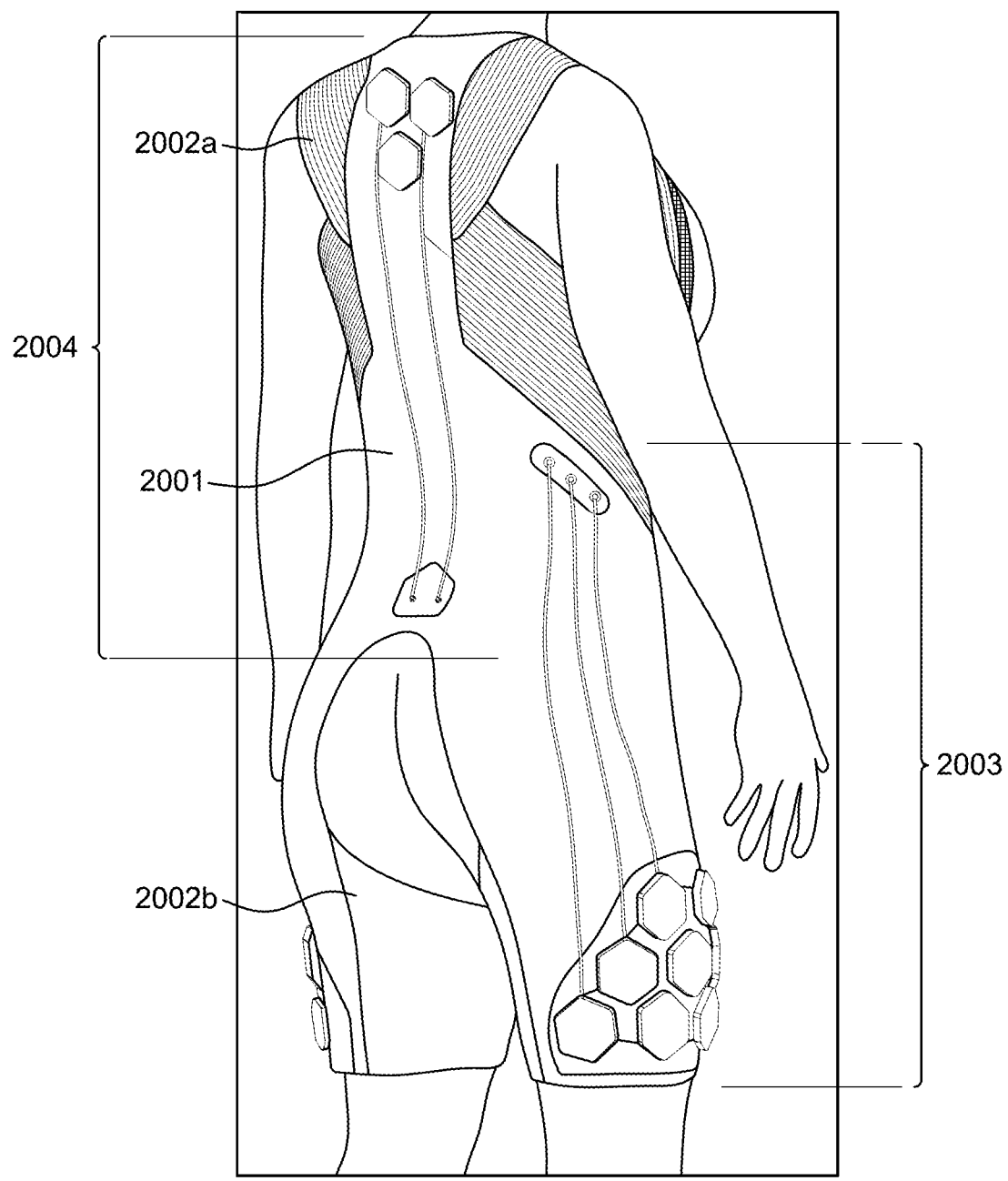
FIG. 20B shows a back-right view of an undergarment assistive exosuit with modular components according to certain embodiments of the present disclosure.

FIGS. 20A-20B show an illustrative undergarment assistive exosuit (UAE) system 2000 with modular components, according to an embodiment. As discussed above in connection USAE 900, the modular components are designed to be removed from the base layer of the suit. As shown in FIGS. 20A and 20B, UAE 2000 includes base layer 2001 with integral load distribution members 2002a, 2002b, and 2002c. Load distribution member 2002a may wrap around the torso such that it covers the abdomen, upper back, and shoulders. Load distribution members 2002b and 2002c may wrap around the thighs. Modular patch assemblies 2003 and 2004 are attached to the base layer, such that they are anchored to the load distribution members 2002a, 2002b, and 2002c. In particular, one of modular patch assemblies 2003 may be anchored to load distribution members 2002a and 2002b, and the other module patch assembly 2003 may be anchored to load distribution members 2002a and 2002c. Modular patch assembly 2004 may be anchored to the upper back/lower neck region of load distribution member 2002a and to the lumbar region of load distribution member 2002a.

Figure 20C:
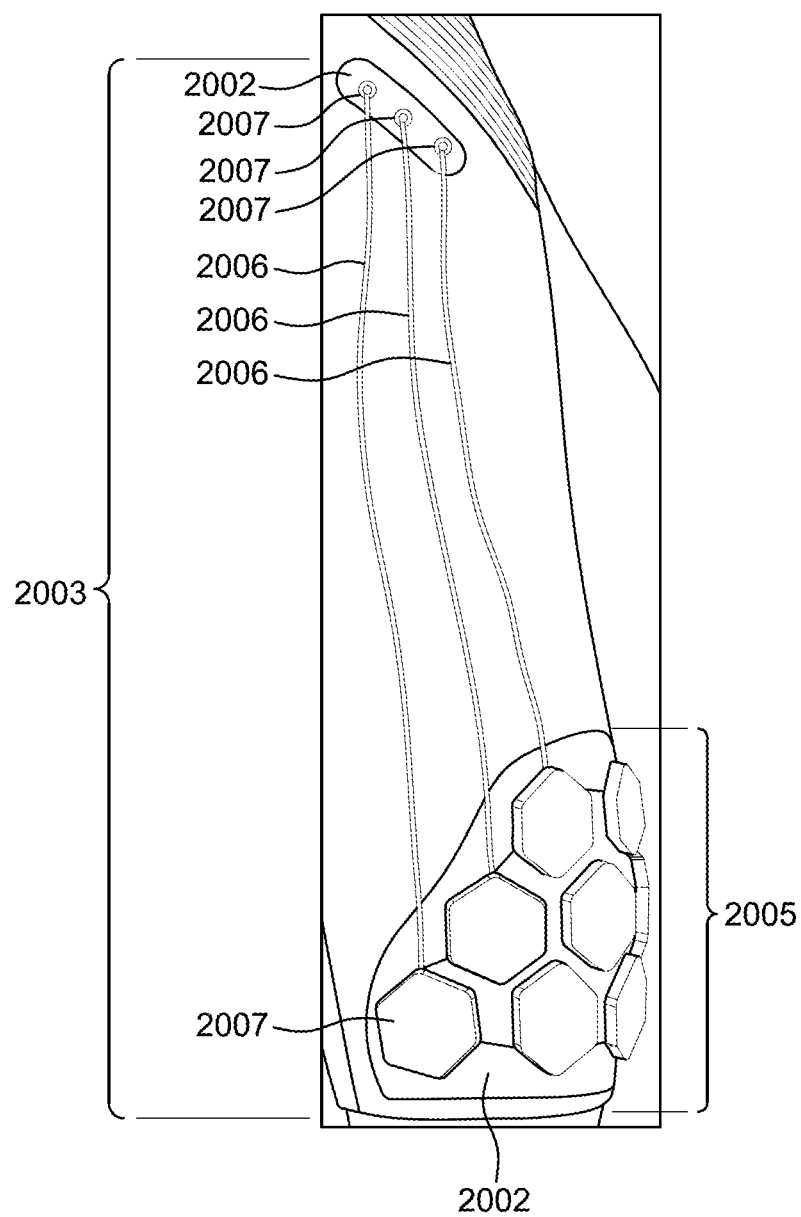
FIG. 20C shows a detail view of modular components of an undergarment assistive exosuit according to certain embodiments of the present disclosure.

FIG. 20C shows a detailed view of modular patch (2003), which includes FLAs corresponding to hip extensors. Modular patch 2003 can include a tessellated array of housings 2005 containing components of the power layer, such as motors, transmission components, force sensing transducers, electronic control and communication systems, batteries and the like. Housings 2005 may be inseparable from the patch, or modularly removable and replaceable. Housings 2005 may anchor to load distribution member 2002b or 2002c. As shown, three of housing 2005 may include components of a FLA such as the motor unit that is attached a twisted string that runs through one of tubes 2006 to one of anchor points 2007 located on load distribution member 2002a. Anchor points 2007 may be detachably coupled to load distribution member 2002a and serve as an anchor for each the twisted strings. Thus, when the motor in the FLA is actuated, it twists the string to provide a force tension that pulls load distribution member 2002a toward load distribution member 2002b. When modular patch 2003 is removed, the entirety of housing 2005, tubes 2006, and anchor points 2007 are removed from base layer 2001. Module patch 2004 can include an arrangement similar to modular patch 2003 and may also be removed in its entirety.

In some embodiments, modular patches 2003 and 2004 may be used to contain all electronics, FLAs, and there components associated with the power layer. The modular patches may be removable to permit washing of the base layer. The modular patches may serve as an interface to the load distribution members (integrated within the base layer). This interface may support operation of FLAs to provided hip flexor, hip extensor, or spinal extensor assistive movements. The modular patches may pass-through openings that enable components (e.g., FLA components) to anchor directly to load distribution members. In addition, the modular patches may serve as its own load distribution member-like structure to support weight of batteries and circuit boards, sensors, electronics, etc.

In some embodiments, the components of UAE system 2000 can have other suitable location, shape, number, and/or arrangement. For example, although FIG. 20C shows housing 2005 has having a hexagon shape, any other suitable shape can be used. Housing 2005 can have any suitable number, location, and/or arrangement.

Figure 21:
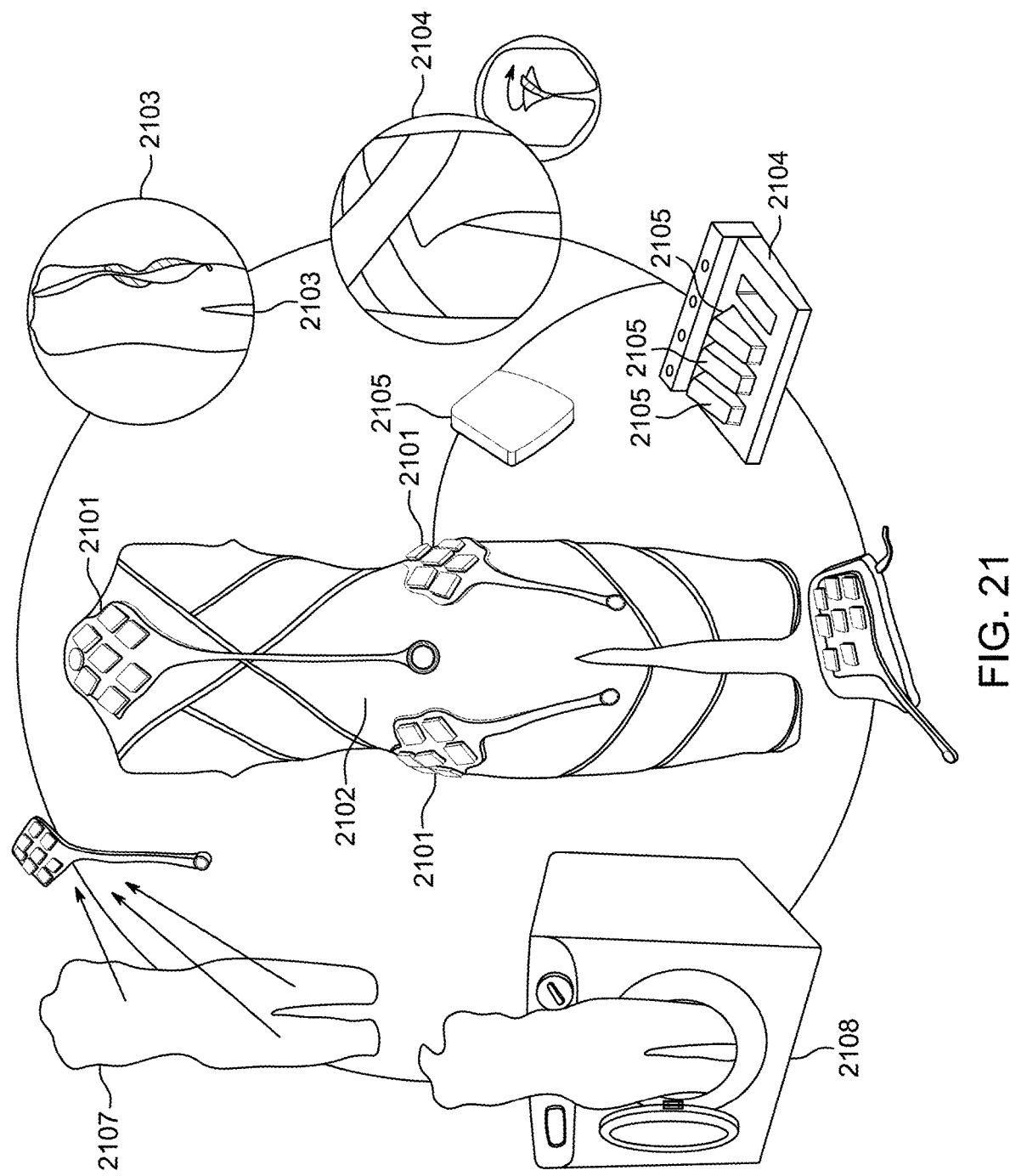
FIG. 21 illustrates an embodiment of an undergarment assistive exosuit with modular patches and various use scenarios.

FIG. 21 illustrates an embodiment of an undergarment assistive exosuit with modular patches and various use scenarios. Modular patches (2101) representing hip extensor and spinal extensor muscles are attached to a base layer (2102). Modular patches 2101 may be removed at process step 2107 to facilitate donning and doffing the exosuit at process step 2103, or to use the toilet at step 2104 or to clean the suit at step 2108. In connection with cleaning step 2108, removal of modular patches 20101 can enable the base layer to be machine washed without damaging electronic components. One or more battery packs 2105 may be removed from a modular patch or other location on the suit to be replaced or charged, for example in a charging station 2106.

Modular patches and components may be removed and replaced, e.g. for cleaning, servicing, exchanging or charging batteries, or to replace with different components such as flexdrives with different strength, speed, or weight. The modular components may also enable configuration of a suit for a specific individual, based on their specific body size, weight, and functional requirements. For example, the base layer may be selected from a group of sizes or styles, or custom made, to provide the features desired by the wearer. Features may include donning and doffing features, adjustments, pockets, or other functional or aesthetic features. The suit may then be configured with modular patches appropriate to the individual user. Configurable aspects of the modular patches may include power, strength, speed, weight and size of the flexdrives, battery capacity, communication capability, user interface features or the like.

Figure 22A:
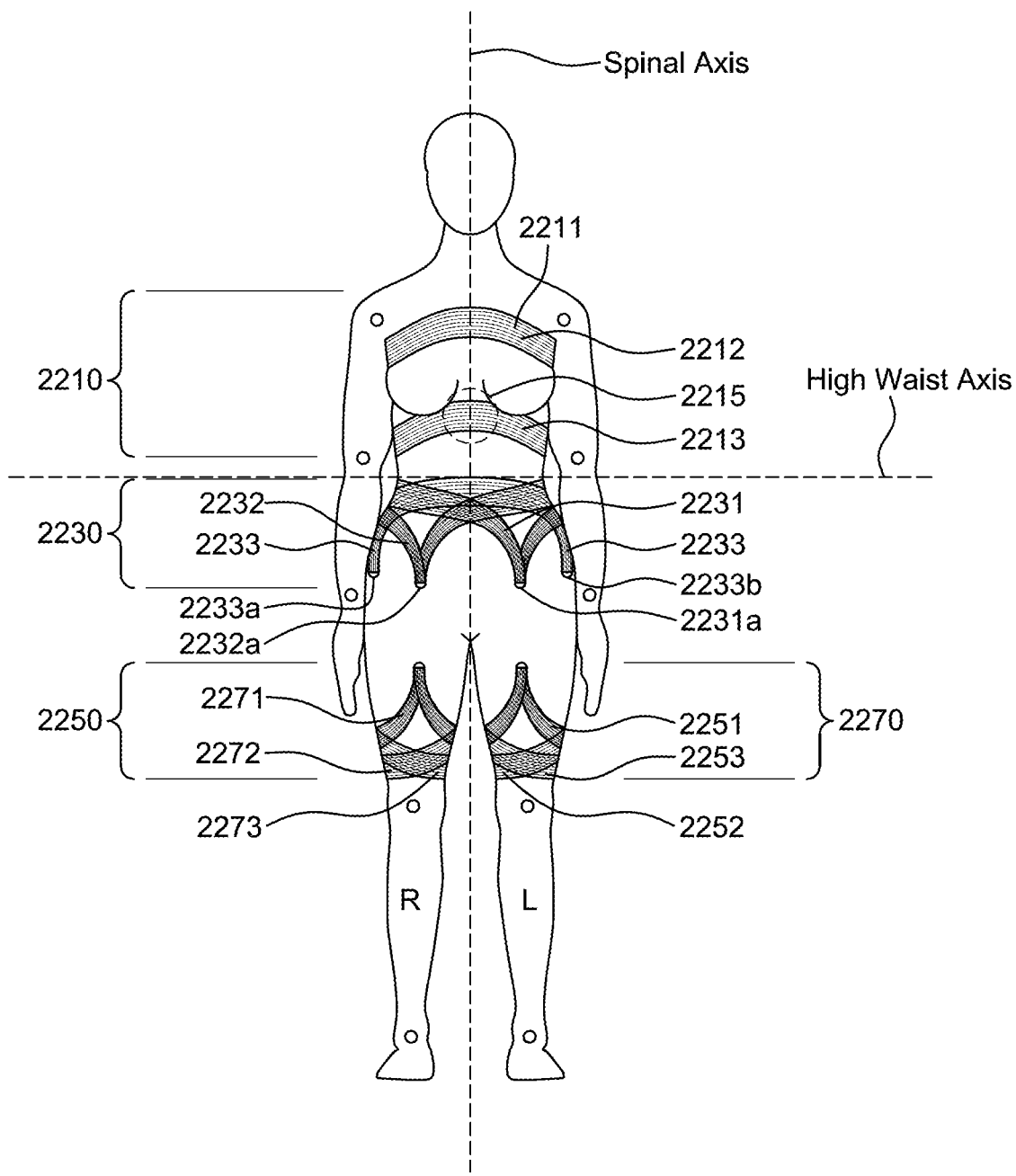
FIGS. 22A-22C show front, back, and side views of several different load distribution members positioned on different locations of a human body.
Figure 22B:
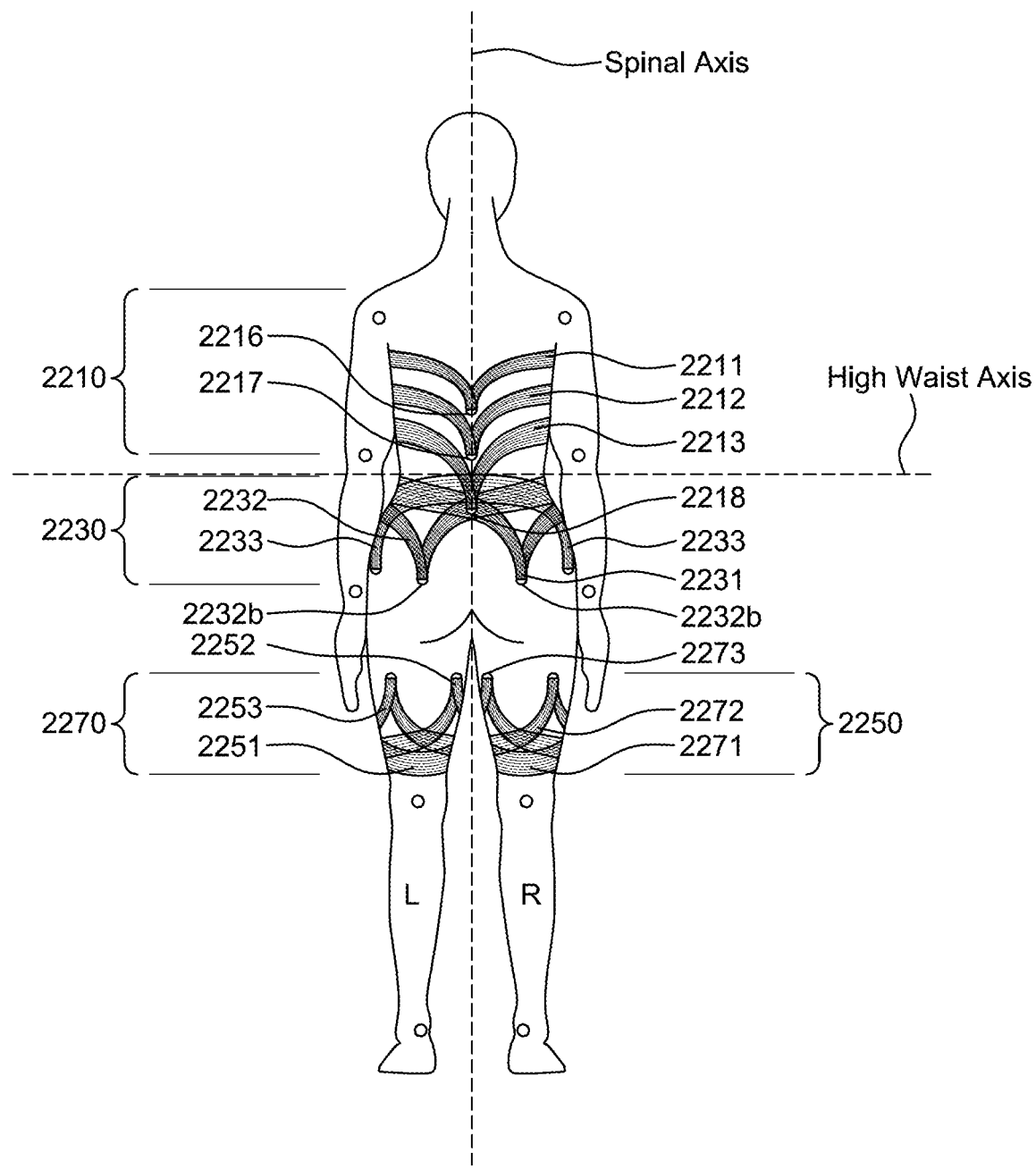
Figure 22C:
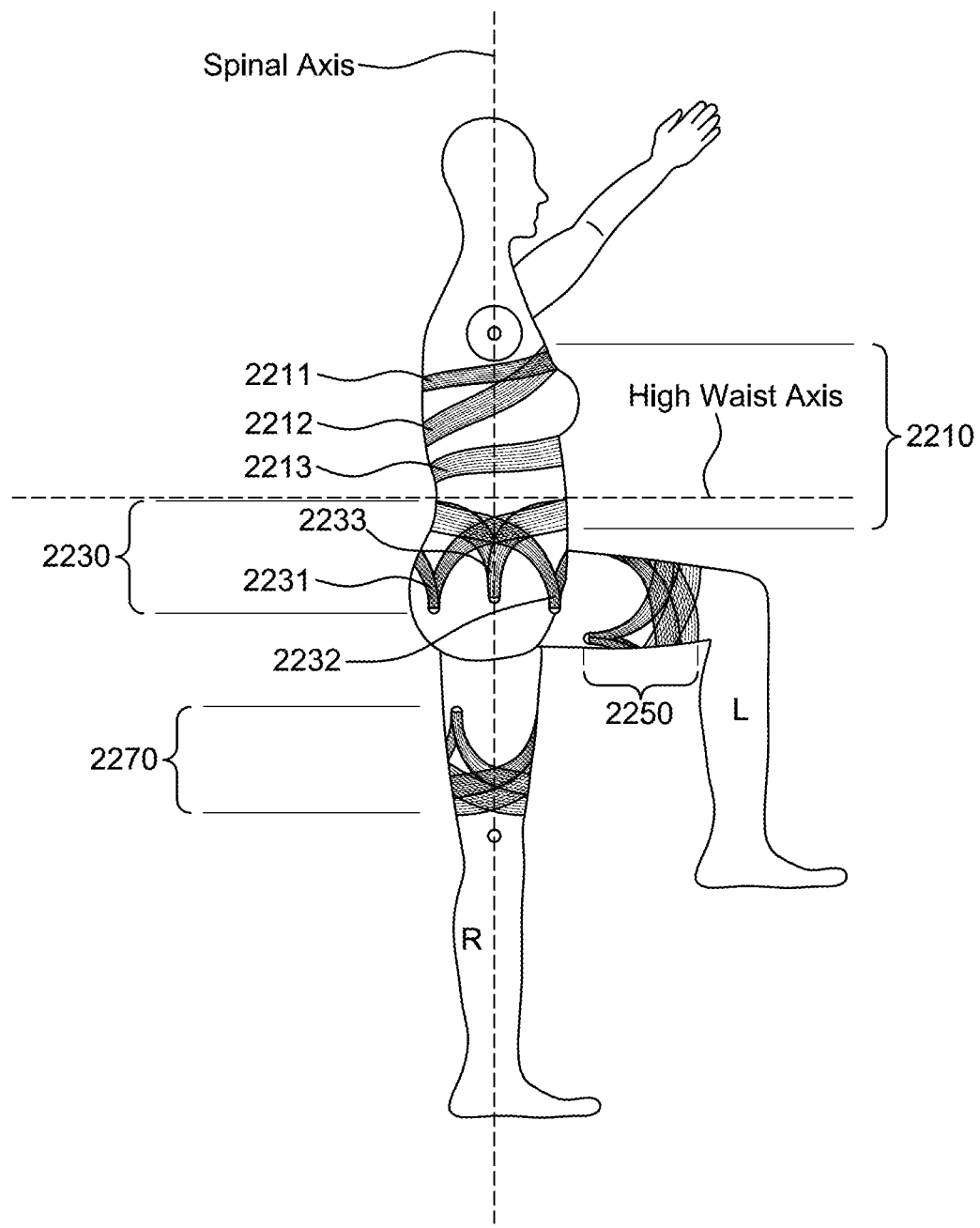

FIGS. 22A-22C show front, back, and side views of several different load distribution members positioned on different locations of a human body. FIGS. 22A-22C will be collectively referred to herein during description of the load distribution members. The load distribution members include torso load distribution member 2210, pelvis load distribution member 2230, and thigh load distribution members 2050 and 2070.

Torso load distribution member 2210 can include inextensible members 2211-2213 that stem from spine region on the back of the body and encircle the body above and below the peck/breast region of the chest. Anchoring points 2216-2218 may be attached via an attachment member (not shown). Members 2211-2213 form grip lines that represent catenary curves that distribute load around the torso when subjected to a loading event (e.g., spinal extensor assistive movement). Although members 2211-2213 are general inextensible, member 2213 may include stretch portion 2015 located near the sternum/breast bone. Stretch portion 2015 may facilitate easier breathing by enabling the diaphragm to stretch the stretch portion 2015 during inhalation. Stretch portion 2015 may be stretch limited so that tension in member 2013 is maintained during loading. Members 2211-2213 may be arranged and positioned such that they do not encircle the area between the lower ribs and the high natural waist, which is located near the belly button. Shoulder straps are not shown in FIGS. 22A-22C, but it should be appreciated that shoulder straps may be attached to one or more of members 2211-2213 to provide additional stability for torso load distribution member 2210.

Pelvis load distribution member 2230 distributes load around the hips and serves as an anchor for FLAs attached between member 2230 and any one or more of members 2210, 2250, and 2270. Member 2230 can include members 2231-2233 that wrap around the pelvis/hip region of the body. Each of members 2231-2233 can employ catenary curves to better distribute the load below the natural waist (below the belly button) and above the lower hips. The catenary curves are represented by the v-shapes in members 2231-2233. Each of members 2231-2233 can include v-shapes, the points of which can be anchor points. Each of member 2231-2233 can include two anchors, which are positioned on opposite sides of the body. The grip line arrangement of members 2231 and 2232 counterbalance each other by crossing each other around the body. For example, member 2231 can include anchor points 2231a (which is positioned next to the left thigh) and 2231b (which is position next to the right hip), member 2232 can include anchor points 2232a (which is positioned next to the right thigh) and 2232b (which is positioned next to the left hip). Member 2233 can include anchor points 2233a (which is positioned next to the right hip) and 2233b (which is positioned next to the left hip).

Thigh load distribution members 2250 and 22270 distribute loads around their respective thighs and serve as anchors for FLAs attached between member 2210 and members 2250 and 2270. Member 2250 can include members 2251-2253 that wrap around the left thigh. Member 2270 can include members 2271-2273 that wrap around the right thigh. Each of members 2251-2253 and 2271-2273 can employ catenary curves to better distribute the load around their respective thighs. Anchor points may exist for each of members 2251-2253 and 2271-2273.

Figure 25:
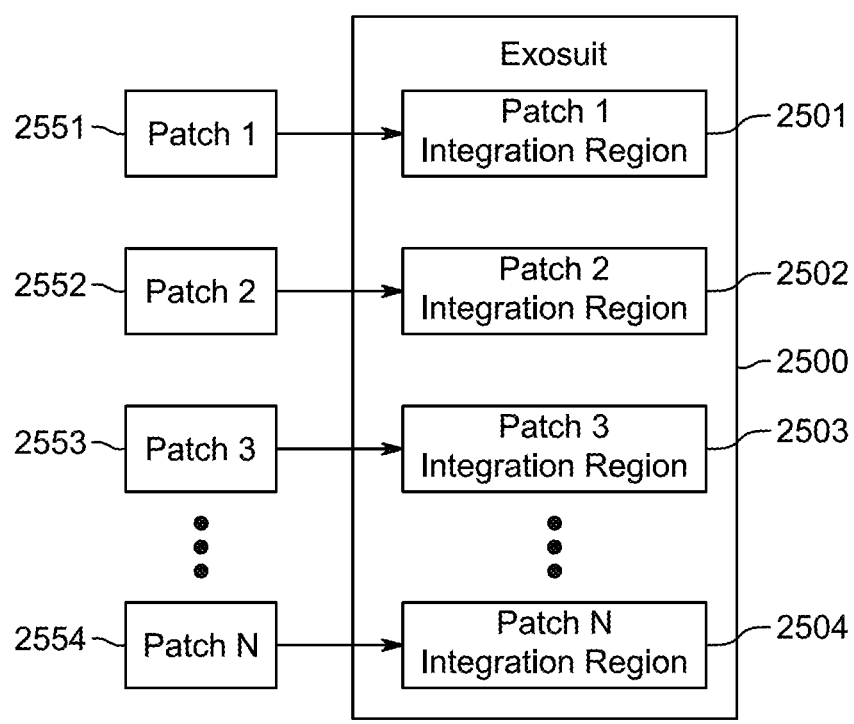
FIG. 25 shows an illustrative block diagram of an exosuit that is constructed to receive patch assemblies in accordance with various embodiments.

FIG. 25 shows an illustrative block diagram of an exosuit 2500 that is constructed to receive patch assemblies 2551-2554 in accordance with embodiments described herein. Exosuit 2500 may include a base layer and load distribution members as described herein. Patch assemblies 2551-2554 are self-contained, self-powered sub-systems that are detachably coupled to exosuit 2500 at respective patch integration regions 2501-2504. That is, patch assemblies 2551-2554 can be secured in place on exosuit 2500 when assistive movements are required and patch assemblies 2551-2554 can be removed from exosuit 2500 (e.g., when exosuit 2500 needs to be washed). Patch integration regions 2501-2504 can represent portions of the exosuit configured to interface with a patch assembly. For example, patch integration regions 2501-2504 may use any suitable attachment mechanisms such as fasteners, loops, buckles, and clips to interface with a patch assembly. The attachment mechanism may be integrated with a load distribution member of the exosuit such that when the FLAs of the patch assemblies are activated, the load distribution members provide the support required to enable muscle assistance movements. Patch assemblies 2551-2554 can be attached to the base layer of exosuit 2500 using a standardized interface that includes harness elements that can be enabled with zippered covers, snaps, or other means of securing the attachment. The standardized interface allows for different size patches to be inserted into the suit, allowing for modularity for the wearer who may want to use different size patches in the same base layer, or for initial evaluation and fitting of a customer. Patch integration regions 2501-2504 may also be standardized so that patch assemblies of varying sizes can be accommodated.

Patch assemblies 2551-2554 may be specifically constructed to only fit in respective patch integration regions 2501-2504. For example, patch assembly 2551 may be a left leg hip flexor patch assembly, which would only fit with the reciprocal left leg hip flexor patch integration region such as patch region 2501. FIG. 25 illustrates that there are N patch assemblies and N patch integration regions. Thus, any suitable number of patch assemblies may be detachably coupled to a respective patch integration region. It should be further appreciated that the detachable coupling between a patch assembly and a patch integration region can include one, two, or three or more attachment points.

In some embodiments, one of the patch assemblies may serve as the master and the remaining patch assemblies may serve as slaves. The master patch assembly may contain core or central processing control electronics that serve as the main nervous center of the exosuit. The master patch assembly may send commands to the slave patch assemblies to execute movement assist functions. The slave patch assemblies may transmit data (e.g., sensor data, telemetry data, motor control data) to the master patch assembly.

Figure 26:
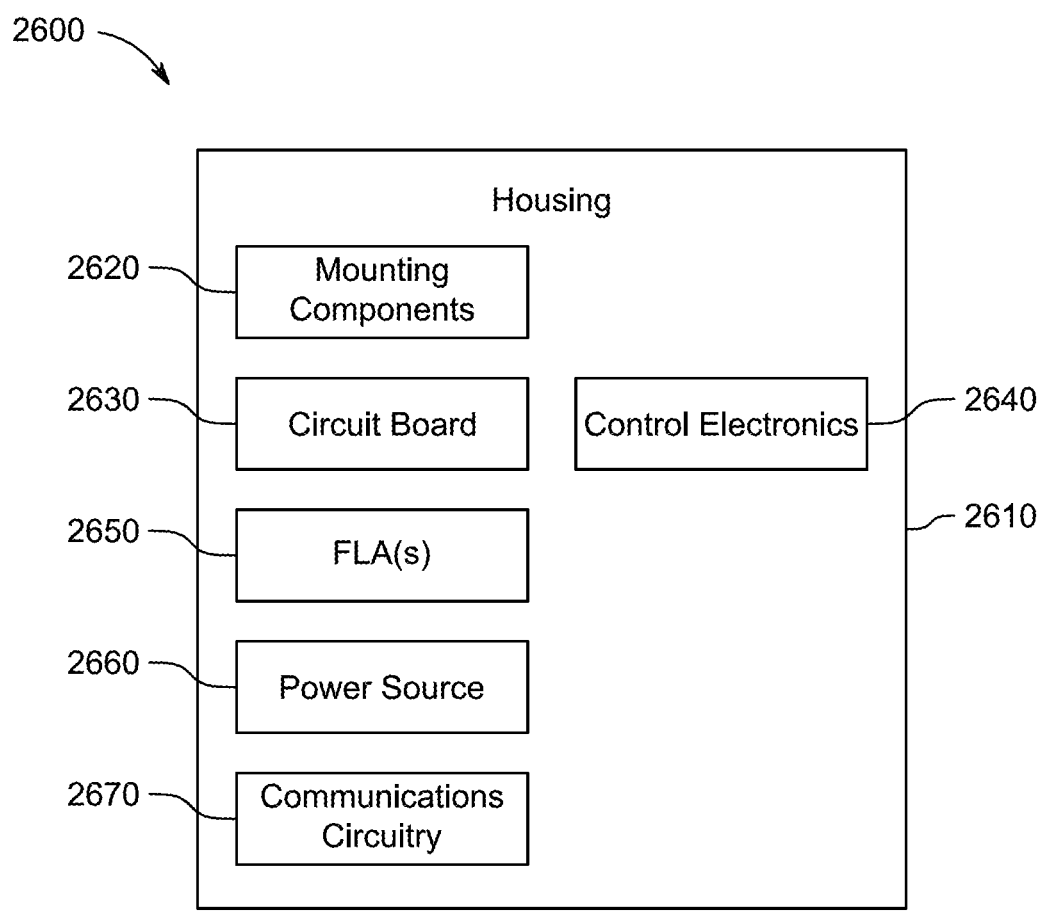
FIG. 26 shows an illustrative block diagram of patch assembly according to an embodiment.

FIG. 26 shows an illustrative block diagram of patch assembly 2600 according to an embodiment. Patch assembly 2600 may represent any one of patch assemblies 2551-2554 and modular patches 2003, 2004, and 2101. Patch assembly 2600 may include housing 2610, mounting components 2620, circuit board 2630, control electronics 2640, FLAs 2650, power source 2660, communications circuitry 2670, and other circuitry (not shown). Housing 2610 may contain or be attached to mounting components 2620, circuit board 2630, control electronics 2640, FLAs 2650, power source 2660, communications circuitry 2670, and other circuitry (not shown). Mounting components 2620 may be responsible to coupling the housing or patch assembly as a whole to the exosuit (e.g., patch integration region). Mounting components 2620 can include any suitable attachment mechanisms such as fasteners, loops, buckles, and clips. Circuit board 2630 can be any suitable circuit board such as a printed circuit board or a flexible circuit board. Circuit board 2630 may provide a substrate for control electronics 2640 to reside and may also provide interconnects for routing power and data signals amount other components such as FLAs 2650, power source 2660, and communications circuitry 2670. Control electronics 2640 can include the electronics for controlling operation of patch assembly 2600, including for example, operation of FLAs 2650, power management, and communications circuitry 2670. FLAs 2650 have been discussed throughout this disclosure and need not be discussed in more detail here. Power source 2660 can include one or more batteries or battery packs that may be removable. Communications circuitry 2670 may include wired and/or wireless communications for communicating with a source remote to patch assembly 2600. For example, communications circuitry may communicate with another patch assembly that functions a master controller. As a specific example, communications circuitry 2670 may receive commands from a remote source that instructs control electronics 2640 to activate FLA 2650. As another specific example, data acquired by one or more sensors (not shown) associated with patch assembly 2600 may be transmitted to a remote source via communications circuitry 2670.

Figure 27:
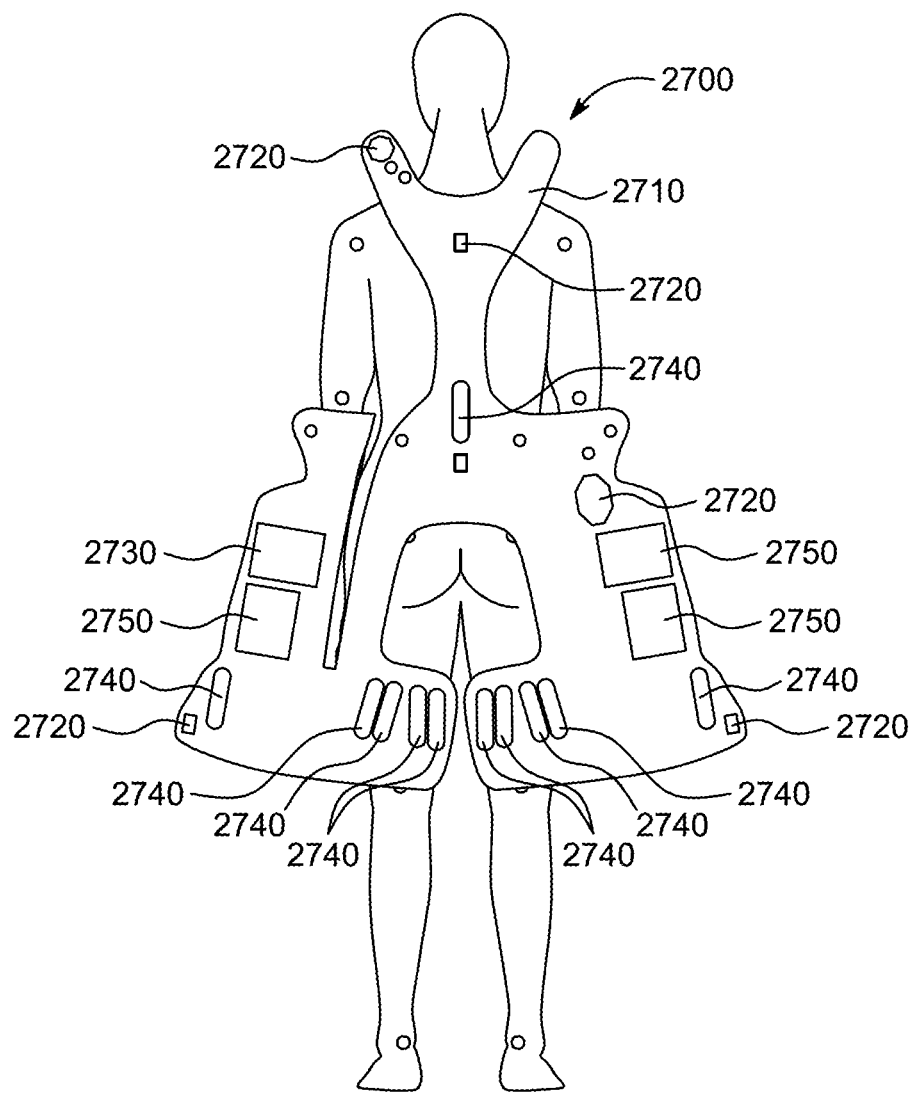
FIG. 27 shows an illustrative multiple assistive movement patch assembly according to an embodiment.

FIG. 27 shows an illustrative multiple assistive movement patch assembly (MAMPA) 2700 according to an embodiment. MAMPA 2700 may represent a single unitary patch that encompasses features of many patch assemblies such as patch assemblies 2551-2554 and is constructed to be detachably coupled to anterior and posterior sides of an exosuit. MAMPA 2700 is designed to be draped around the exosuit by the user and further secured to the exosuit by the user. For example, as shown in FIG. 27, MAMPA 2700 can be draped over the shoulders and around the hips and legs, and various portions of MAMPA 2700 can then be secured to load distribution members (not shown).

MAMPA 2700 can include a flexible substrate 2710 that serves as the foundation for holding various components thereon and for being detachably coupled to a plurality of load bearing members existing on anterior and posterior sides of the exosuit. MAMPA 2700 can include sensors 2720, batteries 2730, FLAs 2740, control electronics 2750, and other circuitry. MAMPA can also include a power and communications network that is coupled to sensors 2720, batteries 2730, FLAs 2740, and control electronics 2750. The control electronics are operative to selectively activate the plurality of FLAs to provide muscle movement assistance to a user of the exosuit. For example, a first set of the FLAs may provide hip flexor assistive movements and a second set of the FLAs may provide hip extensor assistive movements, wherein the first and second sets of FLAs are mutually exclusive. In addition, a third set of FLAs may provide spinal extensor assistive movements.

Figure 28:
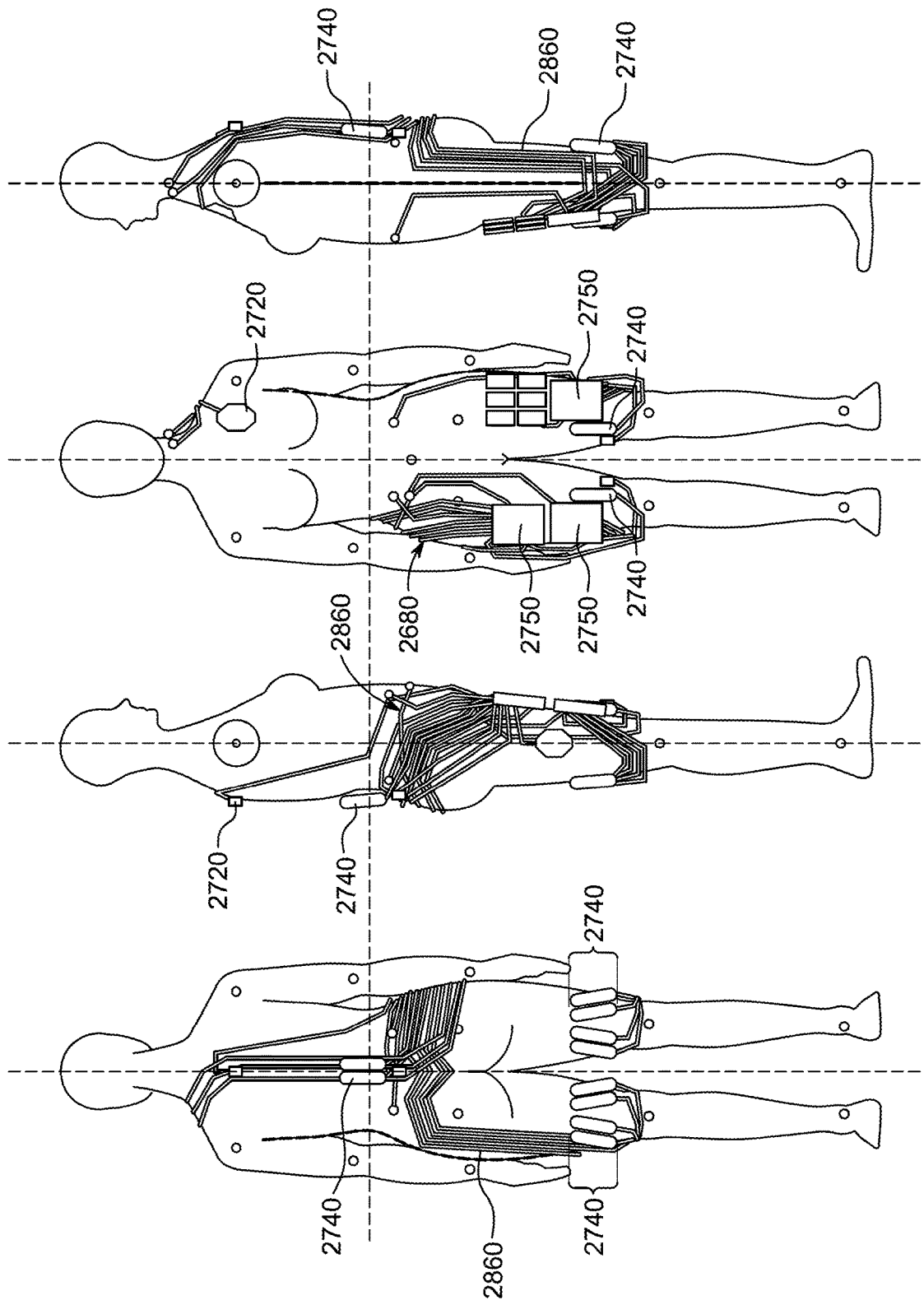
FIG. 28 shows illustrative back, side, and front views of the patch assembly of FIG. 27 when it is secured to an exosuit.

FIG. 28 shows illustrative back, side, and front views of MAMPA 2700 when it is secured to an exosuit. The flexible substrate 2710 has been omitted to promote clarity of various components, including the cable layout of the power and communications network 2860. As shown, power and communications network 2860 interconnects sensors 2720, batteries 2730, FLAs 2740, control electronics 2750, and other circuitry.

Figure 29:
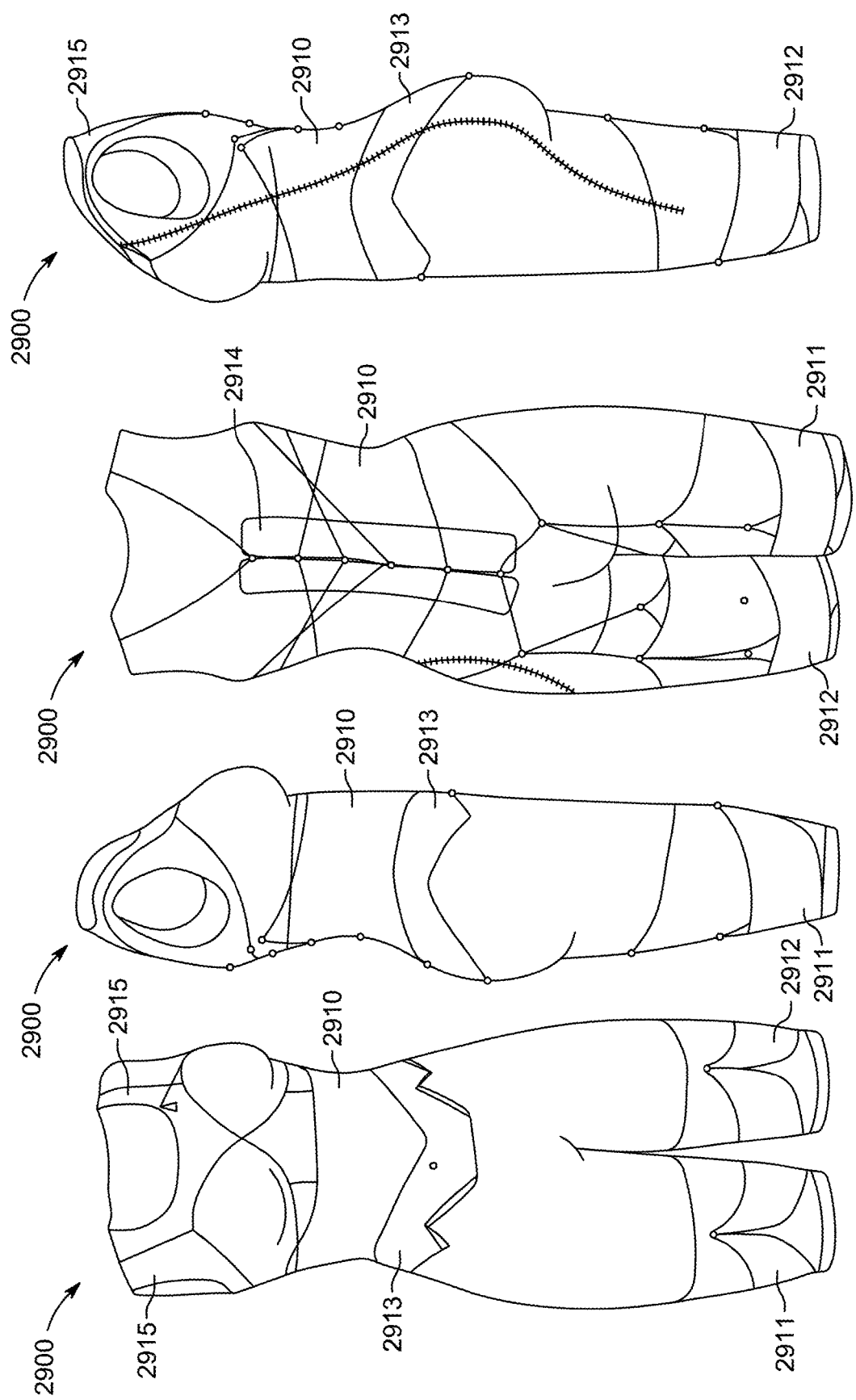
FIG. 29 shows illustrative back, side, and front views of a base layer of an exosuit according to various embodiments.

FIG. 29 shows illustrative back, side, and front views of a base layer 2910 of exosuit 2900 according to various embodiments. Base layer 2910 can include load distribution members 2911-2915. Load distribution members 2911 and 2912 are thigh based, load distribution member 2913 is waist/hip based, load distribution member 2914 is spinal column based, and load distribution members 2915 are shoulder based.

Figure 30:
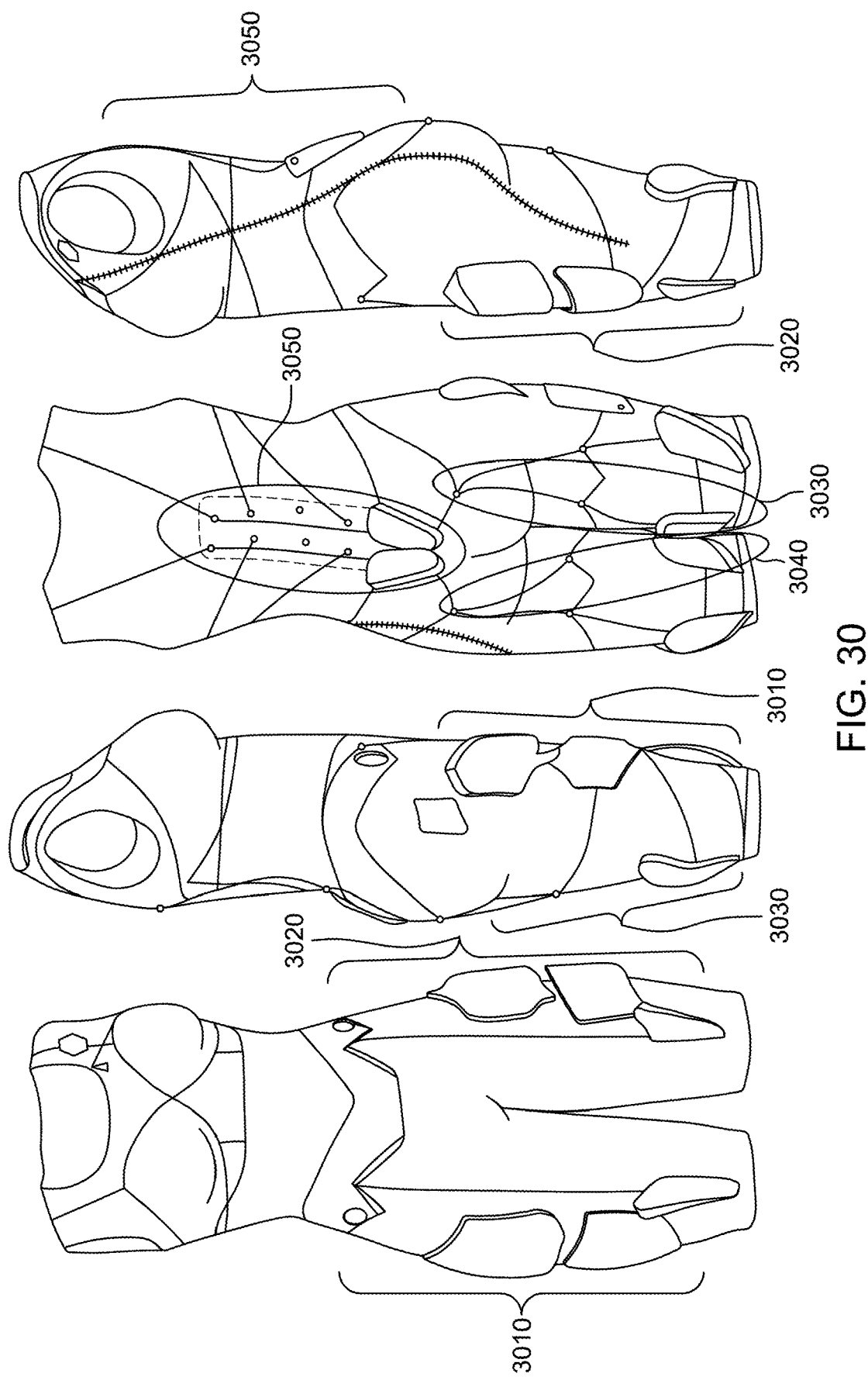
FIG. 30 shows illustrative back, side, and front views of an exosuit with patch assemblies attached thereto according to various embodiments.

FIG. 30 shows illustrative back, side, and front views of exosuit 2900 with patch assemblies attached thereto according to various embodiments. Patch assemblies 3010-306 may each be self-contained units such as patch assembly 2600 of FIG. 26 that can be detachable coupled to the appropriate load distribution members. Patch assembly 3010 can be attached to LDMs 2911 and 2913. Patch assembly 3020 can be attached to LDMs 2912 and 2913. Patch assembly 3030 can be attached to LDMs 2911 and 2913. Patch assembly 3040 can be attached to LDMs 2912 and 2913. Patch assembly 3050 can be attached to LDMs 2914 and 2915.

Figure 31:
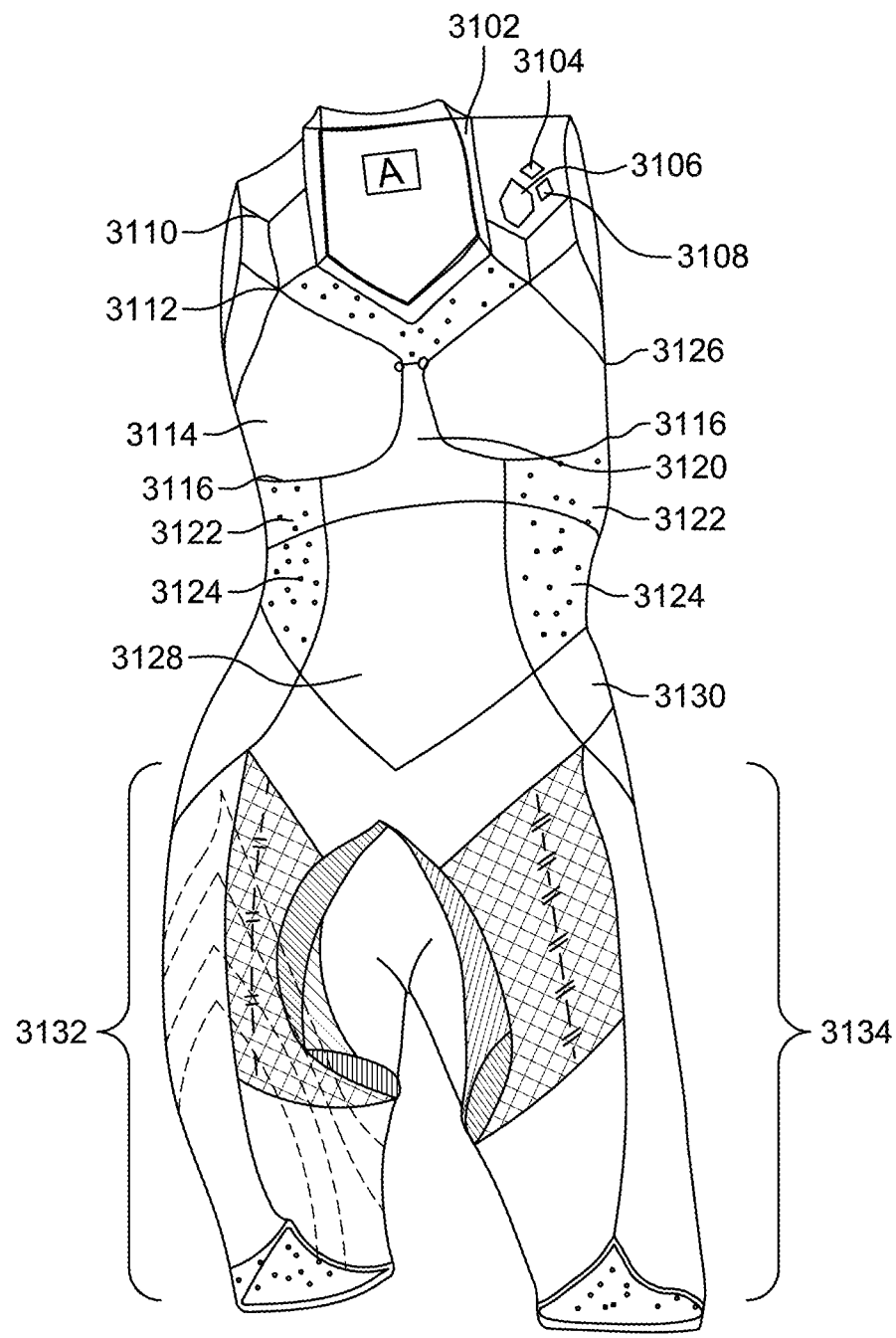
FIG. 31 shows illustrative front view of a female exosuit base layer according to an embodiment.
Figure 32:
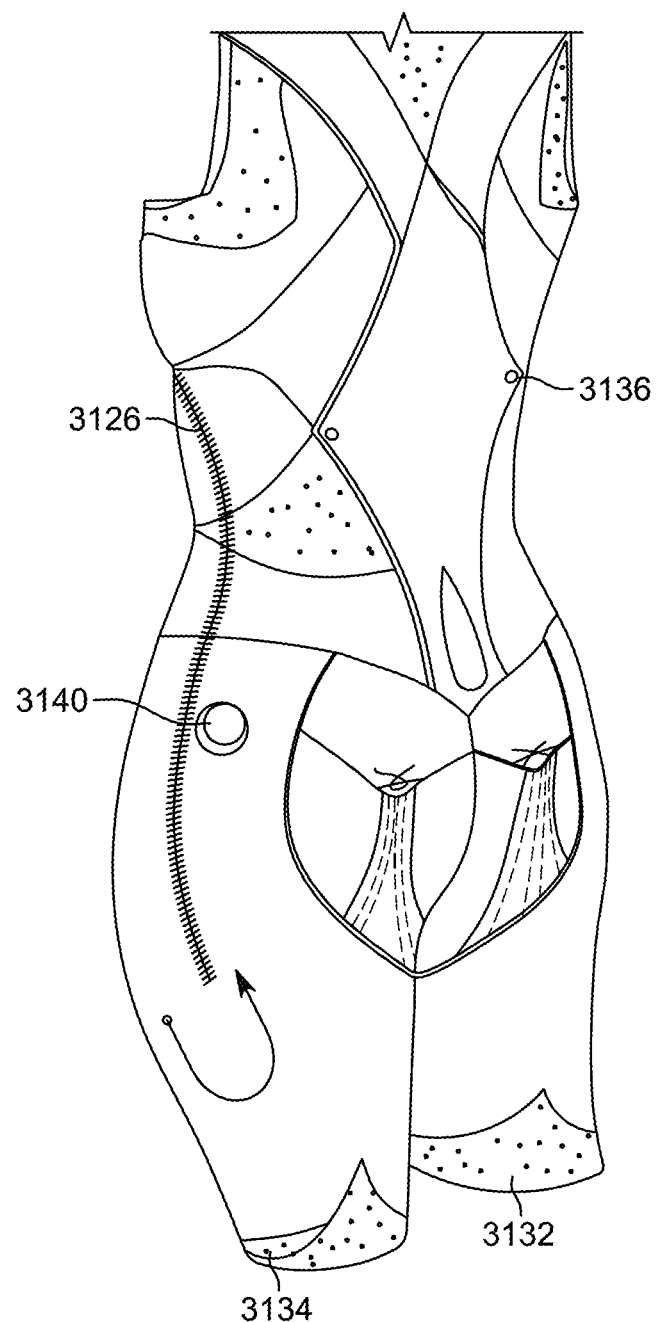
FIG. 32 show illustrative back view of a female exosuit base layer according to an embodiment.

FIGS. 31 and 32 show illustrative front and back views of female exosuit base layer 3100 according to an embodiment. A power layer and/or patch assemblies are not shown. Base layer 3100 may include many different features that each serve a different purpose and/or improve the comfort of the base layer fit. Base layer 3100 may include identification collar region 3102, LEDs 3104, touch sensor 3106, and microphone 3108. Base layer 3100 may include adjustable shoulder straps 3110 that permit shoulder strap sizing adjustment and registration and anchoring straps 3112 that secure the shoulder straps 3110 in place. Base layer 3100 can include soft molded portions 3116 for the breasts and underwire 3118 to provide support for portions 3116. Base layer 3100 can include stretch limit panel 3120 that limits stretch in all directions, support band 3122 that stretches to adapt to movement of the body, mesh zones 3124 that stretch and quickly dissipate heat, and relatively high stretch zone 3128. Base layer 3100 can include zipper 3126 for enabling easing donning and doffing. Base layer 3100 can include waist/hip load distribution member 3130, thigh load distribution members 3132 and 3134, back load distribution member 3136. Base layer 3100 may include magnetic guidance attachment points 3140 for facilitating connection of one or more patch assemblies.

Figure 33:
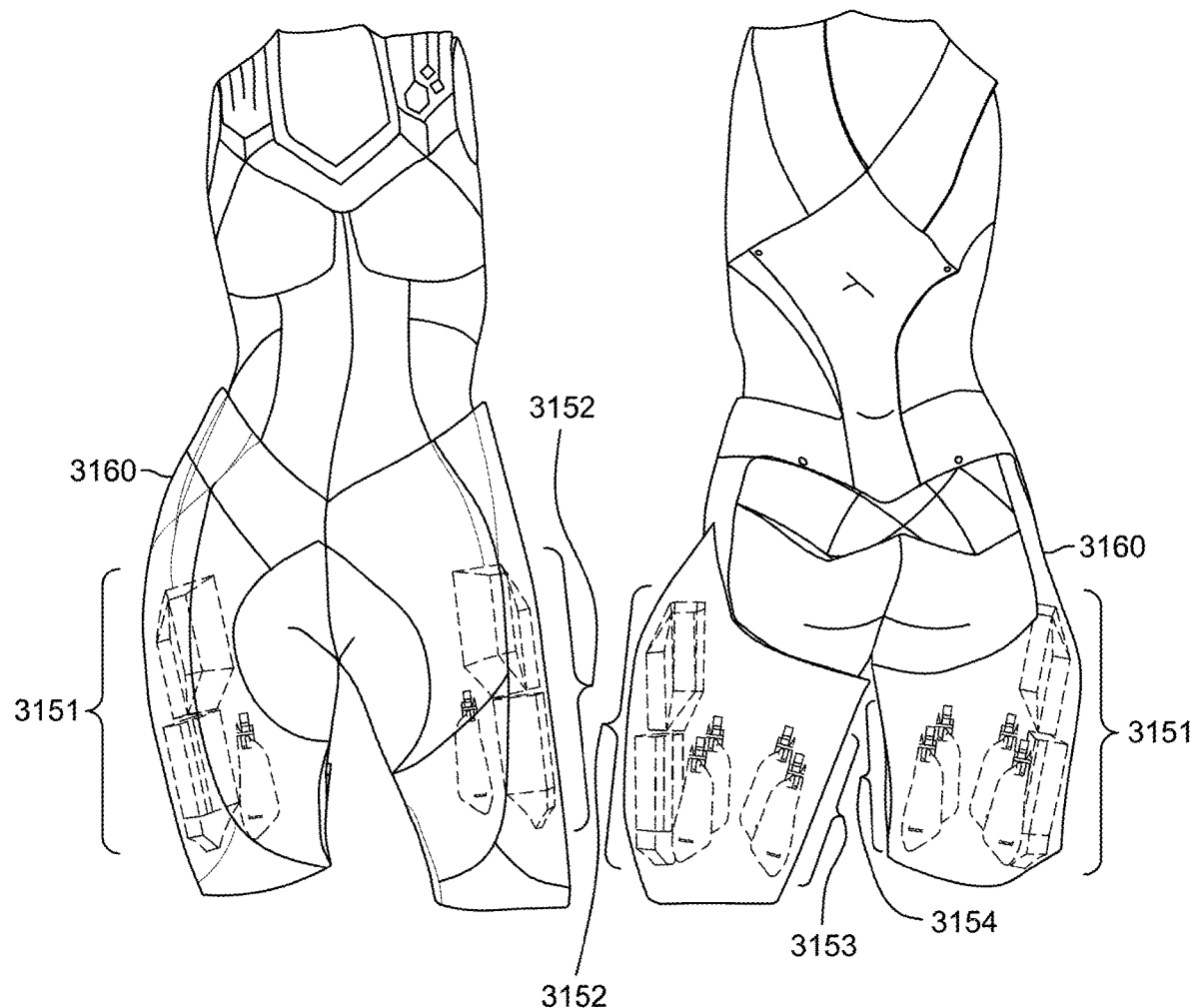
FIG. 33 shows show illustrative front and back views of a female exosuit base layer with patch assemblies and cover layer according to an embodiment.

FIG. 33 shows show illustrative front and back views of female exosuit base layer 3100 with patch assemblies and cover layer according to an embodiment. Patch assemblies 3151-3154 are coupled to base layer 3100 and cover layer 3160 is draped over patch assemblies 3151-3154 and a portion of base layer 3100.

Methods for Controlling and Applications of an Exosuit

An exosuit can be operated by electronic controllers disposed on or within the exosuit or in wireless or wired communication with the exosuit. The electronic controllers can be configured in a variety of ways to operate the exosuit and to enable functions of the exosuit. The electronic controllers can access and execute computer-readable programs that are stored in elements of the exosuit or in other systems that are in direct or indirect communications with the exosuit. The computer-readable programs can describe methods for operating the exosuit or can describe other operations relating to a exosuit or to a wearer of a exosuit.

Figure 23:
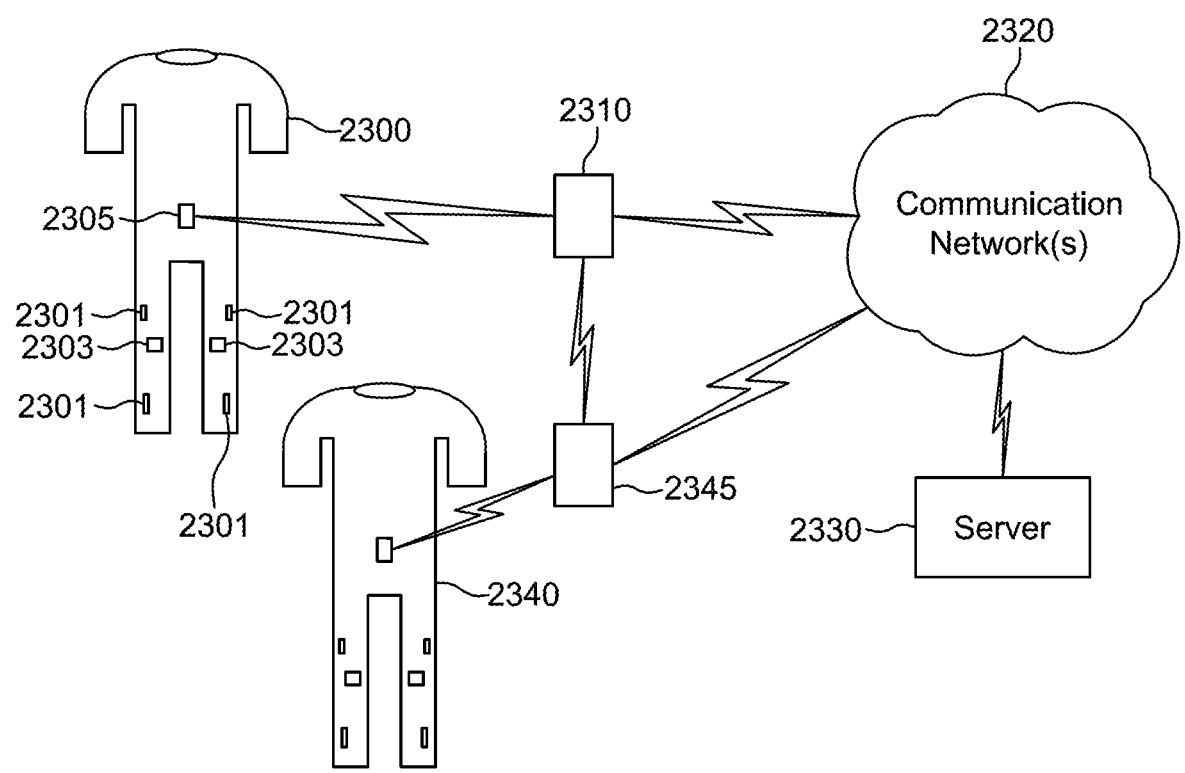
FIG. 23 illustrates an exosuit and system configured to communicate with the PPSO according to various embodiments.

FIG. 23 illustrates an example exosuit 2300 that includes actuators 2301, sensors 2303, and a controller configured to operate elements of the exosuit 2300 (e.g., 2301, 2303) to enable functions of exosuit 2300. The controller 2305 is configured to communicate wirelessly with a user interface 2310. The user interface 2310 is configured to present information to a user (e.g., a wearer of the exosuit 2300) and to the controller 2305 of the flexible exosuit or to other systems. The user interface 2310 can be involved in controlling and/or accessing information from elements of the exosuit 2300. For example, an application being executed by the user interface 2310 can access data from the sensors 2303, calculate an operation (e.g., to apply dorsiflexion stretch) of the actuators 2301, and transmit the calculated operation to the exosuit 2300. The user interface 2310 can additionally be configured to enable other functions; for example, the user interface 2310 can be configured to be used as a cellular telephone, a portable computer, an entertainment device, or to operate according to other applications.

The user interface 2310 can be configured to be removably mounted to the exosuit 2300 (e.g., by straps, magnets, Velcro, charging and/or data cables). Alternatively, the user interface 2310 can be configured as a part of the exosuit 2300 and not to be removed during normal operation. In some examples, a user interface can be incorporated as part of the exosuit 2300 (e.g., a touchscreen integrated into a sleeve of the exosuit 2300) and can be used to control and/or access information about the exosuit 2300 in addition to using the user interface 2310 to control and/or access information about the exosuit 2300. In some examples, the controller 2305 or other elements of the exosuit 2300 are configured to enable wireless or wired communication according to a standard protocol (e.g., Bluetooth, ZigBee, WiFi, LTE or other cellular standards, IRdA, Ethernet) such that a variety of systems and devices can be made to operate as the user interface 2310 when configured with complementary communications elements and computer-readable programs to enable such functionality.

The exosuit 2300 can be configured as described in example embodiments herein or in other ways according to an application. The exosuit 2300 can be operated to enable a variety of applications. The exosuit 2300 can be operated to enhance the strength of a wearer by detecting motions of the wearer (e.g., using sensors 2303) and responsively applying torques and/or forces to the body of the wearer (e.g., using actuators 2301) to increase the forces the wearer is able to apply to his/her body and/or environment. The exosuit 2300 can be operated to train a wearer to perform certain physical activities. For example, the exosuit 2300 can be operated to enable rehabilitative therapy of a wearer. The exosuit 2300 can operate to amplify motions and/or forces produced by a wearer undergoing therapy in order to enable the wearer to successfully complete a program of rehabilitative therapy. Additionally or alternatively, the exosuit 2300 can be operated to prohibit disordered movements of the wearer and/or to use the actuators 2301 and/or other elements (e.g., haptic feedback elements) to indicate to the wearer a motion or action to perform and/or motions or actions that should not be performed or that should be terminated. Similarly, other programs of physical training (e.g., dancing, skating, other athletic activities, vocational training) can be enabled by operation of the exosuit 2300 to detect motions, torques, or forces generated by a wearer and/or to apply forces, torques, or other haptic feedback to the wearer. Other applications of the exosuit 2300 and/or user interface 2310 are anticipated.

The user interface 2310 can additionally communicate with communications network(s) 2320. For example, the user interface 2310 can include a WiFi radio, an LTE transceiver or other cellular communications equipment, a wired modem, or some other elements to enable the user interface 2310 and exosuit 2300 to communicate with the Internet. The user interface 2310 can communicate through the communications network 2320 with a server 2330. Communication with the server 2330 can enable functions of the user interface 2310 and exosuit 2300. In some examples, the user interface 2310 can upload telemetry data (e.g., location, configuration of elements 2301, 2303 of the exosuit 2300, physiological data about a wearer of the exosuit 2300) to the server 2330.

In some examples, the server 2330 can be configured to control and/or access information from elements of the exosuit 2300 (e.g., 2301, 2303) to enable some application of the exosuit 2300. For example, the server 2330 can operate elements of the exosuit 2300 to move a wearer out of a dangerous situation if the wearer was injured, unconscious, or otherwise unable to move themselves and/or operate the exosuit 2300 and user interface 2310 to move themselves out of the dangerous situation. Other applications of a server in communications with a exosuit are anticipated.

The user interface 2310 can be configured to communicate with a second user interface 2345 in communication with and configured to operate a second flexible exosuit 2340. Such communication can be direct (e.g., using radio transceivers or other elements to transmit and receive information over a direct wireless or wired link between the user interface 2310 and the second user interface 2345). Additionally or alternatively, communication between the user interface 2310 and the second user interface 2345 can be facilitated by communications network(s) 2320 and/or a server 2330 configured to communicate with the user interface 2310 and the second user interface 2345 through the communications network(s) 2320.

Communication between the user interface 2310 and the second user interface 2345 can enable applications of the exosuit 2300 and second exosuit 2340. In some examples, actions of the exosuit 2300 and second flexible exosuit 2340 and/or of wearers of the exosuit 2300 and second exosuit 2340 can be coordinated. For example, the exosuit 2300 and second exosuit 2340 can be operated to coordinate the lifting of a heavy object by the wearers. The timing of the lift, and the degree of support provided by each of the wearers and/or the exosuit 2300 and second exosuit 2340 can be controlled to increase the stability with which the heavy object was carried, to reduce the risk of injury of the wearers, or according to some other consideration. Coordination of actions of the exosuit 2300 and second exosuit 2340 and/or of wearers thereof can include applying coordinated (in time, amplitude, or other properties) forces and/or torques to the wearers and/or elements of the environment of the wearers and/or applying haptic feedback (though actuators of the exosuits 2300, 2340, through dedicated haptic feedback elements, or through other methods) to the wearers to guide the wearers toward acting in a coordinated manner.

Coordinated operation of the exosuit 2300 and second exosuit 2340 can be implemented in a variety of ways. In some examples, one exosuit (and the wearer thereof) can act as a master, providing commands or other information to the other exosuit such that operations of the exosuits 2300 and 2340 are coordinated. For example, the exosuit 2300, 2340 can be operated to enable the wearers to dance (or to engage in some other athletic activity) in a coordinated manner. One of the exosuits can act as the 'lead', transmitting timing or other information about the actions performed by the 'lead' wearer to the other exosuit, enabling coordinated dancing motions to be executed by the other wearer. In some examples, a first wearer of a first exosuit can act as a trainer, modeling motions or other physical activities that a second wearer of a second exosuit can learn to perform. The first exosuit can detect motions, torques, forces, or other physical activities executed by the first wearer and can send information related to the detected activities to the second exosuit. The second exosuit can then apply forces, torques, haptic feedback, or other information to the body of the second wearer to enable the second wearer to learn the motions or other physical activities modeled by the first wearer. In some examples, the server 2330 can send commands or other information to the exosuits 2300 and 2340 to enable coordinated operation of the exosuits 2300 and 2340.

The exosuit 2300 can be operated to transmit and/or record information about the actions of a wearer, the environment of the wearer, or other information about a wearer of the exosuit 2300. In some examples, kinematics related to motions and actions of the wearer can be recorded and/or sent to the server 2330. These data can be collected for medical, scientific, entertainment, social media, or other applications. The data can be used to operate a system. For example, the exosuit 2300 can be configured to transmit motions, forces, and/or torques generated by a user to a robotic system (e.g., a robotic arm, leg, torso, humanoid body, or some other robotic system) and the robotic system can be configured to mimic the activity of the wearer and/or to map the activity of the wearer into motions, forces, or torques of elements of the robotic system. In another example, the data can be used to operate a virtual avatar of the wearer, such that the motions of the avatar mirrored or were somehow related to the motions of the wearer. The virtual avatar can be instantiated in a virtual environment, presented to an individual or system with which the wearer is communicating, or configured and operated according to some other application.

Conversely, the exosuit 2300 can be operated to present haptic or other data to the wearer. In some examples, the actuators 2301 (e.g., twisted string actuators, exotendons) and/or haptic feedback elements (e.g., EPAM haptic elements) can be operated to apply and/or modulate forces applied to the body of the wearer to indicate mechanical or other information to the wearer. For example, the activation in a certain pattern of a haptic element of the exosuit 2300 disposed in a certain location of the exosuit 2300 can indicate that the wearer had received a call, email, or other communications. In another example, a robotic system can be operated using motions, forces, and/or torques generated by the wearer and transmitted to the robotic system by the exosuit 2300. Forces, moments, and other aspects of the environment and operation of the robotic system can be transmitted to the exosuit 2300 and presented (using actuators 2301 or other haptic feedback elements) to the wearer to enable the wearer to experience force-feedback or other haptic sensations related to the wearer's operation of the robotic system. In another example, haptic data presented to a wearer can be generated by a virtual environment, e.g., an environment containing an avatar of the wearer that is being operated based on motions or other data related to the wearer that is being detected by the exosuit 2300.

Note that the exosuit 2300 illustrated in FIG. 23 is only one example of a exosuit that can be operated by control electronics, software, or algorithms described herein. Control electronics, software, or algorithms as described herein can be configured to control flexible exosuits or other mechatronic and/or robotic system having more, fewer, or different actuators, sensors or other elements. Further, control electronics, software, or algorithms as described herein can be configured to control exosuits configured similarly to or differently from the illustrated exosuit 2300. Further, control electronics, software, or algorithms as described herein can be configured to control flexible exosuits having reconfigurable hardware (i.e., exosuits that are able to have actuators, sensors, or other elements added or removed) and/or to detect a current hardware configuration of the flexible exosuits using a variety of methods.

Software Hierarchy for Control of an Exosuit

A controller of a exosuit and/or computer-readable programs executed by the controller can be configured to provide encapsulation of functions and/or components of the flexible exosuit. That is, some elements of the controller (e.g., subroutines, drivers, services, daemons, functions) can be configured to operate specific elements of the exosuit (e.g., a twisted string actuator, a haptic feedback element) and to allow other elements of the controller (e.g., other programs) to operate the specific elements and/or to provide abstracted access to the specific elements (e.g., to translate a command to orient an actuator in a commanded direction into a set of commands sufficient to orient the actuator in the commanded direction). This encapsulation can allow a variety of services, drivers, daemons, or other computer-readable programs to be developed for a variety of applications of a flexible exosuits. Further, by providing encapsulation of functions of a flexible exosuit in a generic, accessible manner (e.g., by specifying and implementing an application programming interface (API) or other interface standard), computer-readable programs can be created to interface with the generic, encapsulated functions such that the computer-readable programs can enable operating modes or functions for a variety of differently-configured exosuit, rather than for a single type or model of flexible exosuit. For example, a virtual avatar communications program can access information about the posture of a wearer of a flexible exosuit by accessing a standard exosuit API. Differently-configured exosuits can include different sensors, actuators, and other elements, but can provide posture information in the same format according to the API. Other functions and features of a flexible exosuit, or other robotic, exoskeletal, assistive, haptic, or other mechatronic system, can be encapsulated by APIs or according to some other standardized computer access and control interface scheme.

Figure 24:
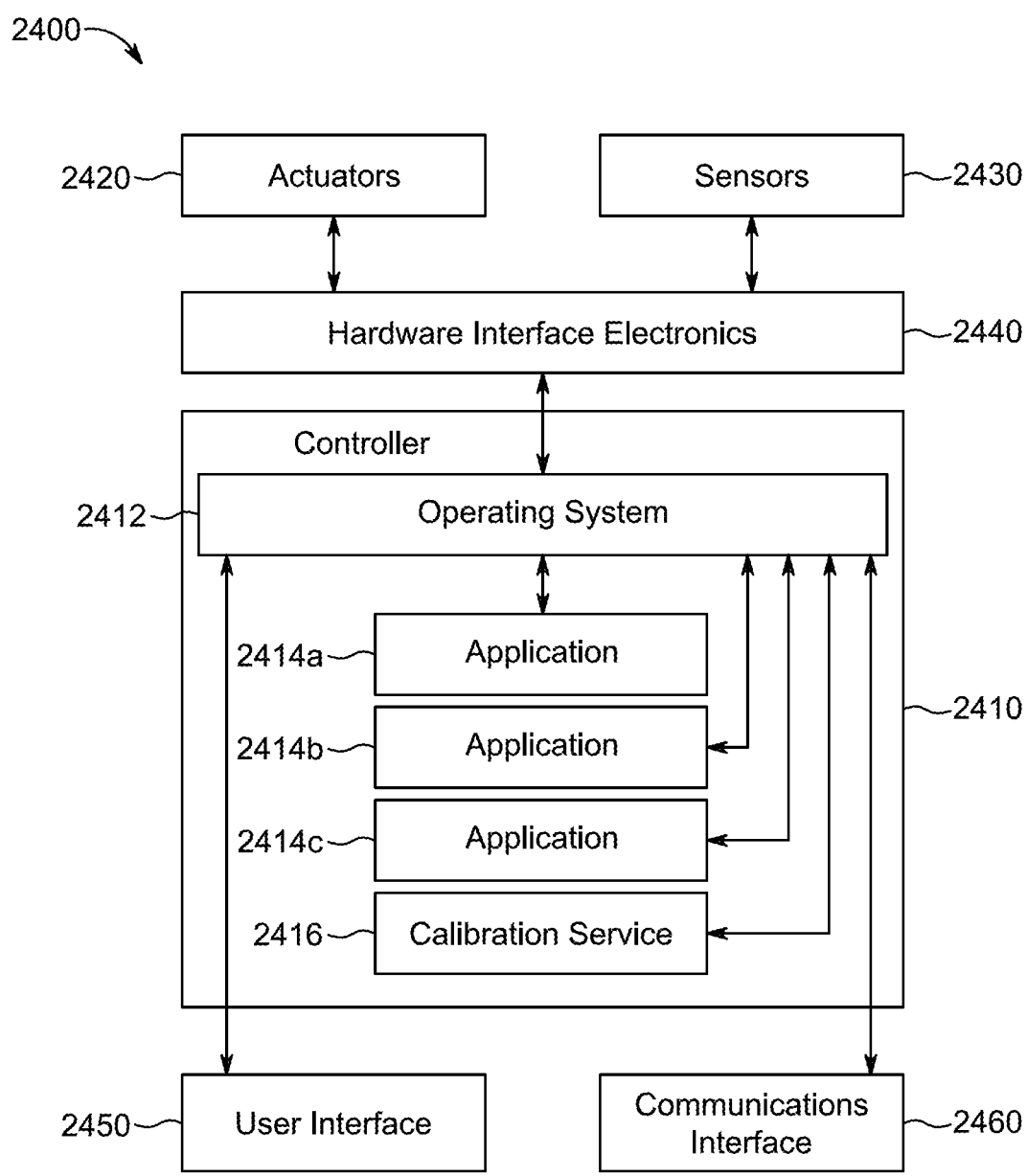
FIG. 24 illustrates a schematic of a control scheme for an exosuit according to various embodiments.

FIG. 24 is a schematic illustrating elements of a exosuit 2400 and a hierarchy of control or operating the exosuit 2400. The flexible exosuit includes actuators 2420 and sensors 2430 configured to apply forces and/or torques to and detect one or more properties of, respectively, the exosuit 2400, a wearer of the exosuit 2400, and/or the environment of the wearer. The exosuit 2400 additionally includes a controller 2410 configured to operate the actuators 2420 and sensors 2430 by using hardware interface electronics 2440. The hardware electronics interface 2440 includes electronics configured to interface signals from and to the controller 1510 with signals used to operate the actuators 1520 and sensors 1530. For example, the actuators 1520 can include exotendons, and the hardware interface electronics 2440 can include high-voltage generators, high-voltage switches, and high-voltage capacitance meters to clutch and un-clutch the exotendons and to report the length of the exotendons. The hardware interface electronics 2440 can include voltage regulators, high voltage generators, amplifiers, current detectors, encoders, magnetometers, switches, controlled-current sources, DACs, ADCs, feedback controllers, brushless motor controllers, or other electronic and mechatronic elements.

The controller 2410 additionally operates a user interface 2450 that is configured to present information to a user and/or wearer of the exosuit 2400 and a communications interface 2460 that is configured to facilitate the transfer of information between the controller 2410 and some other system (e.g., by transmitting a wireless signal). Additionally or alternatively, the user interface 2450 can be part of a separate system that is configured to transmit and receive user interface information to/from the controller 2410 using the communications interface 2460 (e.g., the user interface 2450 can be part of a cellphone).

The controller 2410 is configured to execute computer-readable programs describing functions of the flexible exosuit 2412. Among the computer-readable programs executed by the controller 2410 are an operating system 2412, applications 2414a, 2414b, 2414c, and a calibration service 2416. The operating system 2412 manages hardware resources of the controller 2410 (e.g., I/O ports, registers, timers, interrupts, peripherals, memory management units, serial and/or parallel communications units) and, by extension, manages the hardware resources of the exosuit 2400. The operating system 2412 is the only computer-readable program executed by the controller 2410 that has direct access to the hardware interface electronics 2440 and, by extension, the actuators 2420 and sensors 2430 of the exosuit 2400.

The applications 2414a, 2414b, 2414 are computer-readable programs that describe some function, functions, operating mode, or operating modes of the exosuit 2400. For example, application 2414a can describe a process for transmitting information about the wearer's posture to update a virtual avatar of the wearer that includes accessing information on a wearer's posture from the operating system 2412, maintaining communications with a remote system using the communications interface 2460, formatting the posture information, and sending the posture information to the remote system. The calibration service 2416 is a computer-readable program describing processes to store parameters describing properties of wearers, actuators 2420, and/or sensors 2430 of the exosuit 2400, to update those parameters based on operation of the actuators 2420, and/or sensors 2430 when a wearer is using the exosuit 2400, to make the parameters available to the operating system 2412 and/or applications 2414a, 2414b, 2414c, and other functions relating to the parameters. Note that applications 2414a, 2414b, 2414 and calibration service 2416 are intended as examples of computer-readable programs that can be run by the operating system 2412 of the controller 2410 to enable functions or operating modes of a exosuit 2400.

The operating system 2412 can provide for low-level control and maintenance of the hardware (e.g., 2420, 2430, 2440). In some examples, the operating system 2412 and/or hardware interface electronics 2440 can detect information about the exosuit 2400, the wearer, and/or the wearer's environment from one or more sensors 2430 at a constant specified rate. The operating system 2412 can generate an estimate of one or more states or properties of the exosuit 2400 or components thereof using the detected information. The operating system 2412 can update the generated estimate at the same rate as the constant specified rate or at a lower rate. The generated estimate can be generated from the detected information using a filter to remove noise, generate an estimate of an indirectly-detected property, or according to some other application. For example, the operating system 2412 can generate the estimate from the detected information using a Kalman filter to remove noise and to generate an estimate of a single directly or indirectly measured property of the exosuit 2400, the wearer, and/or the wearer's environment using more than one sensor. In some examples, the operating system can determine information about the wearer and/or exosuit 2400 based on detected information from multiple points in time. For example, the operating system 2400 can determine an eversion stretch and dorsiflexion stretch.

In some examples, the operating system 2412 and/or hardware interface electronics 2440 can operate and/or provide services related to operation of the actuators 2420. That is, in case where operation of the actuators 2420 requires the generation of control signals over a period of time, knowledge about a state or states of the actuators 2420, or other considerations, the operating system 2412 and/or hardware interface electronics 2440 can translate simple commands to operate the actuators 2420 (e.g., a command to generate a specified level of force using a twisted string actuator (TSA) of the actuators 2420) into the complex and/or state-based commands to the hardware interface electronics 2440 and/or actuators 2420 necessary to effect the simple command (e.g., a sequence of currents applied to windings of a motor of a TSA, based on a starting position of a rotor determined and stored by the operating system 2410, a relative position of the motor detected using an encoder, and a force generated by the TSA detected using a load cell).

In some examples, the operating system 2412 can further encapsulate the operation of the exosuit 2400 by translating a system-level simple command (e.g., a commanded level of force tension applied to the footplate) into commands for multiple actuators, according to the configuration of the exosuit 2400. This encapsulation can enable the creation of general-purpose applications that can effect a function of an exosuit (e.g., allowing a wearer of the exosuit to stretch his foot) without being configured to operate a specific model or type of exosuit (e.g., by being configured to generate a simple force production profile that the operating system 2412 and hardware interface electronics 2440 can translate into actuator commands sufficient to cause the actuators 2420 to apply the commanded force production profile to the footplate).

The operating system 2412 can act as a standard, multipurpose platform to enable the use of a variety of exosuits having a variety of different hardware configurations to enable a variety of mechatronic, biomedical, human interface, training, rehabilitative, communications, and other applications. The operating system 2412 can make sensors 2430, actuators 2420, or other elements or functions of the exosuit 2400 available to remote systems in communication with the exosuit 2400 (e.g., using the communications interface 2460) and/or a variety of applications, daemons, services, or other computer-readable programs being executed by operating system 2412. The operating system 2412 can make the actuators, sensors, or other elements or functions available in a standard way (e.g., through an API, communications protocol, or other programmatic interface) such that applications, daemons, services, or other computer-readable programs can be created to be installed on, executed by, and operated to enable functions or operating modes of a variety of flexible exosuits having a variety of different configurations. The API, communications protocol, or other programmatic interface made available by the operating system 2412 can encapsulate, translate, or otherwise abstract the operation of the exosuit 2400 to enable the creation of such computer-readable programs that are able to operate to enable functions of a wide variety of differently-configured flexible exosuits.

Additionally or alternatively, the operating system 2412 can be configured to operate a modular flexible exosuit system (i.e., a flexible exosuit system wherein actuators, sensors, or other elements can be added or subtracted from a flexible exosuit to enable operating modes or functions of the flexible exosuit). In some examples, the operating system 2412 can determine the hardware configuration of the exosuit 2400 dynamically and can adjust the operation of the exosuit 2400 relative to the determined current hardware configuration of the exosuit 2400. This operation can be performed in a way that was 'invisible' to computer-readable programs (e.g., 2414a, 2414b, 2414c) accessing the functionality of the exosuit 2400 through a standardized programmatic interface presented by the operating system 2412. For example, the computer-readable program can indicate to the operating system 2412, through the standardized programmatic interface, that a specified level of torque was to be applied to an ankle of a wearer of the exosuit 2400. The operating system 2412 can responsively determine a pattern of operation of the actuators 2420, based on the determined hardware configuration of the exosuit 2400, sufficient to apply the specified level of torque to the ankle of the wearer.

In some examples, the operating system 2412 and/or hardware interface electronics 2440 can operate the actuators 2420 to ensure that the exosuit 2400 does not operate to directly cause the wearer to be injured and/or elements of the exosuit 2400 to be damaged. In some examples, this can include not operating the actuators 2420 to apply forces and/or torques to the body of the wearer that exceeded some maximum threshold. This can be implemented as a watchdog process or some other computer-readable program that can be configured (when executed by the controller 2410) to monitor the forces being applied by the actuators 2420 (e.g., by monitoring commands sent to the actuators 2420 and/or monitoring measurements of forces or other properties detected using the sensors 2430) and to disable and/or change the operation of the actuators 2420 to prevent injury of the wearer. Additionally or alternatively, the hardware interface electronics 2440 can be configured to include circuitry to prevent excessive forces and/or torques from being applied to the wearer (e.g., by channeling to a comparator the output of a load cell that is configured to measure the force generated by a TSA, and configuring the comparator to cut the power to the motor of the TSA when the force exceeded a specified level).

In some examples, operating the actuators 2420 to ensure that the exosuit 2400 does not damage itself can include a watchdog process or circuitry configured to prevent overcurrent, over-load, over-rotation, or other conditions from occurring that can result in damage to elements of the exosuit 2400. For example, the hardware interface electronics 2440 can include a metal oxide varistor, breaker, shunt diode, or other element configured to limit the voltage and/or current applied to a winding of a motor.

Note that the above functions described as being enabled by the operating system 2412 can additionally or alternatively be implemented by applications 2414*a*, 2414*b*, 2414*c*, services, drivers, daemons, or other computer-readable programs executed by the controller 2400. The applications, drivers, services, daemons, or other computer-readable programs can have special security privileges or other properties to facilitate their use to enable the above functions.

The operating system 2412 can encapsulate the functions of the hardware interface electronics 2440, actuators 2420, and sensors 2430 for use by other computer-readable programs (e.g., applications 2414*a*, 2414*b*, 2414*c*, calibration service 2416), by the user (through the user interface 2450), and/or by some other system (i.e., a system configured to communicate with the controller 2410 through the communications interface 2460). The encapsulation of functions of the exosuit 2400 can take the form of application programming interfaces (APIs), i.e., sets of function calls and procedures that an application running on the controller 2410 can use to access the functionality of elements of the exosuit 2400. In some examples, the operating system 2412 can make available a standard 'exosuit API' to applications being executed by the controller 2410. The 'exosuit API' can enable applications 2414*a*, 2414*b*, 2414*c* to access functions of the exosuit 2400 without requiring those applications 2414*a*, 2414*b*, 2414*c* to be configured to generate whatever complex, time-dependent signals are necessary to operate elements of the exosuit 2400 (e.g., actuators 2420, sensors 2430).

The 'exosuit API' can allow applications 2414*a*, 2414*b*, 2414*c* to send simple commands to the operating system 2412 (e.g., 'begin storing mechanical energy from the ankle of the wearer when the foot of the wearer contacts the ground') in such that the operating system 2412 can interpret those commands and generate the command signals to the hardware interface electronics 2440 or other elements of the exosuit 2400 that are sufficient to effect the simple commands generated by the applications 2414*a*, 2414*b*, 2414*c* (e.g., determining whether the foot of the wearer has contacted the ground based on information detected by the sensors 2430, responsively applying high voltage to an exotendon that crosses the user's ankle).

The 'exosuit API' can be an industry standard (e.g., an ISO standard), a proprietary standard, an open-source standard, or otherwise made available to individuals that can then produce applications for exosuits. The 'exosuit API' can allow applications, drivers, services, daemons, or other computer-readable programs to be created that are able to operate a variety of different types and configurations of exosuits by being configured to interface with the standard 'exosuit API' that is implemented by the variety of different types and configurations of exosuits. Additionally or alternatively, the 'exosuit API' can provide a standard encapsulation of individual exosuit-specific actuators (i.e., actuators that apply forces to specific body segments, where differently-configured exosuits may not include an actuator that applies forces to the same specific body segments) and can provide a standard interface for accessing information on the configuration of whatever exosuit is providing the 'exosuit API'. An application or other program that accesses the 'exosuit API' can access data about the configuration of the exosuit (e.g., locations and forces between body segments generated by actuators, specifications of actuators, locations and specifications of sensors) and can generate simple commands for individual actuators (e.g., generate a force of 30 newtons for 50 milliseconds) based on a model of the exosuit generated by the application and based on the information on the accessed data about the configuration of the exosuit. Additional or alternate functionality can be encapsulated by an 'exosuit API' according to an application.

Applications 2414*a*, 2414*b*, 2414*c* can individually enable all or parts of the functions and operating modes of a flexible exosuit described herein. For example, an application can enable haptic control of a robotic system by transmitting postures, forces, torques, and other information about the activity of a wearer of the exosuit 2400 and by translating received forces and torques from the robotic system into haptic feedback applied to the wearer (i.e., forces and torques applied to the body of the wearer by actuators 2420 and/or haptic feedback elements). In another example, an application can enable a wearer to locomote more efficiently by submitting commands to and receiving data from the operating system 2412 (e.g., through an API) such that actuators 2420 of the exosuit 2400 assist the movement of the user, extract negative work from phases of the wearer's locomotion and inject the stored work to other phases of the wearer's locomotion, or other methods of operating the exosuit 2400. Applications can be installed on the controller 2410 and/or on a computer-readable storage medium included in the exosuit 2400 by a variety of methods. Applications can be installed from a removable computer-readable storage medium or from a system in communication with the controller 2410 through the communications interface 2460. In some examples, the applications can be installed from a web site, a repository of compiled or un-compiled programs on the Internet, an online store (e.g., Google Play, iTunes App Store), or some other source. Further, functions of the applications can be contingent upon the controller 2410 being in continuous or periodic communication with a remote system (e.g., to receive updates, authenticate the application, to provide information about current environmental conditions).

The exosuit 2400 illustrated in FIG. 24 is intended as an illustrative example. Other configurations of flexible exosuits and of operating systems, kernels, applications, drivers, services, daemons, or other computer-readable programs are anticipated. For example, an operating system configured to operate a exosuit can include a real-time operating system component configured to generate low-level commands to operate elements of the exosuit and a non-real-time component to enable less time-sensitive functions, like a clock on a user interface, updating computer-readable programs stored in the exosuit, or other functions. A exosuit can include more than one controller; further, some of those controllers can be configured to execute real-time applications, operating systems, drivers, or other computer-readable programs (e.g., those controllers were configured to have very short interrupt servicing routines, very fast thread switching, or other properties and functions relating to latency-sensitive computations) while other controllers are configured to enable less time-sensitive functions of a flexible exosuit. Additional configurations and operating modes of a exosuit are anticipated. Further, control systems configured as described herein can additionally or alternatively be configured to enable the operation of devices and systems other than exosuit; for example, control systems as described herein can be configured to operate robots, rigid exosuits or exoskeletons, assistive devices, prosthetics, or other mechatronic devices.

Controllers of Mechanical Operation of an Exosuit

Control of actuators of a exosuit can be implemented in a variety of ways according to a variety of control schemes. Generally, one or more hardware and/or software controllers can receive information about the state of the flexible exosuit, a wearer of the exosuit, and/or the environment of the exosuit from sensors disposed on or within the exosuit and/or a remote system in communication with the exosuit. The one or more hardware and/or software controllers can then generate a control output that can be executed by actuators of the exosuit to effect a commanded state of the exosuit and/or to enable some other application. One or more software controllers can be implemented as part of an operating system, kernel, driver, application, service, daemon, or other computer-readable program executed by a processor included in the exosuit.

Alternative Applications and Embodiments

The exosuit embodiments described above generally relate to an ankle-stretching exosuit, typically to improve ankle flexibility by performing stretches prescribed for patients with DMD. However, it can be easily appreciated that the application for exosuits is not limited to ankle stretches for DMD patients. In one alternative embodiment, a exosuit may be used during injury rehabilitation in place of a continuous passive motion (CPM) machine. The system described above may be used to restore ROM of the ankle, for example in the case of surgery or arthritis. An ankle ROM exosuit may additionally include FLAs approximating calf muscles to induce plantar-flexion of the ankle Whereas a CPM machine simply cycles through a pre-set ROM, a exosuit can adaptively accommodate changes in a joints ROM. ROM of the ankle may be sensed by the sensors and controls layer, for example via one or more goniometers or force sensors, such that the exosuit applies a regimen that gradually increases ROM over time.

Exosuits may be optimized to other joints and muscle groups as well. For example, a exosuit may be adapted to pronate or supinate the forearm and wrist, in order to increase rotational range of motion of the joints, or muscles in the case of contractors. A exosuit adapted to flex and extend the knee can be used as an alternative to a CPM machine, in order to increase the range of motion of the knee after surgery such as anterior cruciate ligament (ACL) reconstruction or total joint replacement.

In some embodiments, a powered assistive exosuit intended primarily for assistive functions can also be adapted to perform exosuit functions. Embodiments of such an assistive exosuit typically include FLAs approximating muscle groups such as hip flexors, gluteal/hip extensors, spinal extensors, or abdominal muscles. In the assistive modes of these exosuits, these FLAs provide assistance for activities such as moving between standing and seated positions, walking, and postural stability. Actuation of specific FLAs within such an exosuit system may also provide stretching assistance. Typically, activation of one or more FLAs approximating a muscle group can stretch the antagonist muscles. For example, activation of one or more FLAs approximating the abdominal muscles might stretch the spinal extensors, or activation of one or more FLAs approximating gluteal/hip extensor muscles can stretch the hip flexors. The exosuit may be adapted to detect when the wearer is ready to initiate a stretch and perform an automated stretching regimen; or the wearer may indicate to the suit to initiate a stretching regimen.

Applications

It can be appreciated that assistive exosuits may have multiple applications. Assistive exosuits may be prescribed for medical applications. These may include therapeutic applications, such as assistance with exercise or stretching regimens for rehabilitation, disease mitigation or other therapeutic purposes. Mobility-assistance devices such as wheelchairs, walkers, crutches and scooters are often prescribed for individuals with mobility impairments. Likewise, an assistive exosuit may be prescribed for mobility assistance for patients with mobility impairments. Compared with mobility assistance devices such as wheelchairs, walkers, crutches and scooters, an assistive exosuit may be less bulky, more visually appealing, and conform with activities of daily living such as riding in vehicles, attending community or social functions, using the toilet, and common household activities.

An assistive exosuit may additionally function as primary apparel, fashion items or accessories. The exosuit may be stylized for desired visual appearance. The stylized design may reinforce visual perception of the assistance that the exosuit is intended to provide. For example, an assistive exosuit intended to assist with torso and upper body activities may present a visual appearance of a muscular torso and upper body. Alternatively, the stylized design may be intended to mask or camouflage the functionality of the assistive exosuit through design of the base layer, electro/mechanical integration or other design factors.

Similarly to assistive exosuits intended for medically prescribed mobility assistance, assistive exosuits may be developed and utilized for non-medical mobility assistance, performance enhancement and support. For many, independent aging is associated with greater quality of life, however activities may become more limited with time due to normal aging processes. An assistive exosuit may enable aging individuals living independently to electively enhance their abilities and activities. For example, gait or walking assistance could enable individuals to maintain routines such as social walking or golf. Postural assistance may render social situations more comfortable, with less fatigue. Assistance with transitioning between seated and standing positions may reduce fatigue, increase confidence, and reduce the risk of falls. These types of assistance, while not explicitly medical in nature, may enable more fulfilling, independent living during aging processes.

Athletic applications for an assistive exosuit are also envisioned. In one example, an exosuit may be optimized to assist with a particular activity, such as cycling. In the cycling example, FLAs approximating gluteal or hip extensor muscles may be integrated into bicycle clothing, providing assistance with pedaling. The assistance could be varied based on terrain, fatigue level or strength of the wearer, or other factors. The assistance provided may enable increased performance, injury avoidance, or maintenance of performance in the case of injury or aging. It can be appreciated that assistive exosuits could be optimized to assist with the demands of other sports such as running, jumping, swimming, skiing, or other activities. An athletic assistive exosuit may also be optimized for training in a particular sport or activity. Assistive exosuits may guide the wearer in proper form or technique, such as a golf swing, running stride, skiing form, swimming stroke, or other components of sports or activities. Assistive exosuits may also provide resistance for strength or endurance training. The provided resistance may be according to a regimen, such as high intensity intervals.

Assistive exosuit systems as described above may also be used in gaming applications. Motions of the wearer, detected by the suit, may be incorporated as a game controller system. For example, the suit may sense wearer's motions that simulate running, jumping, throwing, dancing, fighting, or other motions appropriate to a particular game. The suit may provide haptic feedback to the wearer, including resistance or assistance with the motions performed or other haptic feedback to the wearer.

Assistive exosuits as described above may be used for military or first responder applications. Military and first responder personnel are often to be required to perform arduous work where safety or even life may be at stake. An assistive exosuit may provide additional strength or endurance as required for these occupations. An assistive exosuit may connect to one or more communication networks to provide communication services for the wearer, as well as remote monitoring of the suit or wearer.

Assistive exosuits as described above may be used for industrial or occupational safety applications. Exosuits may provide more strength or endurance for specific physical tasks such as lifting or carrying or repetitive tasks such as assembly line work. By providing physical assistance, assistive exosuits may also help avoid or prevent occupational injury due overexertion or repetitive stress.

Assistive exosuits as described above may also be configured as home accessories. Home accessory assistive exosuits may assist with household tasks such as cleaning or yard work, or may be used for recreational or exercise purposes. The communication capabilities of an assistive exosuit may connect to a home network for communication, entertainment or safety monitoring purposes.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art can appreciate that the conception, upon which this disclosure is based, may readily be utilized as a basis for the designing of other structures, systems, methods and media for carrying out the several purposes of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed is:

1. A patch assembly for use with an exosuit comprising:
    a flexible substrate detachably coupled to a patch integration region of the exosuit, wherein the patch integration region is standardized across a plurality of differently sized exosuits such that any combination of patch assemblies of different sizes is able to be secured to any one of the plurality of differently sized exosuits, wherein the flexible substrate is sized according to one of the patch assemblies of different sizes, the flexible substrate comprising mounting components to secure the flexible substrate to the patch integration region of the exosuit;
    at least one flexible linear actuator (FLA) coupled to the flexible substrate, wherein the at least one FLA comprises a motor and a twisted string, wherein a first end of the twisted string is coupled to a rotatable member associated with the motor and a second end of the twisted string extends distally away from the patch integration region and is attached to a portion of the exosuit other than the patch integration region of the exosuit;
    at least one battery coupled to the flexible substrate; and
    control electronics coupled to the flexible substrate, the at least one FLA, and the at least one battery and configured to selectively activate the at least one FLA to provide muscle movement assistance to a user of the exosuit, wherein the at least one FLA shortens a length of the twisted string to apply a force during the muscle movement assistance,
    wherein when the patch assembly is removed from or attached to the exosuit, the combination of the flexible substate, the at least one FLA, the at least one battery, and the control electronics is collectively removed from or attached to the exosuit as a modular patch.

2. The patch assembly of claim 1, the flexible substrate further comprising:
    a circuit board that is electrically coupled to the at least one FLA, the at least one battery, and the control electronics.

3. The patch assembly of claim 2, wherein the patch assembly is a self-contained system that supplies power to and drive control over the at least one FLA.

4. The patch assembly of claim 3, further comprising:
    communications circuitry electrically coupled to the circuit board, wherein the communications circuitry is operative to receive instructions from a source remote to the patch assembly, and wherein the control electronics is operative to selectively activate the at least one FLA based on the received instructions.

5. The patch assembly of claim 4, further comprising at least one sensor electrically coupled to the circuit board, wherein data obtained by the at least one sensor is transmitted to the source via the communications circuitry.

6. The patch assembly of claim 1, wherein the at least one battery is removable from the flexible substrate.

7. The patch assembly of claim 1, wherein the at least one FLA is operative to provide one of hip flexor assistive movements, hip extensor assistive movements, and spinal extensor movements.

8. An exosuit comprising:
a base layer comprising a plurality of load distribution members, wherein each load distribution member comprises:
catenary curve members that collectively wrap around a portion of a body, wherein an intersection of two catenary curve members forms an anchor point, wherein when a load is applied to the anchor point, the load is distributed around the portion of the body via the catenary curved members; and
a plurality of patch assemblies detachably coupled to the base layer via the plurality of load distribution members, wherein each one of the plurality of patch assemblies comprises:
a flexible substrate comprising mounting components to secure the flexible substrate to one of the load distribution members;
at least one flexible linear actuator (FLA) coupled to the flexible substrate and to the anchor point of one of the load distribution members, wherein the at least one FLA comprises a motor and a twisted string, wherein a first end of the twisted string is coupled to a rotatable member associated with the motor and a second end of the twisted string extends distally away from the motor and is attached to the anchor point of another one of the load distribution members;
at least one battery; and
control electronics coupled to the at least one FLA and the at least one battery and configured to selectively activate the at least one FLA to provide muscle movement assistance to a user of the exosuit, wherein the at least one FLA shortens a length of the twisted string to apply a force during the muscle movement assistance,
wherein when each of the patch assemblies is removed from or attached to the exosuit, the combination of the flexible substate, the at least one FLA, the at least one battery, and the control electronics is collectively removed from or attached to the exosuit as a modular patch.

9. The exosuit of claim 8, wherein each one of the plurality of patch assemblies further comprises communications circuitry to transmit and receive data.

10. The exosuit of claim 9, wherein the plurality of patch assemblies comprises first, second, and third patch assemblies, and wherein the control electronics in the first patch assembly serve as a master controller, and wherein the control electronics in the second and third patch assemblies serve as slave controllers, and wherein the master controller communicates with the slave controllers via the communications circuitry.

11. The exosuit of claim 10, wherein each of the first, second, and third patch assemblies are self-contained systems that supply power to and drive control over the at least one FLA.

12. The exosuit of claim 11, wherein the slave controllers exercise drive control over the at least one FLA based on instructions received from the master controller.

13. The exosuit of claim 10, wherein each of the second and third patch assemblies further comprise at least one sensor that provides data to the master controller via the communications circuitry.

14. The exosuit of claim 8, wherein the at least one FLA of a first patch assembly is operative to provide spinal extensor movements, wherein the at least one FLA of a second patch assembly is operative to provide one of hip flexor assistive movements and hip extensor assistive movements, wherein the at least one FLA of a third patch assembly is operative to provide one of hip flexor assistive movements and hip extensor assistive movements.

15. A multiple assistive movement patch assembly for use with an exosuit, comprising:
a flexible substrate constructed to be detachably coupled to a plurality of load bearing members existing on anterior and posterior sides of the exosuit;
a plurality of sensors secured to the flexible substrate;
a plurality of batteries secured to the flexible substrate;
a plurality of flexible linear actuators (FLAs) secured to the flexible substrate;
control electronics secured to the flexible substrate; and
a power and communications network that is coupled to the plurality of sensors, the plurality of batteries, the plurality of FLAs, and the control electronics, wherein the control electronics are operative to selectively activate the plurality of FLAs to provide muscle movement assistance to a user of the exosuit,
wherein the flexible substrate is a single unitary patch and is designed to be draped around the exosuit by a user and further secured to the exosuit by the user, wherein when the single unitary patch is removed from or attached to the exosuit, the combination of the flexible substate, the plurality of FLAs, the plurality of batteries, the control electronics, and the power and communications network is collectively removed from or attached to the exosuit.

16. The multiple assistive movement patch assembly of claim 15, wherein the plurality of FLAs comprises a first set of FLAs that provide hip flexor assistive movements and a second set of FLAs that provide hip extensor assistive movements, wherein the first and second sets of FLAs are mutually exclusive.

* * * * *